(12) United States Patent
Graham et al.

(10) Patent No.: US 8,168,415 B2
(45) Date of Patent: May 1, 2012

(54) AXL FUSION PROTEINS AS AXL TYROSINE KINASE INHIBITORS

(75) Inventors: Douglas Kim Graham, Aurora, CO (US); Susan Louise Sather, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 0 days.

(21) Appl. No.: 12/526,094

(22) PCT Filed: Feb. 7, 2008

(86) PCT No.: PCT/US2008/053337
§ 371 (c)(1),
(2), (4) Date: Dec. 15, 2009

(87) PCT Pub. No.: WO2008/098139
PCT Pub. Date: Aug. 14, 2008

(65) Prior Publication Data
US 2011/0014173 A1    Jan. 20, 2011

Related U.S. Application Data

(60) Provisional application No. 60/888,741, filed on Feb. 7, 2007.

(51) Int. Cl.
*A61K 39/21*    (2006.01)
*A61K 38/54*    (2006.01)

(52) U.S. Cl. ........................................ 435/188; 424/94.3

(58) Field of Classification Search ........................ None
See application file for complete search history.

(56) References Cited

U.S. PATENT DOCUMENTS

| | | | |
|---|---|---|---|
| 4,683,202 | A | 7/1987 | Mullis |
| 5,554,601 | A | 9/1996 | Simpkins et al. |
| 5,585,269 | A | 12/1996 | Earp, III et al. |
| 6,323,323 | B1 | 11/2001 | Sledziewski et al. |
| 2003/0068759 | A1 | 4/2003 | Baker et al. |
| 2003/0144237 | A1 | 7/2003 | Carmeliet et al. |
| 2004/0157774 | A1 | 8/2004 | Yang et al. |

FOREIGN PATENT DOCUMENTS

| | | |
|---|---|---|
| EP | 1382969 | 1/2004 |
| WO | WO 95/33499 | 12/1995 |
| WO | WO 2006/058202 | 6/2006 |

OTHER PUBLICATIONS

Altschul et al., "Gapped Blast and PSI-Blast: a new generation of protein database search programs," Nucleic Acids Research, 1997, vol. 25, pp. 3389-3402.
Eckert et al., "DNA Polymerase Fidelity and the Polymerase Chain Reaction," PCR Methods and Applications, 1991, vol. 1, pp. 17-24.
Graham et al., "A soluble truncated form of the Mer tyrosine kinase inhibits Gas6 activity in platelets and monocytes," Blood, 2004, vol. 104(11), pp. 436A.
Guatelli et al., "Isothermal, in vitro amplification of nucleic acids by a multienzyme reaction modeled after retroviral replication," Proc. Nat. Acad. Sci. USA, 1990, vol. 87, pp. 1874-1878.
Holland et al., "Multiple Roles for the Receptor Tyrosine Kinase Axl in Tumor Formation," Cancer Research, 2005, vol. 65, pp. 9294-9303.
Kwoh et al., "Transcription-based amplification system and detection of amplified human immunodeficiency virus type 1 with a bead-based sandwich hybridization format," Proc. Natl. Acad. Sci. USA, 1989, vol. 86, pp. 1173-1177.
Landegren et al., "A ligase-mediated gene detection technique," Science, 1988, vol. 241, pp. 1077-1080.
Langer, "New methods of drug delivery," Science, 1990, vol. 249, pp. 1527-1533.
Lu et al., "Tyro-3 family receptors are essential regulators of mammalian spermatogenesis," Nature, 1999, vol. 398, pp. 723-728.
Lu et al., "Homeostatic regulation of the immune system by receptor tyrosine kinases of the Tyro 3 family," Science, 2001, vol. 293, pp. 306-311.
Mattila et al., "Fidelity of DNA synthesis by the *Thermococcus litoralis* DNA polymerase—an extremely heat stable enzyme with proofreading activity," Nucleic Acids Research, 1991, vol. 19, pp. 4967-4973.
O'Bryan et al., "Axl, a transforming gene isolated from primary human myeloid leukemia cells, encodes a novel receptor tyrosine kinase," Molecular and Cellular Biology, 1991, vol. 11(10), pp. 5016-5031.
Sather et al., "A soluble form of the Mer receptor tyrosine kinase inhibits macrophage clearance of apoptotic cells and platelet aggregation," Blood, 2007, vol. 109(3), pp. 1026-1033.
Scott et al., "Phagocytosis and clearance of apoptotic cells is mediated by MER," Nature, 2001, vol. 411, pp. 207-211.
Shankar et al., "Gas6/Axl signaling activates the phosphatidylinositol 3-kinase/Akt1 survival pathway to protect oligodendrocytes from tumor necrosis factor alpha-induced apoptosis," Journal of Neuroscience, 2006, vol. 26(21), pp. 5638-5648.
Stenhoff et al., "Vitamin K-dependent Gas6 activates ERK kinase and stimulates growth of cardiac fibroblasts," Biochemical and Biophysical Research Communications, 2004, vol. 319(3), pp. 871-878.
Yanagita et al., "Essential role of Gas6 for glomerular injury in nephrotoxic nephritis," J. Clin. Invest., 2002, vol. 110, pp. 239-246.
Yanagita et al., "Gas6 regulates mesangial cell proliferation through axl in experimental glomerulonephritis," American Journal of Pathology, 2001, vol. 158(4), pp. 1423-1432.
Extended European Search Report for European Patent Application No. 08729313.0, dated Nov. 11, 2010.
U.S. Appl. No. 11/720,185, Graham (May 24, 2007).
Angelillo-Scherrer et al., "Deficiency or inhibition of Gas6 causes platelet dysfunction and protects mice against thrombosis", Nature Medice, vol. 7, No. 2, Feb. 2001, p. 215-221.

(Continued)

*Primary Examiner* — Robert Landsman
(74) *Attorney, Agent, or Firm* — Sheridan Ross, P.C.

(57) ABSTRACT

Disclosed are novel inhibitors of the Axl receptor tyrosine kinase (RTK) and methods of using such inhibitors in a variety of therapeutic approaches in the areas of cancer therapy and anti-thrombosis (anti-clotting) therapy.

6 Claims, 9 Drawing Sheets

OTHER PUBLICATIONS

Angelillo-Scherrer et al., "Role of Gas6 receptors in platelet signaling during thrombus stabilization and implication for antithrombotic therapy", The Journal of Clinical Investigation, vol. 115, No. 2, Feb. 2005, p. 237-246.

Behrens et al., "The mer receptor tyrosine kinase: expression and function suggest a role in innate immunity," Eur J Immunol, 2003, 33:2160-2167.

Camenisch et al. "A Novel Receptor Tyrosine Kinase, Mer, Inhibits TNF-Production and Lipopolysaccharide-Induced Endotoxic Shock." Journal of Immunology, Mar. 1999, vol. 162, No. 6, pp. 2498-3503.

Chen et al., "Identification of Gas6 as a ligand for Mer, a neural cell adhesion molecule related receptor tyrosine kinase implicated in cellular transformation", Oncogene, vol. 14, 1997, p. 2033-2039.

Chen et al., "Mer Receptor Tyrosine Kinase Signaling Participates in Platelet Function", Arteriorcler. Thromb. Vasc. Biol. 2004; 24; p. 1118-1123 and cover.

Chung et al., "Expression of the proto-oncogene Axl in renal cell carcinoma," DNA Cell Biol. Aug. 2003;22(8):533-40.

Cohen Philip et al., "Delayed apoptotic cell clearance and lupus-like autoimmunity in mice lacking the c-mer membrane tyrosine kinase", The Journal of Experimental Medicine, Jul. 1, 2002, vol. 196, No. 1, pp. 135-140.

Ek et al., "Mantle cell lymphomas express a distinct genetic signature affecting lymphocyte trafficking and growth regulation as compared with subpopulations of normal human B cells." Cancer Research Aug. 1, 2002, vol. 62, No. 15, pp. 4398-4405.

Feng Wei et al., "Mertk triggers uptake of 1-48 photoreceptor outer segments during phagocytosis by cultured retinal pigment epithelial cells", The Journal of Biological Chemistry, May 10, 2002, vol. 277, No. 19, pp. 17016-17022.

Georgescu et al. "Biological Effects of the c-Mer Receptor Tyrosine Kinase in Hematopoietic Cells Depends on the Grb2 Binding Site in the Receptor and Activation of the NF-kB." Molecular Cell Biology, Feb. 1999, vol. 19, No. 2, pp. 1171-1181.

Gould et al., "Gas6 receptors Axl, Sky and Mer enhance platelet activation and regulated thrombotic responses", Journal of Thrombosis and Haemostasis, vol. 3, p. 733-741 (2005).

Graham Douglas et al., "Ectopic expression of the proto-oncogene Mer in pediatric T-cell acute lymphoblastic leukimia", Clinical Cancer Research: An Official Journal of the American Association for Cancer Research, May 1, 2006, vol. 12, No. 9, pp. 2662-2669.

Ling et al., "Mitogenic Signals and Transforming Potential of Nyk, a Newly Identified Neural Cell Adhesion Molecule-Related Receptor Tyrosine Kinase", Molecular and Cellular Biology, Dec. 1995, p. 6582-6592.

Maria-Magdalena et al., "Biological Effects of c-Mer Receptor Tyrosine Kinase in Hematopoietic Cells Depend on the Grb2 Binding Site in the Receptor and Activation of NF-6B", Molecular and Cellular Biology, Feb. 1999, p. 1171-1181.

Nandrot E. Homozygous Deletion in the Coding Sequence of the c-Mer Gene in RCS Rats Unravels General Mechanisms of Physiological Cell Adhersion and Apoptosis. Neurobiol. Dis., Dec. 2000, vol. 7, No. 6, Pt B, pp. 586-599.

Salzberg et al., "Lymphoblastic leukemia/lymphoma in mice overexpressing the Mer receptor tyrosine kinase." Blood, vol. 106, No. 11, part 1, Nov. 2005, p. 736A.

Sasaki et al., "Structural basis for Gas6Axl signalling," The EMBO Journal (2006) 25, 80-87.

Vajkoczy et al., "Dominant-negative inhibition of the Axl receptor tyrosine kinase suppresses brain tumor cell growth and invasion and prolongs survival," Proc Natl Acad Sci U S A, Apr. 11, 2006;103(15):5799-804.

International Search Report for International (PCT) Application No. PCT/US08/53337, mailed Aug. 25, 2008.

Written Opinion for International (PCT) Application No. PCT/US08/53337, mailed Aug. 25, 2008.

International Preliminary Report on Patentability for International (PCT) Patent Application No. PCT/US2008/053337, mailed Aug. 20, 2009.

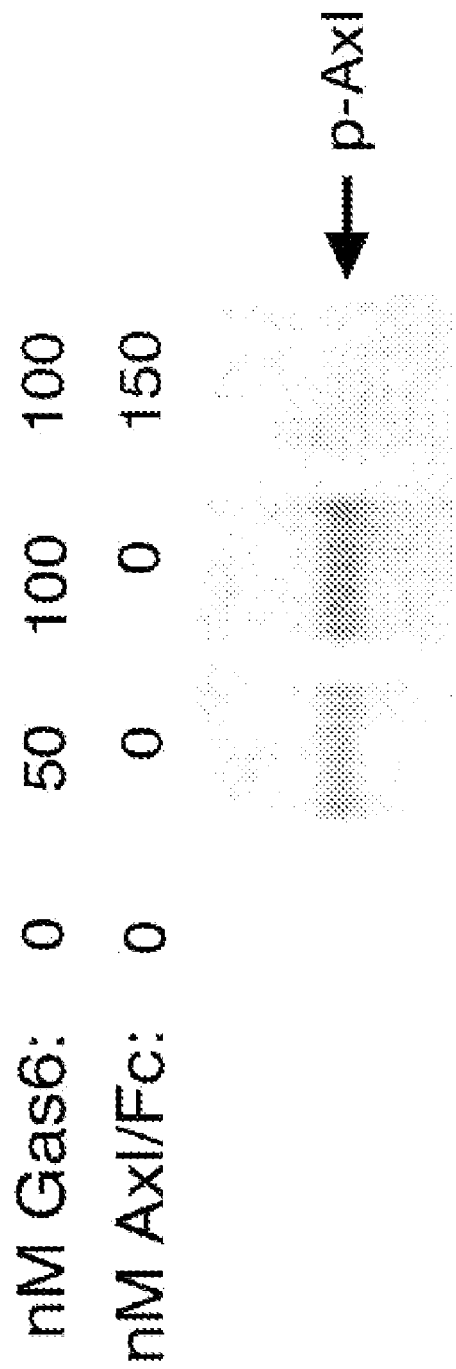

FIG. 5

| agonist | inhibitor | closure time (sec) |
|---|---|---|
| Collagen + epinephrine | none | 135 |
| | 20 μg Axl/Fc | 180 |
| | 40 μg Axl/Fc | 231 |
| | 60 μg Axl/Fc | 231 |
| Collagen + ADP | none | 97 |
| | 40 μg Axl/Fc | 127 |

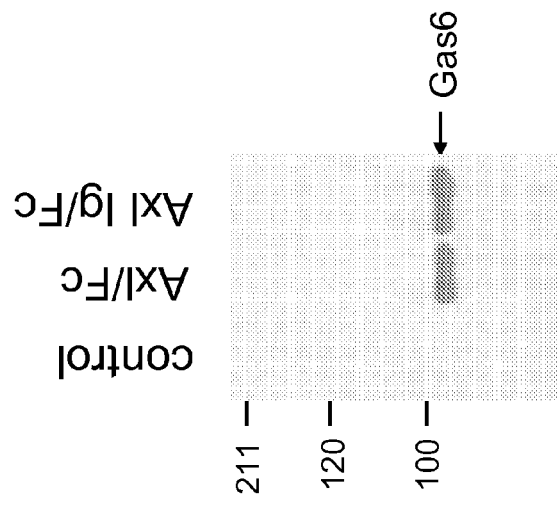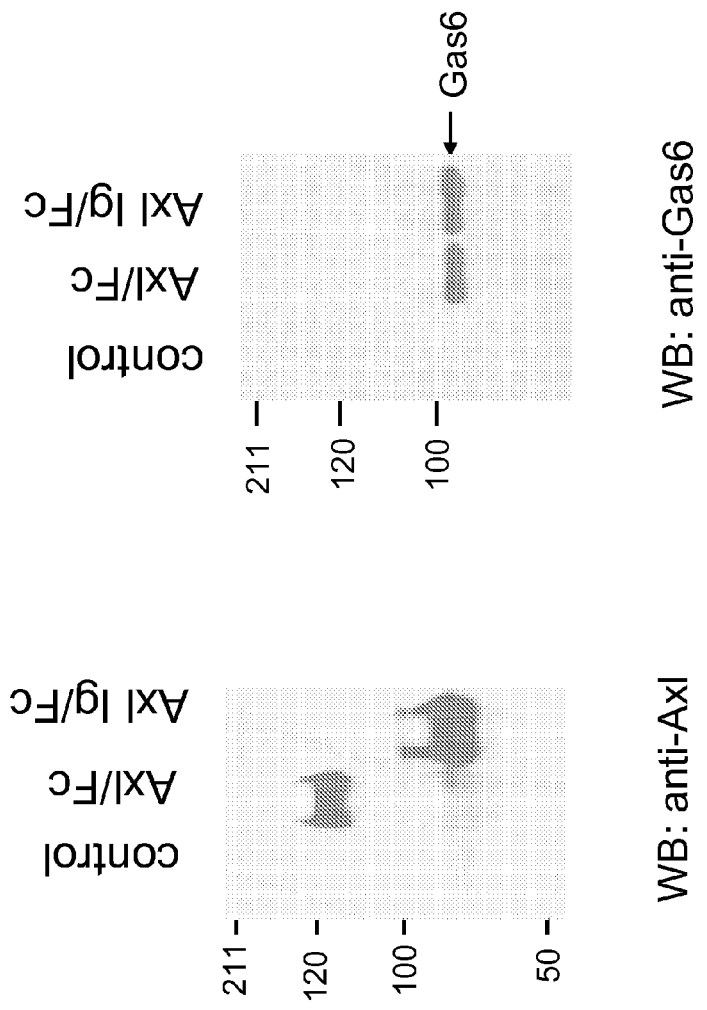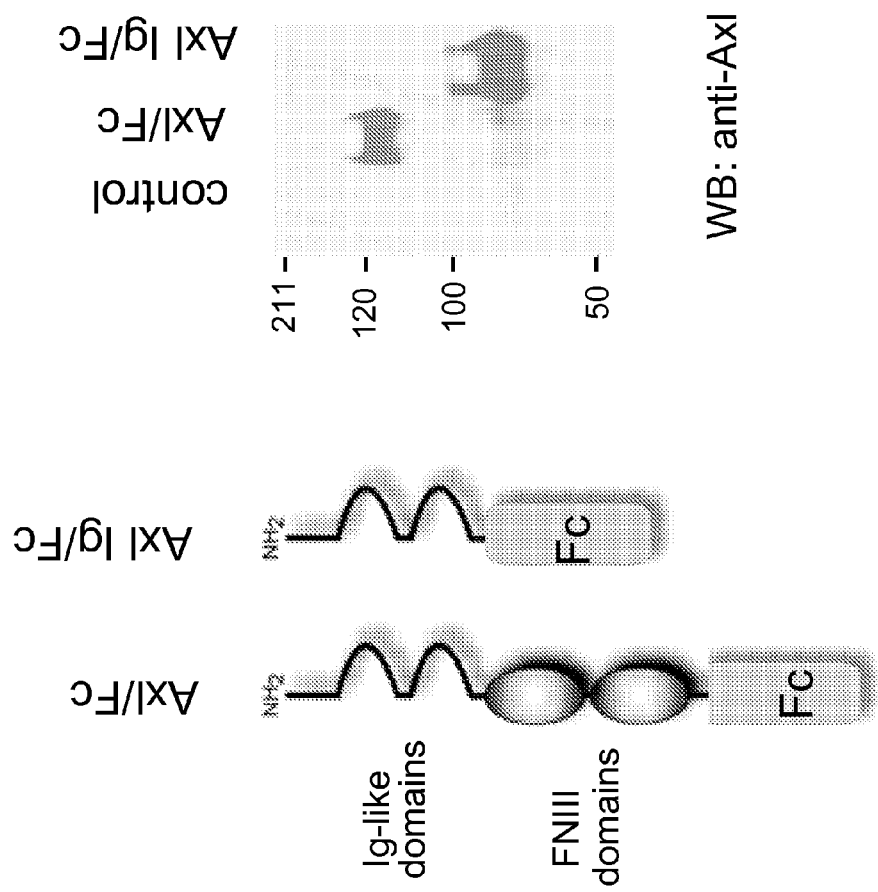

AXL FUSION PROTEINS AS AXL TYROSINE KINASE INHIBITORS

CROSS-REFERENCE TO RELATED APPLICATIONS

This application is a national stage application under 35 U.S.C. 371 of PCT Application No. PCT/US2008/053337, having an international filing date of Feb. 7, 2008, which designated the United States, which PCT application claimed the benefit of U.S. Application Ser. No. 60/888,741, filed Feb. 7, 2007. The entire disclosure of each of these related applications is incorporated herein by reference.

REFERENCE TO SEQUENCE LISTING

This application contains a Sequence Listing submitted as an electronic text file named " Sequence_Listing_2848-95-PUS_ST25" having a size in bytes of 183 KB, and created on Sep. 30, 2010. The information contained in this electronic file is hereby incorporated by reference in its entirety pursuant to 37 CFR §1.52(e)(5).

FIELD OF THE INVENTION

The present invention generally relates to novel inhibitors of the Axl receptor tyrosine kinase (RTK) and to the use of such inhibitors in a variety of compositions and therapeutic approaches in the areas of cancer therapy and anti-thrombosis (anti-clotting) therapy.

BACKGROUND OF THE INVENTION

Drug therapies for many cancers continue to be inadequate, having either limited efficacy, prohibitive toxicities, or in many cases both. As an example, effective therapies are sorely needed for non-small cell lung cancers (NSCLC), of which there are over 162,000 deaths per year according to the National Cancer Institute. Eighty percent of the over 200,000 new diagnoses of lung cancer each year are non-small cell carcinomas. While some patients are successful candidates for surgical resection or radiation therapy, most patients have disseminated disease at the time of diagnosis and are therefore not candidates for these approaches. Most patients diagnosed in the later stages will need to be treated with a variety of therapies including chemotherapies and biologically targeted therapies, neither of which work well for the majority of patients. Results of standard treatment are poor except for the most localized cancers, and currently, no single chemotherapy or biologic regimen can be recommended for routine use. Furthermore, according to the National Cancer Institute, there are nearly 12,000 new diagnoses of myeloid leukemia and over 9,000 deaths from this cancer each year. Thirty to 40% of patients will not attain complete remission of this disease following standard chemotherapy, and only 25% of those attaining complete remission are expected to live longer than 3 years. Thus as with most cancers, there continues to be a need for new therapies that can keep the cancer in remission and increase survival.

There are several new, biologically targeted agents under investigation for NSCLC and other cancers in the hopes that these new agents will expand the pool of patients who respond to and receive a survival benefit from these therapies. In recent years, inhibition of specific cancer-associated tyrosine kinases has emerged as an important approach for cancer therapy. Tyrosine kinases as mediators of cell signaling, play a role in many diverse physiological pathways including cell growth and differentiation. Deregulation of tyrosine kinase activity can result in cellular transformation leading to the development of human cancer. Of the nearly thirty novel cancer targets extensively studied in the past ten years, one third of these are tyrosine or other kinases. Of the ten truly novel anti-cancer therapies approved in the past five years, five of these have been directed against receptor tyrosine kinases (RTKs). In fact, many cancer treatment protocols now use a combination of traditional chemotherapy drugs and novel biologically targeted agents, several of which inhibit tyrosine kinase activity or downstream signaling pathways. For example, a small molecule drug that inhibits the abl tyrosine kinase has led to significant improvement in outcomes for patients with chronic myelogenous leukemia. Inhibitors of other tyrosine kinases, including the Flt-3, EGFR, and PDGF receptor tyrosine kinases are also in clinical trials.

The Axl receptor tyrosine kinase (Axl), originally identified as a protein encoded by a transforming gene from primary human myeloid leukemia cells, is overexpressed in a number of different tumor cell types and transforms NIH3T3 fibroblasts (O'Bryan et al., *Mol. Cell Bio.* 11:5016-5031 (1991)). Axl signaling has been shown to favor tumor growth through activation of proliferative and anti-apoptotic signaling pathways, as well as through promotion of angiogenesis and tumor invasiveness. Axl is associated with the development and maintenance of various cancers including lung cancer, myeloid leukemia, uterine cancer, ovarian cancer, gliomas, melanoma, prostate cancer, breast cancer, gastric cancer, osteosarcoma, renal cell carcinoma, and thyroid cancer, among others. Furthermore, in some cancer types, particularly non-small cell lung cancer (NSCLC), myeloid leukemia, and gastric cancers, the over-expression of this cell signaling molecule indicates a poor prognosis for the patient. Researchers have found that siRNA knockdown of Axl in NSCLC cell lines reduced invasive capacity of the tumor cells (Holland et al., 2005, *Cancer Res.* 65:9294-9303). Vajkoczy et al. have shown that expression of a dominant-negative Axl construct decreased brain tumor proliferation and invasion (Vajkoczy et al., 2006, *PNAS* 15:5799-804; European Patent Publication No. EP 1 382 969 A1). Furthermore, in clinical patient samples of NSCLC, Axl protein over-expression has been statistically associated with lymph node involvement and advanced clinical stage of disease.

Axl signaling also plays important roles in spermatogenesis (Lu et al., 1999, *Nature* 398:723-728), immunity (Lu and Lemke, 2001, *Science* 293: 306-311; Scott et al, 2001, *Nature* 411: 207-211), platelet function (Angelillo-Scherrer et al, 2001, 2005) and even kidney pathology (Yanagita et al, 2002, J Clin Invest 110:239-246).

Axl is related to two other receptor tyrosine kinases, Mer and Tyro-3. Axl, Mer, and Tyro-3 are all expressed in a spectrum of hematopoeitic, epithelial, and mesenchymal cell lines. Each protein has been shown to have the capability to transform cells in vitro. Axl, Mer, and Tyro-3 are all activated by the ligand Gas6. Gas6 is structurally similar to Protein S, a cofactor for anticoagulant Protein C, and shares 48% protein identity with Protein S, which has also been shown to be a binding ligand of at least Mer and Tyro-3. Gas6 plays a role in coagulation (Angelillo-Scherrer et al., *Nature Medicine* 7:215-21(2002)), and Gas6 antibodies may be used to protect wild type mice against fatal thromboembolism (Angelillo-Scherrer et al., (2002)). Mice with an inactivated Gas6 gene (i.e., Gas6 knockout) have platelet dysfunction that prevents venous and arterial thrombosis. These knockout mice are protected against (have decreased mortality against) fatal collagen/epinephrine induced thromboembolism and inhibited ferric chloride-induced thrombosis in vivo. Gas6 amplifies platelet aggregation and secretion response of platelets to known agonists (Chen et al., *Aterioscler. Thromb. Vasc. Biol.* 24:1118-1123 (2004)). The platelet dysfunction caused by Gas6 is thought to be mediated through the Axl, Mer, or Tyro-3. In addition, mice with an inactivated Mer gene, inactivated Axl gene, or an inactivated Tyro-3 gene, all have platelet dysfunction, as well as decreased mortality against thromboembolism (by both statis-induced thrombosis in the inferior vena cava and by collagen-epinephrine induced pulmonary embolism (Angelillo-Scherrer et al., 2005, *J. Clin Invest.* 115:237-246). Therefore, in addition to its association with neoplastic disease, Axl is also involved in blood clotting.

Various types of thrombosis and the complications associated with thrombosis represent a major cause of morbidity and death in the world. Although there are a variety of agents to thin the blood, all have the potential for bleeding complications, and with the exception of heparin (which itself cannot be tolerated by many patients), are largely irreversible. Malignant cellular growth or tumors (cancer) are also a leading cause of death worldwide. Accordingly, the development of effective therapy for cardiovascular and neoplastic disease is the subject of a large body of research. Although a variety of innovative approaches to treat and prevent such diseases have been proposed, these diseases continue to have a high rate of mortality and may be difficult to treat or relatively unresponsive to conventional therapies. Therefore, there is a continued need in the art for new therapies that can effectively target and prevent or treat these diseases. Because it is generally the case in cancer therapy that no single agent can successfully treat a patient, new agents can continue to be developed and ultimately used in combination with other agents to affect the best outcome for patients.

SUMMARY OF THE INVENTION

One embodiment of the invention relates to an Axl inhibitor, wherein the Axl inhibitor is preferably an Axl fusion protein. The Axl fusion protein comprises: (a) a first protein comprising, consisting essentially of, or consisting of, at least a portion of the extracellular domain of an Axl receptor tyrosine kinase (Axl RTK) that binds to an Axl ligand; and (b) a second protein that is a heterologous fusion protein, wherein the second protein is fused to the first protein.

In one aspect, the first protein comprises, consists essentially of, or consists of the Gas6 major binding site of Axl. In one aspect, the first protein comprises, consists essentially of, or consists of the Gas6 major binding site and the Gas6 minor binding site of Axl. In one aspect, the first protein comprises, consists essentially of, or consists of the Ig1 domain of Axl. In one aspect, the first protein comprises, consists essentially of, or consists of the Ig1 domain and the Ig2 domain of Axl. In one aspect, the first protein comprises, consists essentially of, or consists of a portion of the extracellular domain of Axl RTK in which at least one of the FBNIII motifs in the first protein is deleted or mutated of Axl. In one aspect, the first protein comprises, consists essentially of, or consists of a portion of the extracellular domain of Axl RTK in which both of the FBNIII motifs is deleted or mutated of Axl. In one aspect, the first protein comprises, consists essentially of, or consists of, the entire Axl RTK extracellular domain of Axl. In one aspect, the first protein comprises, consists essentially of, or consists of positions 1-445 of Axl RTK, with respect to SEQ ID NO:2. In one aspect, the first protein comprises, consists essentially of, or consists of positions 1-324 or 1-325 of Axl RTK, with respect to SEQ ID NO:2. In one aspect, the first protein comprises, consists essentially of, or consists of position 1 to position 222, 223, 224, or 225 of Axl RTK, with respect to SEQ ID NO:2. In one aspect, the first protein comprises, consists essentially of, or consists of at least: position 10 to position 222, 223, 224, or 225 of Axl RTK, position 20 to position 222, 223, 224, or 225 of Axl RTK, position 30 to position 222, 223, 224, or 225 of Axl RTK, position 40 to position 222, 223, 224, or 225 of Axl RTK, position 50 to position 222, 223, 224, or 225 of Axl RTK, or position 60 to position 222, 223, 224, or 225 of Axl RTK, with respect to SEQ ID NO:2. In one aspect, the first protein comprises, consists essentially of, or consists of: at least positions 63-225 of SEQ ID NO:2. In one aspect, the first protein comprises, consists essentially of, or consists of at least: positions 1-137 of Axl RTK, positions 10-137 of Axl RTK, positions 20-137 of Axl RTK, positions 30-137 of Axl RTK, positions 40-137 of Axl RTK, positions 50-137 of Axl RTK, or positions 60-137 or Axl RTK, with respect to SEQ ID NO:2. In one aspect, the first protein comprises, consists essentially of, or consists of at least positions 63 to 218 of SEQ ID NO:2. In one aspect, the first protein comprises at least positions 63-99, 136, 138, and 211-218 of SEQ ID NO:2, arranged in a conformation that retains the tertiary structure of these positions with respect to the full-length extracellular domain of Axl RTK (positions 1-445 of SEQ ID NO:2).

In any of the above aspects of the invention, the invention the Axl RTK can comprise an amino acid sequence that is at least 80% identical, at least 90% identical, or at least 95% identical, to SEQ ID NO:2 or SEQ ID NO:4. In one aspect, the Axl RTK comprises an amino acid sequence of SEQ ID NO:2 or SEQ ID NO:4.

In any of the above aspects of the invention, the fusion protein can be produced as a dimer of Axl proteins.

In any of the above aspects of the invention, the heterologous fusion protein (the second protein) is an immunoglobulin Fc domain. In one aspect, the immunoglobulin Fc domain consists essentially of or consists of a heavy chain hinge region, a $CH_2$ domain and a $CH_3$ domain. In one aspect, the immunoglobulin Fc domain is from an IgG immunoglobulin protein. In one aspect, the immunoglobulin Fc domain is from an IgG1 immunoglobulin protein. In one aspect, the immunoglobulin Fc domain is from a human immunoglobulin.

In another aspect of any of the above aspects of the invention, the fusion protein can further comprise a third protein, fused to the first or to the second protein. In one aspect, the third protein is a pro-apoptosis protein or an anti-clotting protein.

In any of the above aspects related to an Axl fusion protein of the invention, in one aspect, the Axl ligand is Gas6.

In any of the above aspects related to an Axl fusion protein of the invention, in one aspect, the Axl fusion protein binds to the Axl ligand with an equal or greater affinity as compared to a naturally occurring Axl receptor tyrosine kinase. In one aspect, the Axl fusion protein inhibits binding of the Axl ligand to an endogenous Axl receptor tyrosine kinase by at least 50%. In another aspect, the Axl fusion protein inhibits binding of the Axl ligand to an endogenous Axl receptor tyrosine kinase by at least 60%. In another aspect, the Axl fusion protein inhibits binding of the Axl ligand to an endogenous Axl receptor tyrosine kinase by at least 70%. In another aspect, the Axl fusion protein inhibits binding of the Axl ligand to an endogenous Axl receptor tyrosine kinase by at least 80%.

In any of the above aspects related to an Axl fusion protein of the invention, in one aspect, the Axl fusion protein does not activate Mer or Tyro-3.

Another embodiment of the invention relates to a composition comprising, consisting essentially of, or consisting of any of the Axl fusion proteins described herein. In one aspect of this embodiment, the composition further comprises a pharmaceutically acceptable carrier. In another aspect, the composition further comprises at least one therapeutic agent for treatment of cancer. In another aspect, the composition further comprises at least one therapeutic agent for treatment of a clotting disorder. In another aspect, the composition further comprises a Mer-Fc or a Tyro-3-Fc. In this latter aspect, preferably, the Mer-Fc does not activate Axl or Tyro-3.

Yet another embodiment of the present invention relates to a method of treating cancer in an individual, comprising administering to the individual any of the Axl fusion proteins or the compositions described herein. In one aspect, the cancer is an Axl-positive cancer. In another aspect, the cancer is a Mer-positive cancer. In another aspect, the cancer is a Tyro-3-positive cancer. In one aspect, the cancer is selected from: lung cancer, myeloid leukemia, uterine cancer, ovarian cancer, gliomas, melanoma, prostate cancer, breast cancer, gastric cancer, osteosarcoma, renal cell carcinoma, or thyroid cancer. In one aspect, the cancer is a leukemia or lymphoma. In another aspect, the cancer is myeloid leukemia. In another aspect, the cancer is non-small cell lung cancer (NSCLC).

Yet another embodiment of the invention relates to a method of treating or preventing a clotting disorder in an individual, comprising administrating to the individual any of the Axl fusion proteins or compositions described herein. In one aspect, the disorder is selected from the group consisting of: thrombophilia, thrombosis and thrombo-embolic disorder. In one aspect, the disorder is thrombophilia. In one aspect, the individual is taking a medication that increases the risk of clotting in the individual. In one aspect, the individual has a disease associated with thrombosis. In one aspect, the disease is selected from the group consisting of: cancer, myeloproliferative disorders, autoimmune disorders, cardiac disease, inflammatory disorders, atherosclerosis, hemolytic anemia, nephrosis, and hyperlipidemia. In one aspect, the individual is undergoing surgery, an interventional or cardiac procedure, is experiencing or has experienced trauma, or is pregnant.

Another embodiment of the invention relates to the use of any of the Axl fusion proteins or compositions described herein in the preparation of a medicament for the treatment of cancer.

Yet another embodiment of the invention relates to the use of any of the Axl fusion proteins or compositions described herein in the preparation of a medicament for the prevention or treatment of a clotting disorder.

BRIEF DESCRIPTION OF THE FIGURES OF THE INVENTION

FIG. 3 is a digital image of a Western blot showing that Axl-Fc prevents Axl activation and signaling by Gas6.

FIG. 5 is a tabular graph showing that Axl-Fc prolongs in vitro clotting time in response to collagen and epinephrine or collagen and ADP.

FIG. 7A is a schematic drawing showing the structure of AxlFc as compared to AxlIgFc.

FIG. 7B is a digitized image of a Western blot showing that AxlFc is expressed in transfected HEK293 cells and is detected as a protein approximately 115 kD and that AxlIgFc is approximately 65-75 kD.

FIG. 7C is a digitized image of a Western blot showing that both AxlFc and AxlIgFc bind Gas6 in a pulldown assay.

DETAILED DESCRIPTION OF THE INVENTION

Figure 1:
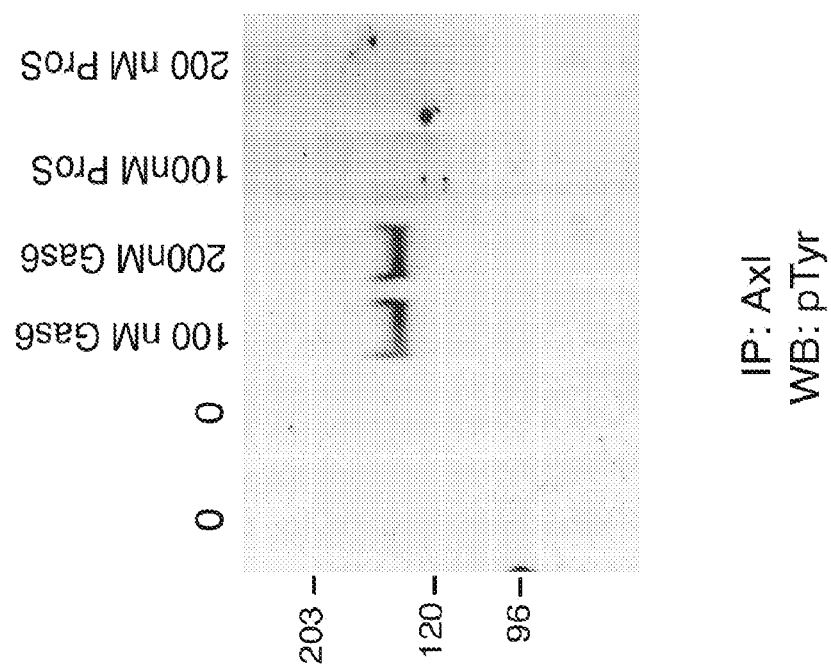
FIG. 1 is a digital image of a blot showing that Gas6 activates Axl in a non-small cell lung cancer cell line, A549.

The present invention generally relates to novel inhibitors of the Axl receptor tyrosine kinase (RTK) and methods of using such inhibitors in a variety of therapeutic approaches in the areas of cancer therapy and anti-thrombosis (anti-clotting) therapy. The present inventors describe herein a family of Axl RTK inhibitors and have demonstrated that such therapeutic agents can bind the ligand, Gas6, and inhibit activation of membrane-bound Axl in the A549 non small cell lung cancer (NSCLC) cell line. The inventors propose herein to use these agents as biologic therapeutics for the treatment of many Axl-overexpressing cancers, including NSCLC. Many other human cancers have been found to have over-expression of Axl, including myeloid leukemia, and the novel Axl inhibitors described herein are believed to be useful for the treatment of these cancers. In addition, the inhibitors of the present invention are useful for the treatment of clotting disorders (e.g., as an anti-clotting agent).

More particularly, the present inventors have developed inhibitors of Axl that are capable of preventing Axl activation by sequestration of Axl ligands. In one particular embodiment, the present inventors have developed Axl inhibitors that inhibit the activation of Axl, and do not activate Mer (in the presence of Gas6). Specifically, the inventors have demonstrated that this novel therapeutic can bind the ligand Gas6 and inhibit activation of membrane-bound Axl in the A549 non small cell lung cancer (NSCLC) cell line. It is proposed herein that this Axl ligand "sink" can be used as a biologic therapeutic agent for the sequestration of Axl ligands and accordingly, for the treatment of Axl overexpressing cancers, including, but not limited to, lung cancer, myeloid leukemia, uterine cancer, ovarian cancer, gliomas, melanoma, prostate cancer, breast cancer, gastric cancer, osteosarcoma, renal cell carcinoma, and thyroid cancer. The inhibitors of the invention are useful for treating both Axl-positive and Mer-positive cancers. In addition, the novel therapeutic agents of the invention are useful in the treatment of clotting disorders (anti-thrombotic therapy).

Axl Inhibitors of the Invention

The invention includes, as one embodiment, an Axl inhibitor, and compositions comprising such inhibitor. The Axl inhibitors of the present invention generally comprise the extracellular domain of Axl or more preferably, a portion thereof (described below), fused (linked, joined) to a fusion partner, e.g., an Fc region of an immunoglobulin, to allow crosslinking The extracellular domain of Axl or the portion thereof includes at least one domain that binds to and sequesters ligand (at least one ligand binding domain), and/or at least one domain that binds to a TAM receptor (at least one TAM receptor binding domain) directly to inhibit activation and signaling through the TAM receptor (e.g., by preventing/blocking ligand binding or by preventing receptor dimerization, trimerization or formation of any receptor-protein complex). TAM (Tyro-Axl-Mer) receptors include Tyro, Axl, and Mer receptor tyrosine kinases. The inhibitors can be further combined with other therapeutic reagents to enhance or supplement other therapeutic treatments for neoplastic and thrombotic disorders or conditions. Also included in the invention are peptides and mimetics thereof that bind to the ligand binding site of Axl and thereby inhibit the binding of Axl to Gas6 or another ligand. The inhibitors of the invention are described in detail below.

General reference to an "Axl inhibitor" refers to any of the Axl inhibitors described herein, and include the Axl proteins described herein fused to any suitable fusion partner encompassed by the invention. General reference to an Axl-Fc can refer to any Axl protein described herein fused to any Fc portion of an immunoglobulin as described herein. However, in some instances, "Axl-Fc" or "AxlFc" is used to particularly describe a full-length extracellular domain of Axl (described below) fused to an Fc domain. Truncated versions of an Axl extracellular domain as described herein can be denoted by more specific names reflecting the Axl fusion protein. For example, an "Axl Ig/Fc" protein can refer herein to a portion of Axl comprising only the Ig domains, which is fused to an Fc portion.

Figure 6B:
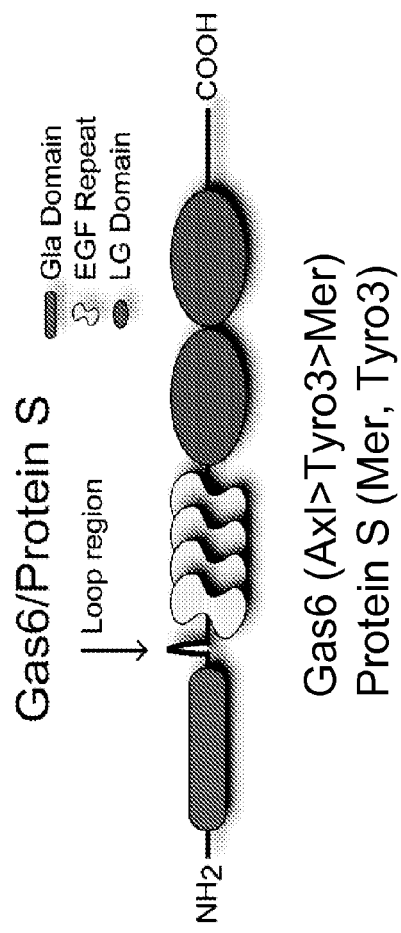
FIG. 6B shows is a schematic drawing showing the structural motifs for the ligands for TAM receptors, Gas6 and Protein S.
Figure 6A:
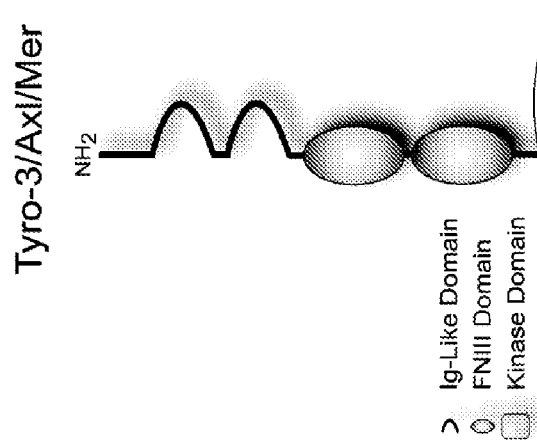
FIG. 6A is a schematic drawing showing that the TAM family members (Tyro-3, Axl, Mer) have two Ig-like motifs and two FNIII like motifs in the extracellular domain, a transmembrane region, and an intracellular tyrosine kinase domain, with the conserved sequence KW(I/L)A(I/L)/ES (SEQ ID NO:18).

The Axl RTK is a member of the receptor tyrosine kinase subfamily. Although it is similar to other receptor tyrosine kinases, the Axl protein represents a unique structure in its extracellular region that juxtaposes immunoglobulin (IgL) repeats and fibronectin type III (FNIII) repeats, a structure it shares with TAM (Tyro-Axl-Mer) family members, Mer and Tyro-3. FIG. 6A is a schematic drawing illustrating the TAM family member immunoglobulin (Ig) and fibronectin type III (FNIII) extracellular motifs and an intracellular tyrosine kinase domain. The extracellular Ig and FNIII motifs are believed to be important in cell adhesion and migration, and indicate a means through which the Axl oncogene contributes to tumor invasiveness and metastasis. Axl transduces signals from the extracellular matrix into the cytoplasm by binding growth factors like vitamin K-dependent protein growth-arrest-specific gene 6 (Gas6). FIG. 6B illustrates the structural motifs of both Gas6 and protein S, the two ligands bound by members of the TAM family (note that protein S is not known to be a ligand for Axl). Referring to FIG. 1, Axl activation occurs following binding of the Axl receptor to its ligand (e.g., Gas6). This interaction causes Axl dimerization and auto-phosphorylation (see FIG. 1). The Axl gene is in close vicinity to the bcl3 oncogene which is at 19q13.1-q13.2.

The Axl gene is evolutionarily conserved between vertebrate species. Indeed, the nucleic acid sequence (genomic and/or mRNA) and amino acid sequence for Axl RTK from several different species are known in the art. There are two transcript variants of Axl. In humans, transcript variant 1 encodes the full-length Axl isoform (isoform 1), and transcript variant 2 lacks exon 10, resulting in a protein (isoform 2) lacking an internal 9 amino acids, but which is otherwise the same as the full length protein encoded by transcript variant 1. The nucleic acid sequence of the transcript variant 1 of human Axl is represented herein by SEQ ID NO:1 (see also NCBI Accession No. NM_021913.2, GI:21536465). SEQ ID NO:1 encodes human Axl isoform 1, represented herein by SEQ ID NO:2 (see also NCBI Accession No. NP_068713.2, GI:21536466). The nucleic acid sequence of the transcript variant 2 of human Axl is represented herein by SEQ ID NO: 3(see also NCBI Accession No. NM_001699.3, GI:21536467). SEQ ID NO:3 encodes human Axl isoform 2, represented herein by SEQ ID NO:4 (see also NCBI Accession No. NP_001690.2, GI:21536468).

The nucleic acid sequence and encoded amino acid sequence of the Axl RTK is also known for mouse (*Mus musculus*), rat (*Rattus norvegicus*), dog (*Canis familiaris*), cow (*Bos taurus*), chicken (*Gallus gallus*), and zebrafish (*Danio rerio*), as well as other vertebrates. The nucleic acid sequence of mouse Axl and the amino acid sequence of the protein encoded thereby are represented by SEQ ID NO:5 and SEQ ID NO:6, respectively (see also NCBI Accession No. BC058230.1, GI:34849483). The nucleic acid sequence for rat Axl (transcript variant 1) and the amino acid sequence of the protein encoded thereby are represented by SEQ ID NO:7 and SEQ ID NO:8, respectively (see also NCBI Accession No. NM_031794.1, GI:93204848). The nucleic acid sequence for chicken Axl and the amino acid sequence of the protein encoded thereby are represented by SEQ ID NO:9 and SEQ ID NO:10, respectively (see also NCBI Accession No. U70045.1, GI:1572686). The nucleic acid sequence for cow Axl and the amino acid sequence of the protein encoded thereby are represented by SEQ ID NO:11 and SEQ ID NO:12, respectively (see also NCBI Accession No. XM_594754.3, GI:119910556). The nucleic acid sequence for dog Axl (transcript variant 1) and the amino acid sequence of the protein encoded thereby are represented by SEQ ID NO:13 and SEQ ID NO:14, respectively (see also NCBI Accession No. XM_541604.2, GI:73947521). The nucleic acid sequence for zebrafish Axl (transcript variant 1) and the amino acid sequence of the protein encoded thereby are represented by SEQ ID NO:15 and SEQ ID NO:16, respectively (see also NCBI Accession No. XM_695874.1, GI:68427805).

Sasaki et al. (Sasaki et al., 2006, *EMBO Journal* (2006) 25, 80-87) resolved at 3.3 A resolution a minimal human Gas6/Axl complex, revealing substantial information regarding the ligand binding structure of Axl. The coordinates and structure factors of the Gas6-LG/Axl-IG complex have been deposited in the Protein Data Bank (PDB Accession code 2c5d). With respect to the sequences described below, it is noted that the position numbering in Sasaki et al. starts with a methionine that is 7 amino acids downstream from the first methionine in SEQ ID NO:2 disclosed herein. Therefore, all numbering referenced with respect to Sasaki et al. is based on the Sasaki et al. positions (Sasaki et al., 2006, *EMBO Journal* (2006) 25, 80-87).

The extracellular domain of human Axl (SEQ ID NO:2 or SEQ ID NO:4) spans amino acid positions from about 1 to about 445, with respect to SEQ ID NO:2, and contains two Ig domains and two FNIII domains. The first Ig domain, denoted herein as Ig1, includes from about position 33 to about position 137 of SEQ ID NO:2). The second Ig domain, denoted herein as Ig2, includes from about position 139 to about position 222 of SEQ ID NO:2. The first FNIII domain, denoted herein as FNIII(a), includes from about position 225 to about position 328 of SEQ ID NO:2. The second FNIII domain, denoted herein as FNIII(b), includes from about position 337 to about position 418 of SEQ ID NO:2. The corresponding domain in other splice variants and species can be readily determined by aligning the sequences. However, the present invention includes Axl-Fc proteins in which the Axl portion of the protein consists of smaller fragments of the extracellular domains than this full-length extracellular domain.

Figure 2A:
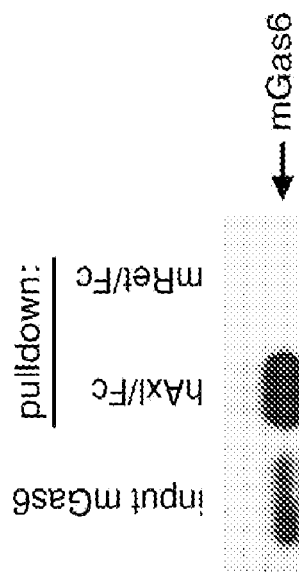
FIG. 2A is a digital image of a Western blot showing that Axl-Fc binds to Gas6 ligand.
Figure 2B:
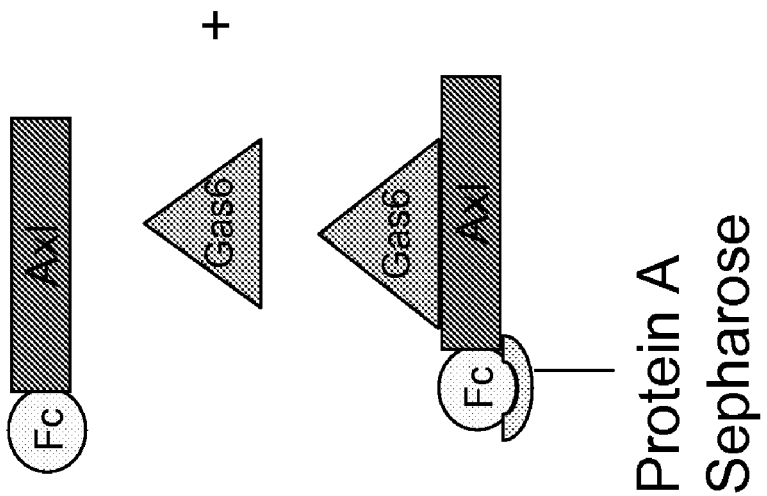
FIG. 2B is a schematic drawing showing how Axl-Fc binds to Gas6 ligand.

For example, Axl proteins useful in the invention can include any smaller portions (fragments) of the extracellular domain of Axl that retain the ability to bind to an Axl ligand (e.g., Gas6), and/or that retain the ability to bind to a TAM receptor (at least one TAM receptor binding domain) to inhibit activation and signaling through the TAM receptor (e.g., by preventing/blocking ligand binding or by preventing receptor dimerization, trimerization or formation of any receptor-protein complex). Preferably, such portions do not activate Mer. Sasaki et al. (Sasaki et al., 2006, supra) teach that an Axl fragment spanning the two N-terminal Ig domains (denoted Ig1 and Ig2) and lacking carbohydrate modifications (Axl-IG) retains full Gas6-LG binding activity (Gas6-LG is the C-terminal portion of Gas6 required for Axl binding). As taught by Sasaki et al., supra, there are two distinct Gas6/Axl contacts of very different size, denoted therein as the major binding site and the minor binding site, both featuring interactions between edge β-strands. Structure-based mutagenesis, protein binding assays and receptor activation experiments performed by Sasaki et al. demonstrated that both the major and minor Gas6 binding sites are required for productive transmembrane signaling, although for the purposes of creating a ligand sink via an Fc-Axl according to the present invention, where signaling is not required, lesser portions can be used. Sasaki et al., supra, taught that Gas6-mediated Axl dimerization is likely to occur in two steps, with a high-affinity 1:1 Gas6/Axl complex forming first. Only the minor Gas6 binding site is highly conserved in the other Axl family receptors, Tyro3 (also known as Sky and Rse) and Mer. Specificity at the major contact is suggested to result from the segregation of charged and apolar residues to opposite faces of the newly formed β-sheet (Sasaki et al., supra). FIG. 2 from Sasaki et al., supra, illustrates a comparison of Axl family members and specifically, shows the domain structure of Axl, and teaches the residues involved in the major Gas6 binding site (in the Ig1 domain) and minor Gas6 binding site (in the Ig2 domain). The major Gas6 binding surface of Axl is generally defined by strand D of Ig1 (six main-chain hydrogen bonds), and the formation of a continuous β-sheet across the major Gas6/Axl contact. More particularly, the major binding surface has the features of a B-C loop of Ig1 containing negatively charged residues, and a long strand D having an unusually apolar surface that is contiguous with exposed apolar residues on strand E. The minor Gas6 binding surface of Axl is generally defined by strand G of the Ig2 domain, with additional contributions from the Ig domain linker.

According to the present invention, the major binding site lies from about Glu63 to about Val99 in the Ig1 domain (with reference to the numbering in SEQ ID NO:2). Using the numbering in Sasaki et al., supra, the major binding site is represented by Glu56 to Val92 in Sasaki et al., 2006, supra. The minor binding site includes strand G (spanning from about position Lys211 to Thr218 with respect to SEQ ID NO:2 or from Lys204-Thr211, with respect to Sasaki et al., 2006, supra) and also includes a few residues in the linker region (Leu138 and Glu136 with respect to SEQ ID NO:2 or Leu129 and Glu131 with respect to Sasaki et al., supra).

Accordingly, a suitable Axl protein for use in the present invention excludes at least the cytoplasmic domain of Axl, and preferably all or the majority of the transmembrane domain of Axl, and includes a portion of the extracellular domain of Axl, up to the entire extracellular domain. Preferably, the portion of the extracellular domain includes at least the major Gas6 binding surface of Axl, and in other embodiments, includes at least the major and the minor Gas6 binding surface of Axl, and in other embodiments, contains at least the Ig1 and Ig2 domains of Axl, or residues therein that form a conformational structure sufficient to bind to an Axl ligand (e.g., Gas6). Glycosylation of the three predicted glycosylation sites in Axl-Ig ($Asn_{36}$, $Asn_{150}$ and $Asn_{191}$ with respect to Sasaki et al., or $Asn_{43}$, $Asn_{157}$, and $Asn_{198}$, with respect to SEQ ID NO:2) is not required for Gas6 binding. In another embodiment, a suitable portion of the extracellular domain includes at least one Ig domain and two FNIII domains.

In another embodiment, a suitable portion of the extracellular domain of Axl for use in the present invention includes both FNIII domains or a sufficient portion thereof to directly bind to a TAM receptor in a manner that inhibits binding of a ligand to the receptor or prevents receptor dimerization, receptor trimerization, or formation of any receptor-protein complex), but does not include not the Ig domains (i.e., ligand binding domains are not included). Such an Axl protein is believed to be useful for binding to a TAM receptor and preventing ligand binding or complexing of TAM receptors (dimerization, trimerization, or formation of any receptor complex), but does not itself bind ligand.

In one embodiment, a suitable Axl protein for use in an Axl inhibitor of the invention, and particularly an Axl-Fc protein, includes positions 1-445, or a ligand-binding portion thereof, with respect to SEQ ID NO:2. In another embodiment, a suitable Axl protein for use in the Axl inhibitor of the invention, and particularly an Axl-Fc protein, comprises, consists essentially of, or consists of positions 1-324 or 1-325, or a ligand-binding portion thereof and/or a TAM binding portion thereof (i.e., sufficient to bind to a TAM receptor inhibit the binding of the natural ligand to its receptor or to inhibit the complexing of the receptor), with respect to SEQ ID NO:2. In any of the above-embodiments, the portion can be shorter than position 324 or 325 (e.g., 323, 322, 321, etc.), or extend beyond position 324 or 325 to any higher position within the extracellular domain of Axl, in whole number increments (e.g., 326, 327, . . . 398 . . . 445).

In another embodiment, a suitable Axl protein for use in the Axl inhibitor of the invention, and particularly an Axl-Fc protein, comprises, consists essentially of, or consists of positions 1 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 10 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 20 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 30 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 33 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 40 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 50 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 60 to about position 222, 223, 224 or 225, with respect to SEQ ID NO:2. In another embodiment, a suitable Axl protein for use in the Axl inhibitor of the invention, and particularly an Axl-Fc protein, comprises, consists essentially of, or consists of positions 63 to about position 222, 223, 224 or 225, with respect to SEQ ID NO:2. In any of the above-embodiments, the portion can be shorter than 222, 223, 224 or 225 (e.g., 221, 220, etc.), or extend beyond position 222, 223, 224 or 225 to any higher position within the extracellular domain of Axl, in whole number increments (e.g., 226, 227, 228, . . . 230 . . . 445).

In another embodiment, a suitable Axl protein for use in the Axl inhibitor of the invention, and particularly an Axl-Fc protein, comprises, consists essentially of, or consists of positions 1 to 137, positions 10 to 137, positions 20 to 137, positions 30 to 137, positions 40 to 137, or positions 50 to 137, with respect to SEQ ID NO:2.

In another embodiment, a suitable Axl protein for use in the Axl inhibitor of the invention, and particularly an Axl-Fc protein, comprises, consists essentially of, or consists of positions 63 to 218 of SEQ ID NO:2 or any additional 1-20 amino acids on either side of these positions. In one embodiment, a suitable Axl protein for use in the Axl inhibitor of the invention, and particularly an Axl-Fc protein, comprises positions 63-99, 136, 138, and 211-218 of SEQ ID NO:2, arranged in a conformation that retains the tertiary structure of the full Axl extracellular domain with respect to the major and minor binding sites.

Fragments within any of these specifically defined fragments are encompassed by the invention, provided that, in one embodiment, the fragments retain ligand binding ability of Axl, preferably with an affinity sufficient to compete with the binding of the ligand to its natural receptor (e.g., naturally occurring Axl) and provide inhibition of a biological activity of Axl or provide a therapeutic benefit to a patient. It will be apparent that, based on the knowledge of residues important for binding to Gas6 within these regions, various conservative or even non-conservative amino acid substitutions can be made, while the ability to bind to Gas6 is retained. While both full-length and truncated forms of the Axl extracellular domains are effective to sequester Gas6, truncated forms that do not activate Mer are preferred for use in the invention. Fragments within any of the above-defined fragments are also encompassed by the invention if they additionally (ligand binding also required), or alternatively (ligand binding not retained), retain the ability to bind to a TAM receptor (at least one TAM receptor binding domain) sufficient to inhibit activation and signaling through the TAM receptor (e.g., by preventing/blocking ligand binding or by preventing receptor dimerization, trimerization or formation of any receptor-protein complex).

Assays for measuring binding affinities are well-known in the art. In one embodiment, a BIAcore machine can be used to determine the binding constant of a complex between the target protein (e.g., an Axl-Fc) and a natural ligand (e.g., Gas6). For example, the Axl inhibitor can be immobilized on a substrate. A natural or synthetic ligand is contacted with the substrate to form a complex. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Contacting a second compound (e.g., a different ligand or a different Axl protein) at various concentrations at the same time as the first ligand and monitoring the response function (e.g., the change in the refractive index with respect to time) allows the complex dissociation constant to be determined in the presence of the second compound and indicates whether the second compound is an inhibitor of the complex. Other suitable assays for measuring the binding of a receptor to a ligand include, but are not limited to, Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry.

In one embodiment, all or a portion of one or both of the FNIII sites of Axl can be deleted or mutated, as well as any intervening linker regions in the extracellular domain of Axl. Again, any deletions or other mutations (substitutions, additions, etc.) are encompassed by the invention, provided that the ligand-binding ability of the Axl-containing protein is retained. Accordingly, the present invention includes the deletion of at least one amino acid from one or both of the FNIII sites, up to all of the amino acids within one or both of the FNIII sites, in whole integers (e.g., one, two, three, four, five, six, seven, eight, nine, ten . . . twenty . . . thirty, etc. deleted amino acids).

In another embodiment, one or both of the FNIII sites of Axl are retained, and may include intervening linker regions in the extracellular domain of Axl. In one aspect of this embodiment, the Axl inhibitor includes only one or both of the FNIII sites of Axl, and more particularly, does not include one or both Ig domains. Such an inhibitor does not bind ligand, but should retain the ability to bind to a TAM receptor (at least one TAM receptor binding domain) sufficient to inhibit activation and signaling through the TAM receptor (e.g., by preventing/blocking ligand binding or by preventing receptor dimerization, trimerization or formation of any receptor-protein complex).

As discussed above, an Axl inhibitor of the invention typically includes a soluble form of Axl that is linked to a fusion partner that permits the formation of a dimer of Axl proteins (e.g., an Fc region of an immunoglobulin protein, other fusion partners that cause dimerization). In one embodiment, an Axl inhibitor of the invention includes a soluble form of Axl that is linked to a fusion partner that allows binding of a ligand without dimerization of the Axl proteins. As used herein, the term "soluble form" of Axl, "sAxl" or "soluble Axl" refers to an Axl receptor tyrosine kinase that does not contain cytoplasmic domains, and preferably no or little of the transmembrane domains of the natural protein (e.g., SEQ ID NO:2), and that includes any portion of the extracellular domain of Axl (described above) that has the ability to bind to an Axl ligand, e.g., a ligand including, but not limited to, Gas6. There are multiple soluble forms of Axl that are operable in the invention. Structural and functional features required of these forms are discussed above. The soluble form of Axl is preferably generated by recombinant means, whereby a construct encoding an entire Axl-Fc protein is produced, although a soluble form of Axl can be generated by post-translational proteolytic cleavage and then later joined with an Fc domain, if desired.

According to the present invention, an Fc protein or fragment (also referred to as Fc domain or Fc region of an immunoglobulin) is a portion of an immunoglobulin (also referred to herein as antibody) lacking the ability to bind to antigen. More particularly, the Fc region (from "Fragment, crystallizable") of an immunoglobulin, is derived from the constant region domains of an immunoglobulin and is generally composed of two heavy (H) chains that each contribute between two and three constant domains (depending on the isotype class of the antibody), also referred to as $C_H$ domains. The Fc region, as used herein, preferably includes the "hinge" region of an immunoglobulin, which joins the two heavy (H) chains to each other via disulfide bonds. Alternatively, if the hinge region is not included, then the Fc region is designed with a region that otherwise links the two heavy chains together, since the Axl-Fc protein is produced as a dimer of Axl extracellular domains (e.g., see U.S. Pat. No. 6,323,323 for a generic description of a method for producing dimerized polypeptides).

There are five major H chain classes referred to as isotypes, and accordingly, an Fc protein used in the present invention may be derived from any one of these five classes. The five classes include immunoglobulin M (IgM or μ), immunoglobulin D (IgD or δ), immunoglobulin G (IgG or γ), immunoglobulin A (IgA or α), and immunoglobulin E (IgE or ε). The distinctive characteristics between such isotypes are defined by the constant domain of the immunoglobulin. Human immunoglobulin molecules comprise nine isotypes, IgM, IgD, IgE, four subclasses of IgG including IgG1 (γ1), IgG2 (γ2), IgG3 (γ3) and IgG4 (γ4), and two subclasses of IgA including IgA1 (α1) and IgA2 (α2). The nucleic acid and amino acid sequences of immunoglobulin proteins and domains, including from all isotypes, are well-known in the art in a variety of vertebrate species. Preferably, the Fc region used in the Axl-Fc protein is from the same animal species as the Axl portion of the protein and most preferably, is from the same animal species as the animal species in which the Axl-Fc protein is to be used in vivo. For example, for use in humans, it is preferred that a human Axl protein and a human Fc protein are fused. However, to the extent that Axl from one species will bind Gas6 from a different species and may be tolerated for use in such species, such cross-use is encompassed by the invention.

Fc regions used in the Axl-Fc proteins of the present invention include any Fc region. Preferred Fc regions include the hinge region and the CH2 and CH3 domains of IgG, and preferably, IgG1, although Fc regions of other immunoglobulins can be used. Preferably, the Fc protein does not interfere with the ability of the Axl-Fc protein to remain soluble and circulate in vivo, and does not interfere with the ability of the Axl portion to bind to its ligand. As discussed above, a suitable Fc protein may or may not include the hinge region of the immunoglobulin, but if not, should be otherwise capable of being linked to another Fc protein so that the Axl portion of the fusion protein can be expressed as a dimer.

The Axl inhibitors useful in the present invention may also be produced using a different fusion partner than the Fc region of an immunoglobulin, and are referred to generally as Axl fusion proteins. Suitable candidates include any protein (any fusion partner) that, when fused to the Axl protein described above, allows the Axl fusion protein to be produced as a dimer, does not interfere with the binding of Axl to its ligand, and allows the Axl fusion protein to have a suitable half-life in vivo to be useful as a therapeutic agent in a method of the invention. In one embodiment, an Axl protein of the invention can be produced as a dimer by expressing two copies of the Axl protein as single peptide chains connected by a linker region (e.g., a linker peptide). A variety of peptide linkers suitable for dimerizing two protein monomers are well known in the art.

In one embodiment, a suitable fusion partner candidate does not interfere with the binding of Axl to its ligand, and/or does not necessarily allow the Axl fusion protein to be produced as a dimer. In another embodiment, Axl inhibitors can include fusion partners that improve the stability of the fusion protein, including, but not limited to, e.g., human serum albumin or the C-terminal sequence of the chorionic gonadotropin beta subunit. Other suitable fusion partners for stabilizing a protein will be known to those of skill in the art.

A fusion (or chimeric) protein comprising an Axl protein and an Fc protein (or other suitable fusion partner) as described above is typically and preferably produced or constructed using recombinant technology, although the proteins can also be produced separately and then joined after expression using chemical conjugation. Fusion proteins suitable for use in the invention comprise a suitable Axl protein of the invention (described above) operatively linked to a heterologous protein or polypeptide (i.e., having an amino acid sequence not substantially homologous to the Axl polypeptide), which is a fusion segment or fusion partner (e.g., an Fc protein). "Operatively linked" indicates that the Axl protein and the heterologous fusion partner are fused in-frame. The fusion partner can be fused to the N-terminus or C-terminus of the Axl protein. Fusion proteins can be produced by standard recombinant DNA techniques well known in the art. Preferred fusion partners according to the present invention include, but are not limited to, any proteins or peptides that can: enhance a protein's stability; allow the Axl protein to be produced as a dimer; and/or assist with the purification of a protein (e.g., by affinity chromatography), or in some embodiments, provide another protein function. A suitable heterologous fusion partner can be a domain of any size that has the desired function. Preferably, the fusion partner is an Fc protein.

Axl-Fc proteins that have been produced and accordingly exemplify the invention include: an Fc region consisting of a hinge region, $C_{H1}$ and $C_{H2}$ domain, fused to: (1) an Axl protein selected from positions 1 to 445 of human Axl (SEQ ID NO:2) (also referred to herein as AxlFc); (2) to positions 1 to 325 of human Axl (also referred to herein as Axl IgNF1/Fc); or (3) to positions 1 to 225 of human Axl (also referred to herein as AxlIgFc or AxlIg/Fc).

The present inventors have shown that two Axl-Fc inhibitors of the invention directly bind Gas6 (FIG. 2 and FIG. 7C), thereby inhibiting activation and signaling of full-length Axl (FIG. 3). Gas6 is also a ligand for Mer and Tyro-3, although Axl binds to Gas6 with a higher affinity than either of Mer or Tyro-3. Without being bound by theory, the present inventors believe that Axl-Fc inhibitors of the invention may also bind to (or can be designed to bind to) and inhibit the biological activities associated with Protein S, a cofactor for anticoagulant Protein C, which is a known ligand of Tyro-3 and Mer. Accordingly, the Axl-Fc inhibitor of the invention provides a mechanism of directly regulating (including upregulating or downregulating) the numerous functions of the Mer, Axl and Tyro-3 ligands, including promoting platelet adhesion and clot stability, stimulating cell proliferation, inducing cell adhesion and chemotaxis, and preventing apoptosis. Indeed, the present inventors have demonstrated that the Axl-Fc inhibitor of the invention is superior to Mer-Fc and Tyro-Fc (Fc inhibitors using the other TAM receptors) at inhibiting platelet aggregation. The Axl-Fc inhibitor of the invention also provides a mechanism to indirectly modulate (regulate, modify) the activities of the Mer, Axl and Tyro-3 tyrosine kinases by modulating the functions of their ligands.

Furthermore, the present inventors have shown that Mer is activated (p-Mer) in cells by Axl-Fc inhibitors of the invention (fusions comprising the full-length extracellular domain of Axl) in the absence of added Gas6 ligand. However, AxlIg/Fc, which does not include the FNIII domains of Axl, does not activate Mer. Therefore, the inventors have discovered a preferred Axl inhibitor that sequesters Gas6 and thereby inhibits ligand-mediated activation of both Axl and Mer, but does not activate Mer itself. Accordingly, preferred Axl fusion proteins of the invention include less than the full-length extracellular domain of Axl, and specifically, do not activate Mer, while retaining the ability to sequester Gas6 ligand.

Accordingly, general embodiments of the present invention described in more detail below pertain to any isolated polypeptides described herein, including various portions of full-length Axl, and including those expressed by nucleic acids encoding Axl or a portion or variant thereof.

As used herein, reference to an isolated protein or polypeptide in the present invention, including an isolated Axl protein, includes full-length proteins, fusion proteins, or any fragment or other homologue (variant) of such a protein. The amino acid sequence for Axl from several vertebrate species, including human, are described herein as exemplary Axl proteins (see above). Reference to a Axl protein can include, but is not limited to, purified Axl protein, recombinantly produced Axl protein, membrane bound Axl protein, Axl protein complexed with lipids, soluble Axl protein, an Axl fusion protein, a biologically active homologue of an Axl protein, and an isolated Axl protein associated with other proteins. More specifically, an isolated protein, such as an Axl protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. The term "polypeptide" refers to a polymer of amino acids, and not to a specific length; thus, peptides, oligopeptides and proteins are included within the definition of a polypeptide. As used herein, a polypeptide is said to be "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell (e.g., in a "fusion protein") and still be "isolated" or "purified."

In addition, and by way of example, a "human Axl protein" refers to a Axl protein (generally including a homologue of a naturally occurring Axl protein) from a human (*Homo sapiens*) or to a Axl protein that has been otherwise produced from the knowledge of the structure (e.g., sequence) and perhaps the function of a naturally occurring Axl protein from *Homo sapiens*. In other words, a human Axl protein includes any Axl protein that has substantially similar structure and function of a naturally occurring Axl protein from *Homo sapiens* or that is a biologically active (i.e., has biological activity) homologue of a naturally occurring Axl protein from Homo sapiens as described in detail herein. As such, a human Axl protein can include purified, partially purified, recombinant, mutated/modified and synthetic proteins. According to the present invention, the terms "modification" and "mutation" can be used interchangeably, particularly with regard to the modifications/mutations to the amino acid sequence of Axl (or nucleic acid sequences) described herein. An isolated protein useful as an antagonist or agonist according to the present invention can be isolated from its natural source, produced recombinantly or produced synthetically.

The polypeptides of the invention also encompass fragment and sequence variants, generally referred to herein as homologues. As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. A homologue of a human Axl protein can include a non-human Axl protein (i.e., an Axl protein from a different species).

Variants or homologues include a substantially homologous polypeptide encoded by the same genetic locus in an organism, i.e., an allelic variant, as well as other splicing variants. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

The terms variant or homologue may also encompass polypeptides derived from other genetic loci in an organism, but having substantial homology to any of the previously defined soluble forms of the extracellular Axl receptor tyrosine kinase, or polymorphic variants thereof. Variants also include polypeptides substantially homologous or identical to these polypeptides but derived from another organism. Variants also include polypeptides that are substantially homologous or identical to these polypeptides that are produced by chemical synthesis.

In one embodiment, a Axl homologue comprises, consists essentially of, or consists of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 95% identical, or at least about 95% identical, or at least about 96% identical, or at least about 97% identical, or at least about 98% identical, or at least about 99% identical (or any percent identity between 45% and 99%, in whole integer increments), to a naturally occurring Axl amino acid sequence or to any of the extracellular fragments of a naturally occurring Axl amino acid sequence as described herein. A homologue of Axl differs from a reference (e.g., wild-type) Axl protein and therefore is less than 100% identical to the reference Axl at the amino acid level.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

In one embodiment of the present invention, any of the amino acid sequences described herein, including homologues of such sequences (e.g., Axl extracellular domains), can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The invention is primarily directed to the use of fragments of full-length Axl proteins of the invention. The invention also encompasses fragments of the variants of the polypeptides described herein. As used herein, a fragment comprises at least 6 contiguous amino acids and includes any fragment of a full-length Axl protein described herein, and more preferably includes the entire extracellular domain of Axl or any portion thereof that retains the ability to bind to a Axl ligand (described in detail above). Fragments can be discrete (not fused to other amino acids or polypeptides) or can be within a larger polypeptide (as in a fusion protein of the present invention). Therefore, fragments can include any size fragment between about 6 amino acids and one amino acid less than the full length protein, including any fragment in between, in whole integer increments (e.g., 7, 8, 9 . . . 67, 68, 69 . . . 278, 279, 280 . . . amino acids).

As used herein, the phrase "Axl agonist" refers to any compound that is characterized by the ability to agonize (e.g., stimulate, induce, increase, enhance, or mimic) the biological activity of a naturally occurring Axl as described herein, and includes any Axl homologue, binding protein (e.g., an antibody), agent that interacts with Axl or mimics Axl, or any suitable product of drug/compound/peptide design or selection which is characterized by its ability to agonize (e.g., stimulate, induce, increase, enhance) the biological activity of a naturally occurring Axl protein in a manner similar to the natural agonist, Axl.

Similarly, the phrase, "Axl antagonist" refers to any compound which inhibits (e.g., antagonizes, reduces, decreases, blocks, reverses, or alters) the effect of an Axl agonist as described above. More particularly, a Axl antagonist is capable of acting in a manner relative to Axl activity, such that the biological activity of the natural agonist Axl, is decreased in a manner that is antagonistic (e.g., against, a reversal of, contrary to) to the natural action of Axl. Such antagonists can include, but are not limited to, a protein (e.g., soluble Axl, including the Axl-Fc proteins of the invention), peptide, or nucleic acid (including ribozymes, RNAi, aptamers, and antisense), antibodies and antigen binding fragments thereof, or product of drug/compound/peptide design or selection that provides the antagonistic effect.

Homologues of Axl, including peptide and non-peptide agonists and antagonists of Axl (analogues), can be products of drug design or selection and can be produced using various methods known in the art. Such homologues can be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, Molecular Biotechnology: Therapeutic Applications and Strategies, Wiley-Liss, Inc., which is incorporated herein by reference in its entirety.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis. For smaller peptides, chemical synthesis methods may be preferred. For example, such methods include well known chemical procedures, such as solution or solid-phase peptide synthesis, or semi-synthesis in solution beginning with protein fragments coupled through conventional solution methods. Such methods are well known in the art and may be found in general texts and articles in the area such as: Merrifield, 1997, *Methods Enzymol.* 289:3-13; Wade et al., 1993, *Australas Biotechnol.* 3(6): 332-336; Wong et al., 1991, *Experientia* 47(11-12):1123-1129; Carey et al., 1991, *Ciba Found Symp.* 158:187-203; Plaue et al., 1990, *Biologicals* 18(3):147-157; Bodanszky, 1985, *Int. J. Pept. Protein Res.* 25(5):449-474; or H. Dugas and C. Penney, BIOORGANIC CHEMISTRY, (1981) at pages 54-92, all of which are incorporated herein by reference in their entirety. For example, peptides may be synthesized by solid-phase methodology utilizing a commercially available peptide synthesizer and synthesis cycles supplied by the manufacturer. One skilled in the art recognizes that the solid phase synthesis could also be accomplished using the FMOC strategy and a TFA/scavenger cleavage mixture.

The polypeptides (including fusion proteins) of the invention can be purified to homogeneity. It is understood, however, that preparations in which the polypeptide is not purified to homogeneity are useful. The critical feature is that the preparation allows for the desired function of the polypeptide, even in the presence of considerable amounts of other components. Thus, the invention encompasses various degrees of purity. In one embodiment, the language "substantially free of cellular material" includes preparations of the polypeptide having less than about 30% (by dry weight) other proteins (i.e., contaminating protein), less than about 20% other proteins, less than about 10% other proteins, or less than about 5% other proteins.

According to the present invention, an isolated Axl protein, including a biologically active homologue or fragment thereof, has at least one characteristic of biological activity of activity a wild-type, or naturally occurring Axl protein. Biological activity of Axl and methods of determining the same have been described previously herein. A particularly preferred Axl protein for use in the present invention is an Axl protein variant that binds a ligand of Axl. Signaling function is not required for most of the embodiments of the invention and indeed, is not desired in the case of an Axl fusion protein that is an Axl inhibitor as described herein. In one aspect, the Axl protein binds to any ligand of naturally occurring Axl, including Gas6. In one aspect, the Axl protein binds to Protein S. In another aspect, the Axl protein preferentially binds to one Axl ligand as compared to another Axl ligand. In one aspect, the Axl protein does not activate Mer. In one aspect, the Axl protein binds to a TAM receptor, preferably sufficiently to inhibit the activation of the TAM receptor (e.g., such as by blocking or inhibiting the binding of a natural ligand to the TAM receptor and/or inhibiting receptor dimerization, trimerization or formation of any receptor-protein complex). In this aspect, ligand binding by the Axl protein can be retained or not retained. Most preferably, an Axl protein of the invention includes any Axl protein and preferably any Axl fusion protein with improved stability and/or half-life in vivo that is a competitive inhibitor of Axl (e.g., that preferentially binds to an Axl ligand as compared to an endogenous Axl cellular receptor). Such fusion proteins have been described in detail above.

Preferably, an Axl inhibitor of the invention, including an Axl fusion protein (e.g., an Axl-Fc fusion protein), binds to an Axl ligand with an equal or greater affinity as compared to the binding of the ligand to a naturally occurring Axl receptor tyrosine kinase (e.g., an Axl RTK expressed endogenously by a cell). In one embodiment, the Axl fusion protein inhibits the binding of an Axl ligand to a naturally occurring Axl receptor tyrosine kinase (or to a Mer or Tyro-3 receptor tyrosine kinase) and subsequent activation of the Axl RTK. For example, one can measure the Axl RTK activation using a phospho-Axl analysis by Western blot. In one embodiment, binding of an Axl ligand to a naturally occurring Axl receptor tyrosine kinase is inhibited by at least 50%, at least 60%, at least 70%, at least 80%, at least 90%, or greater, using any suitable method of measurement of binding, as compared to an appropriate control.

Axl fusion proteins of the invention can, in some embodiments, be produced as chimeric proteins with additional proteins or moieties (e.g., chemical moieties) that have a second biological activity. For example, Axl fusion proteins, in addition to comprising the Axl protein and fusion partner as described above, may comprise a protein that has a biological activity that is useful in a method of the invention, such as a pro-apoptotic protein, in the case of treating a neoplastic disease. Alternatively, the additional protein portion of the chimera may be a targeting moiety, in order to deliver the Axl fusion protein to a particular in vivo site (a cell, tissue, or organ). Such additional proteins or moieties may be produced recombinantly or post-translationally, by any suitable method of conjugation.

Some embodiments of the present invention include a composition or formulation (e.g., for therapeutic purposes). Such compositions or formulations can include any one or more of the Axl inhibitors described herein, and may additional comprise one or more pharmaceutical carriers or other therapeutic agents.

In one aspect, the Axl inhibitors of the invention can be formulated with a pharmaceutically acceptable carrier (including an excipient, diluent, adjuvant or delivery vehicle). The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Common suitable pharmaceutical carriers are described in "Remington's Pharmaceutical Sciences" by E. W. Martin.

The compositions can be formulated for a particular type or route of delivery, if desired, including for parenteral, transmucosal, (e.g., orally, nasally or transdermally). Parental routes include intravenous, intra-arteriole, intramuscular, intradermal, subcutaneous, intraperitoneal, intraventricular and intracranial administration.

In another embodiment, the therapeutic compound or composition of the invention can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989). To reduce its systemic side effects, this may be a preferred method for introducing the compound.

In yet another embodiment, the therapeutic compound can be delivered in a controlled release system. For example, a polypeptide may be administered using intravenous infusion with a continuous pump, in a polymer matrix such as poly-lactic/glutamic acid (PLGA), a pellet containing a mixture of cholesterol and the anti-amyloid peptide antibody compound (U.S. Pat. No. 5,554,601) implanted subcutaneously, an implantable osmotic pump, a transdermal patch, liposomes, or other modes of administration.

The pharmaceutical compositions of the invention may further comprise a therapeutically effective amount of another agent or therapeutic compound, preferably in respective proportions such as to provide a synergistic effect in the said prevention or treatment. Alternatively, the pharmaceutical compositions of the invention can be administered concurrently with or sequentially with another pharmaceutical composition comprising such other therapeutic agent or compound. A therapeutically effective amount of a pharmaceutical composition of the invention relates generally to the amount needed to achieve a therapeutic objective. For example, inhibitors and compositions of the invention can be formulated with or administered with (concurrently or sequentially), other chemotherapeutic agents or anti-cancer methods, when it is desired to treat a neoplastic disease, or with other anti-thrombotic/anti-clotting agents, when it is desired to treat a cardiovascular or thrombotic disease or condition.

In one embodiment of the invention, an Axl fusion protein inhibitor (e.g., Axl-Fc) can be provided in a composition with or administered with a Mer fusion protein (e.g., Mer-Fc) or a Tyro-3 fusion protein (e.g., Tyro-3-Fc). Mer-Fc proteins are described in detail in PCT Patent Publication No. WO 2006/058202, incorporated herein by reference in its entirety. A preferred Mer-Fc protein does not activate Axl. A preferred Axl-Fc protein does not activate Mer.

Nucleic Acid Molecules Encoding Axl Proteins and Other Proteins of the Invention Another embodiment of the invention relates to an isolated nucleic acid molecule, or complement thereof, encoding any of the Axl proteins, including fragments and homologues thereof, fusion partners, fusion proteins, or other proteins described herein. Isolated nucleic acid molecules of the present invention can be RNA, for example, mRNA, or DNA, such as cDNA and genomic DNA. DNA molecules can be double-stranded or single-stranded; single stranded RNA or DNA can include the coding, or sense, strand or the non-coding, or antisense, strand. The nucleic acid molecule can include all or a portion of the coding sequence of a gene or nucleic acid sequence and can further comprise additional non-coding sequences such as introns and non-coding 3' and 5' sequences (including regulatory sequences, for example).

An "isolated" nucleic acid molecule, as used herein, is one that is separated from nucleic acids that normally flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs, or culture medium when produced by recombinant techniques, or chemical precursors or other chemicals when chemically synthesized. In some instances, the isolated material will form part of a composition (for example, a crude extract containing other substances), buffer system or reagent mix. In other circumstances, the material may be purified to essential homogeneity, for example as determined by PAGE or column chromatography such as HPLC.

The nucleic acid molecule can be fused to other coding or regulatory sequences and still be considered isolated. Thus, recombinant DNA contained in a vector is included in the definition of "isolated" as used herein. Also, isolated nucleic acid molecules include recombinant DNA molecules in heterologous host cells, as well as partially or substantially purified DNA molecules in solution. "Isolated" nucleic acid molecules also encompass in vivo and in vitro RNA transcripts of the DNA molecules of the present invention. An isolated nucleic acid molecule or nucleotide sequence can include a nucleic acid molecule or nucleotide sequence that is synthesized chemically or by recombinant means. Therefore, recombinant DNA contained in a vector is included in the definition of "isolated" as used herein. Also, isolated nucleotide sequences include partially or substantially purified DNA molecules in solution. In vivo and in vitro RNA transcripts of the DNA molecules of the present invention are also encompassed by "isolated" nucleotide sequences. Such isolated nucleotide sequences are useful in the manufacture of the encoded polypeptide, as probes for isolating homologous sequences (e.g., from other mammalian species), for gene mapping (e.g., by in situ hybridization with chromosomes), or for detecting expression of the gene in tissue (e.g., human tissue), such as by Northern blot analysis.

Nucleic acid molecules useful in the invention include variant nucleic acid molecules that are not necessarily found in nature but which encode novel proteins of the invention. Such variants can be naturally occurring, such as in the case of allelic variation or single nucleotide polymorphisms, or non-naturally-occurring, such as those induced by various mutagens and mutagenic processes. Intended variations include, but are not limited to, addition, deletion and substitution of one or more nucleotides that can result in conservative or non-conservative amino acid changes, including additions and deletions. Other alterations of the nucleic acid molecules of the invention can include, for example, labeling, methylation, internucleotide modifications such as uncharged linkages (e.g., methyl phosphonates, phosphotriesters, phosphoamidates, carbamates), charged linkages (e.g., phosphorothioates, phosphorodithioates), pendent moieties (e.g., polypeptides), intercalators (e.g., acridine, psoralen), chelators, alkylators, and modified linkages (e.g., alpha anomeric nucleic acids). Also included are synthetic molecules that mimic nucleic acid molecules in the ability to bind to designated sequences via hydrogen bonding and other chemical interactions. Such molecules include, for example, those in which peptide linkages substitute for phosphate linkages in the backbone of the molecule.

The invention also pertains to nucleic acid molecules that hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). In one embodiment, the invention includes variants described herein which hybridize under high stringency hybridization conditions (e.g., for selective hybridization) to a nucleotide sequence encoding an Axl protein inhibitor of the invention, or the complements thereof.

"Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 70%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1-2.10.16 and pages 6.3.1-6.3.6 in Current Protocols in Molecular Biology (Ausubel, F. M. et al., "Current Protocols in Molecular Biology", John Wiley & Sons, (1998), the entire teachings of which are incorporated by reference herein). Typically, conditions are used such that sequences at least about 60%, at least about 70%, at least about 80%, at least about 90% or at least about 95% or more identical to each other remain hybridized to one another. By varying hybridization conditions from a level of stringency at which no hybridization occurs to a level at which hybridization is first observed, conditions which will allow a given sequence to hybridize (e.g., selectively) with the most similar sequences in the sample can be determined.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Reference herein to "probes" or "primers" is to oligonucleotides that hybridize in a base-specific manner to a complementary strand of nucleic acid molecules. By "base specific manner" is meant that the two sequences must have a degree of nucleotide complementarity sufficient for the primer or probe to hybridize. Accordingly, the primer or probe sequence is not required to be perfectly complementary to the sequence of the template. Non-complementary bases or modified bases can be interspersed into the primer or probe, provided that base substitutions do not substantially inhibit hybridization. The nucleic acid template may also include "non-specific priming sequences" or "nonspecific sequences" to which the primer or probe has varying degrees of complementarity. Such probes and primers include polypeptide nucleic acids, as described in Nielsen et al., Science, 254, 1497-1500 (1991). Typically, a probe or primer comprises a region of nucleotide sequence that hybridizes to at least about 15, typically about 20-25, and more typically about 40, 50, 75, 100, 150, 200, or more, consecutive nucleotides of a nucleic acid molecule.

The nucleic acid molecules of the invention such as those described above can be identified and isolated using standard molecular biology techniques and the sequence information provided herein. For example, nucleic acid molecules can be amplified and isolated by the polymerase chain reaction using synthetic oligonucleotide primers designed based on a nucleotide sequence encoding a soluble form of Axl receptor tyrosine kinase or the complements thereof See generally PCR Technology: Principles and Applications for DNA Amplification (ed. H. A. Erlich, Freeman Press, NY, N.Y., 1992); PCR Protocols. A Guide to Methods and Applications (Eds. Innis, et al., Academic Press, San Diego, Calif., 1990); Mattila et al., Nucleic Acids Res., 19:4967 (1991); Eckert et al., PCR Methods and Applications, 1:17 (1991); PCR (eds. McPherson et al., IRL Press, Oxford); and U.S. Pat. No.

4,683,202. The nucleic acid molecules can be amplified using cDNA, mRNA or genomic DNA as a template, cloned into an appropriate vector and characterized by DNA sequence analysis.

Other suitable amplification methods include the ligase chain reaction (LCR) (see Wu and Wallace, *Genomics,* 4:560 (1989), Landegren et al., *Science,* 241:1077 (1988)), transcription amplification (Kwoh et al., *Proc. Natl. Acad. Sci. USA,* 86:1173 (1989)), and self-sustained sequence replication (Guatelli et al., *Proc. Nat. Acad. Sci.* USA, 87:1874 (1990)) and nucleic acid based sequence amplification (NASBA).

The amplified DNA can be labeled (e.g., with radiolabel or other reporter molecule) and used as a probe for screening a cDNA library derived from human cells, mRNA in zap express, ZIPLOX or other suitable vector. Corresponding clones can be isolated, DNA can obtained following in vivo excision, and the cloned insert can be sequenced in either or both orientations by art recognized methods to identify the correct reading frame encoding a polypeptide of the appropriate molecular weight. For example, the direct analysis of the nucleotide sequence of nucleic acid molecules of the present invention can be accomplished using well-known methods that are commercially available. See, for example, Sambrook et al., Molecular Cloning, A Laboratory Manual (2nd Ed., CSHP, New York 1989); Zyskind et al., Recombinant DNA Laboratory Manual, (Acad. Press, 1988). Using these or similar methods, the polypeptide and the DNA encoding the polypeptide can be isolated, sequenced and further characterized.

Preferably, the nucleotide sequences of the invention can be used to identify and express recombinant polypeptides for analysis, for characterization or for therapeutic use.

Such nucleic acid sequences can be incorporated into host cells and expression vectors that are well known in the art. According to the present invention, a recombinant nucleic acid molecule includes at least one isolated nucleic acid molecule of the present invention that is linked to a heterologous nucleic acid sequence. Such a heterologous nucleic acid sequence is typically a recombinant nucleic acid vector (e.g., a recombinant vector) which is suitable for cloning, sequencing, and/or otherwise manipulating the nucleic acid molecule, such as by expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention. The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. As used herein, the phrase "recombinant nucleic acid molecule" is used primarily to refer to a recombinant vector into which has been ligated the nucleic acid sequence to be cloned, manipulated, transformed into the host cell (i.e., the insert).

The nucleic acid sequence encoding the protein to be produced is inserted into the vector in a manner that operatively links the nucleic acid sequence to regulatory sequences in the vector (e.g., expression control sequences) which enable the transcription and translation of the nucleic acid sequence when the recombinant molecule is introduced into a host cell. According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell into which the recombinant nucleic acid molecule is to be introduced.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with a protein of the present invention or any heterologous signal segment capable of directing the secretion of a protein according to the present invention.

One or more recombinant molecules of the present invention can be used to produce an encoded product of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

Methods of the Invention

The present invention also relates to methods of treatment (prophylactic and/or therapeutic) for Axl-positive cancers, for Mer-positive cancers, and/or for clotting disorders, using the Axl inhibitors described herein.

The method of use of the inhibitors and therapeutic compositions of the present invention preferably provides a benefit to a patient or individual by inhibiting at least one biological activity of Axl or of its related receptors, Mer and/or Tyro-3.

As used herein, "treatment" refers to clinical intervention in an attempt to alter the natural course of the individual or cell being treated, and may be performed either for prophylaxis and/or during the course of clinical pathology. Desirable effects include preventing occurrence or recurrence of disease, alleviation of symptoms, diminishment of any direct or indirect pathological consequences of the disease, preventing metastasis, lowering the rate of disease progression, amelioration or palliation of the disease state, and remission or improved prognosis. Accordingly, a therapeutic benefit is not necessarily a cure for a particular disease or condition, but rather, preferably encompasses a result which most typically includes alleviation of the disease or condition, elimination of the disease or condition, reduction of a symptom associated with the disease or condition, prevention or alleviation of a secondary disease or condition resulting from the occurrence of a primary disease or condition (e.g., metastatic tumor growth resulting from a primary cancer), and/or prevention of the disease or condition.

In the case of cancer, the method of the invention preferably increases the death of tumor cells, decreases the invasive potential of tumor cells, increases the survival of an individual with cancer, and/or increases tumor regression, decreases tumor growth, and/or decreases tumor burden in the individual.

In the case of clotting disorders and/or cardiovascular disease, the method of the invention preferably prevents or reduces clotting, platelet aggregation, and/or secretion response of platelets to known agonists, or any other symptom of thrombosis or any clotting disorder, without causing bleeding side effects.

A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

According to the present invention, the methods and assays disclosed herein are suitable for use in or with regard to an individual that is a member of the Vertebrate class, Mammalia, including, without limitation, primates, livestock and domestic pets (e.g., a companion animal). Most typically, a patient will be a human patient. According to the present invention, the terms "patient", "individual" and "subject" can be used interchangeably, and do not necessarily refer to an animal or person who is ill or sick (i.e., the terms can reference a healthy individual or an individual who is not experiencing any symptoms of a disease or condition).

Diseases and disorders that are characterized by altered (relative to a subject not suffering from the disease or disorder) Axl receptor tyrosine kinases, levels of this protein, and/or biological activity associated with this protein, are treated with therapeutics that antagonize (e.g., reduce or inhibit) the Axl receptor tyrosine kinase or its ligands. The Axl inhibitors of the present invention block the activation of the full length native Axl by binding to Axl ligands including, but necessarily limited to, Gas6. Therefore, an effective amount of an inhibitor of a Gas6 receptor which is provided in the form of the Axl inhibitors described herein may be used as a treatment for diseases and conditions associated with Axl expression, as well as with Tyro-3 expression and/or Mer expression.

Accordingly, the method of the present invention preferably modulates the activity of Axl receptor tyrosine kinases, and specifically those that are naturally expressed by the cells of an individual (including an individual that has an Axl-associated disease or condition). The method of the invention for example, involves contacting a cell, tissue or system of an individual with an Axl inhibitor that modulates one or more of the activities of Axl. The Axl inhibitors act as competitive inhibitors of Axl expressed by cells. Such methods are preferably performed in vivo (e.g., by administering the agent to a subject). As such, the invention provides methods of treating an individual afflicted with a disease or disorder, specifically a clotting disorder or a cancer.

In one embodiment of the invention, modulation of Axl is contemplated to prevent thrombosis or any clotting disorder, preferably without causing bleeding side effects. According to the present invention, "modulation" refers to any type of regulation, including upregulation, stimulation, or enhancement of expression or activity, or downregulation, inhibition, reduction or blocking of expression or activity. Preferably, the method of the present invention specifically inhibits the activity of Axl expressed by platelets. Inhibition is provided by the present invention through the administration of the Axl inhibitor(s) described herein (e.g., Axl-Fc), which bind directly to Axl ligands and competitively inhibit the binding of such ligands to Axl, Mer, or Tyro-3, and therefore inhibit the activity of such receptors. The Axl inhibitor can be administered alone or together with another therapeutic agent, such as another anti-clotting agent. In one embodiment, the Axl inhibitor is administered together with an agent that inhibits the expression or biological activity of Mer. One such agent is a Mer-Fc protein, wherein the Mer-Fc protein does not activate Axl.

Clotting disorders that can be treated by the method of the invention include, but are not limited to, thrombophilia (including inherited traits predisposing an individual to have a higher risk of clotting), thrombosis or thrombo-embolic disorder. Specifically, this method of treatment could be applied to patients on medications (including, but not limited to, estrogens and chemotherapy) which increase the risk of clotting as well as diseases associated with thrombosis (including, but not limited to, cancer, myeloproliferative disorders, autoimmune disorders, cardiac disease, inflammatory disorders, atherosclerosis, hemolytic anemia, nephrosis, and hyperlipidemia). In addition, this method of treatment could be applied to predisposing factors to increased clotting including cardiovascular interventions, surgery, trauma, or pregnancy. Finally, this method of treatment may be appropriate for patients with adverse side effects from other anti-coagulant or anti-platelet therapies, including heparin-induced thrombocytopenia (a severe immune-mediated drug reaction that occurs in 2-5% of patients exposed to heparin.)

Accordingly, the present invention provides for a method of treating an individual who has or is likely to develop a clotting disorder, comprising modulating the level of Gas6 ligand that is available for interaction with an endogenous Axl RTK in the blood. An effective amount of an Axl inhibitor to administer to an individual is any amount that achieves any detectable inhibition of the natural Axl receptor in the patient, or any detectable reduction in at least one symptom of the clotting disorder.

As discussed above, Axl signaling has been shown to favor tumor growth through activation of proliferative and anti-apoptotic signaling pathways, as well as through promotion of angiogenesis and tumor invasiveness. Accordingly, it is another embodiment of the present invention to inhibit Axl activity as part of a therapeutic strategy which selectively targets cancer cells. Any of the above-described methods and agents for treating a clotting disorder can be applied to the treatment of cancers. Inhibition is also provided by the present invention in this embodiment through the administration of the Axl inhibitor(s) described herein (e.g., Axl-Fc), which bind directly to Axl ligands and competitively inhibit the binding of such ligands to Axl, Mer, or Tyro-3, and therefore inhibit the activity of such receptors. The Axl inhibitor can be administered alone or together with another therapeutic agent, such as another anti-clotting agent. In one embodiment, the Axl inhibitor is administered together with an agent that inhibits the expression or biological activity of Mer. One such agent is a Mer-Fc protein, wherein the Mer-Fc protein does not activate Axl.

Cancers that can be treated by the method of the invention include, but are not limited to, lung cancer (including, but not limited, to non-small cell lung cancer), myeloid leukemia, uterine cancer, ovarian cancer, gliomas, melanoma, prostate cancer, breast cancer, gastric cancer, colon cancer, osteosarcoma, renal cell carcinoma, and thyroid cancer. Because Axl-Fc of the present invention acts as a ligand "sink" for Gas6 and other ligands of the TAM family, the composition and method of the invention are useful for the treatment of not only any cancer in which Axl is expressed, but also any cancer in which Mer and/or Tyro-3 are expressed.

In the therapeutic methods of the invention, suitable methods of administering a composition of the present invention to a subject include any route of in vivo administration that is suitable for delivering the composition. The preferred routes of administration will be apparent to those of skill in the art, depending on the type of delivery vehicle used, the target cell population, and the disease or condition experienced by the patient.

A preferred single dose of a protein such as an Axl inhibitor of the invention typically comprises between about 0.01 microgram×kilogram$^{-1}$ and about 10 milligram×kilogram$^{-1}$ body weight of an animal. A more preferred single dose of such an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. Another particularly preferred single dose of an agent comprises between about 0.1 microgram×kilogram$^{-1}$ and about 10 microgram×kilogram$^{-1}$ body weight of an animal, if the agent is delivered parenterally.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

Each publication or patent cited herein is incorporated herein by reference in its entirety.

EXAMPLES

Example 1

The following example demonstrates that Axl-Fc inhibitors of the invention bind to Gas6 and compete with Axl RTK for Gas6 ligand, preventing the activation of the Axl oncogene in cells.

The inventors have produced two Axl-Fc inhibitors. The first, the amino acid sequence of which is represented herein by SEQ ID NO:17, includes the entire Axl extracellular domain (i.e., positions 1 to 445 of SEQ ID NO:2), fused to the human IgG1 Fc domain, including the hinge, CH2 and CH3 regions. This Axl inhibitor is also referred to herein as Axl-Fc or AxlFc. The second Axl-Fc protein encodes the two IgG-like domains (positions 1-225 of SEQ ID NO:2) fused in the same manner to the human IgG1 Fc domain described above. This Axl inhibitor is also referred to herein as Axl Ig/Fc or AxlIgFc. Stable cell lines expressing these chimeric proteins are made in CHO cells. The CHO cells are grown in suspension culture in serum-free, protein-free, medium and the secreted Axl-Fc is purified from the medium using Protein A SEPHAROSE® chromatography.

Axl activation occurs following binding of the Axl receptor to the Gas6 ligand. This interaction causes Axl dimerization and auto-phosphorylation (see FIG. 1). Specifically, FIG. 1 shows activation of Axl assessed by phosphorylation of Axl protein in A549 cells. A549 cells were cultured in medium lacking serum for two hours and then treated with Protein S or Gas6 ligand at the concentrations shown for 10 minutes. 100 or 200 nM Gas6 stimulated robust phosphorylation of Axl in these cells, but activation of Axl by Protein S was not detected in this experiment.

The Gas6 ligand can also bind an Axl-Fc protein, as is demonstrated in pulldown assays (see FIG. 2). Specifically, recombinant mouse Gas6 was incubated with purified human Axl/Fc and resulting complexes were bound to Protein A Sepharose beads, pulled down by centrifugation, and analyzed by Western blot. The results show that Ret tyrosine kinase does not bind to Gas6, and Ret/Fc was used as a negative control for Gas6 binding.

Furthermore, Axl-Fc can successfully compete with Axl receptor for the Gas6 ligand, and the sequestration of Gas6 by Axl-Fc prevents activation of the Axl oncogene on A549 NSCLC cells (see FIG. 3). Specifically, Axl was phosphorylated following treatment with 50 or 100 nM Gas6. Co-addition of excess Axl-Fc completely blocked Axl activation.

Together, these data demonstrate that Axl-Fc is a successful inhibitor and Axl activation in NSCLC and is expected to be capable of blocking the oncogenic activity of Axl.

Example 2

The following example demonstrates that an Axl-Fc inhibitor of the invention inhibits platelet aggregation and prolongs clotting time.

Figure 4:
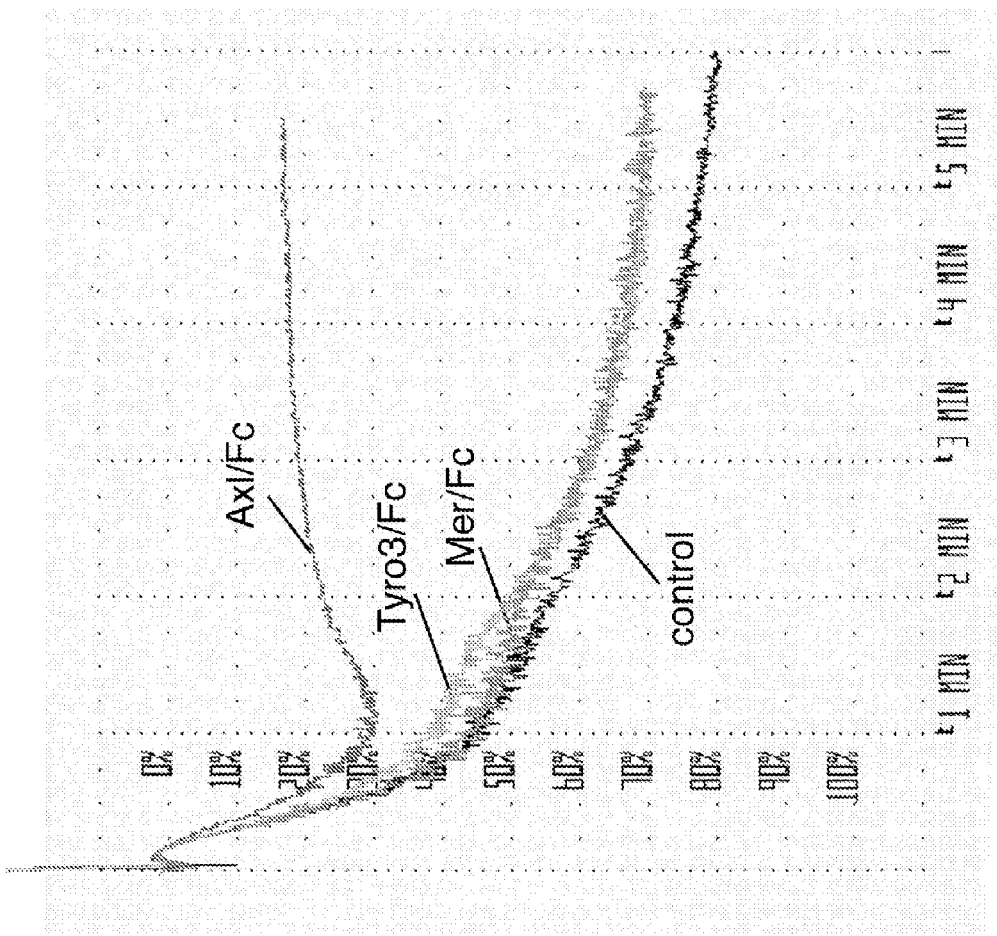
FIG. 4 is a graph showing that Axl-Fc inhibits platelet aggregation significantly better than Mer-Fc, Tyro-Fc, or a negative control.

Referring to FIG. 4, this experiment demonstrates that Axl-Fc is superior to Mer-Fc or Tyro3-Fc in inhibition of platelet aggregation induced by ADP. In vitro platelet aggregation was performed using human platelet rich plasma and was analyzed on a BioData aggregometer. Aggregation response to platelets is depicted in response to 4 micromolar ADP following preincubation with no Mer-Fc or Axl-Fc (i.e., no inhibitor) (black), 650 nM Mer-Fc (red), 650 nM Axl-Fc (blue), or 650 nM Tyro3-FC (green).

Referring to FIG. 5, this experiment demonstrates that Axl-Fc prolongs in vitro clotting time. A PFA-100 Platelet Function Analyzer was used to measure platelet function in response to the agonists collagen/epinephrine or collagen/ADP. Onset of capillary tube closure time (in seconds) due to platelet plug formation is indicated in human whole blood samples pretreated with no inhibitor, or varying concentrations of Axl-Fc.

Example 3

The following example describes the effect on proliferation, survival, and invasiveness in Axl-positive non small cell cancer lung cell lines following inhibition of Axl activity with Axl-Fc.

The Axl-overexpressing A549 non-small cell lung cancer cell is treated with varying concentrations of Axl-Fc (50 -150 nM). Inhibition of Axl activation is detected by western blots by probing for phospho-Axl as shown in FIGS. 1 and 3. Cell proliferation assays are carried out using thymidine incorporation and BrdU incorporation. For the thymidine incorporation experiments, $4 \times 10^3$ cells/well are washed in 96 well plates and serum starved in serum-free cell media and then inhibitors are added at varying concentrations to the cells (1-10 μM) for 24 hours. 1 μCi/well of Methyl-$^3$H thymidine (Amersham Biosciences) are added for 12 hours. Cells are washed with PBS and harvested in cell harvester. Filter membrane incorporated radioactivity is measured in a scintillation beta counter. The results obtained in counts per minute are then calculated as average percent variation with respective controls. Cells without inhibitors grown in similar conditions are used as controls. A cell proliferation ELISA assay (Roche) is used to measure BrdU incorporation. Briefly, cells are cultured in the presence of inhibitors for 24 to 48 hours. BrdU is added to the cells and the cells are reincubated. The culture medium is removed and the cells are fixed/denatured. Anti-BrdU coupled to peroxidase is added and the immune complex is detected using an ELISA reader. For cell survival assays, approximately $5 \times 10^5$ cells are washed twice with PBS and stained propidium iodide and FITC conjugated annexin V (Roche) for 15-30 minutes. The percentage of apoptotic cells are analyzed using a FACScan flow cytometer. Cell invasion assays are performed using 24 well insert based assays (BD Biosciences). Culture inserts are precoated to a density of 30 mcg/insert of Matrigel Basement Membrane Matrix (BD Biosciences) and $2.5 \times 10^4$ A549 cells in media are added to the insert. After 24 hours, cells that have invaded or migrated through the Fluoro-Blok membrane are stained with propidium iodide and fluorescence images are taken and analyzed.

The results of these assays are expected to demonstrate that Axl-Fc inhibits proliferation, survival, and invasiveness of Axl-positive non small cell cancer lung cells.

Example 4

The following example describes the determination of the effect of Axl-Fc treatment on cancer development and overall survival in a NSCLC xenograft mouse model.

Varying concentrations ($10^4$ to $10^7$) of A549 NSCLC cells are injected into the flank or intratracheally into nude mice. Mice are treated with 2.5-10 mg/kg Axl-Fc (or control Ret-Fc) injected I.P. twice per week. Tumors on flank of mice treated with Axl-Fc are compared to controls. Following 21 days of treatment for mice instilled with A549 cells intratracheally for orthotopic tumor model, mice are euthanized and tumor size measured. The orthotopic tumor model will be replicated using a luciferase labeled A549 cell line (Xenogen) and serial imaging is performed in vivo using the IVIS Imaging System 200. The bioluminescence imaging allows analysis of Axl-Fc efficacy over a range of treatment times.

The results of these experiments are expected to demonstrate that Axl-Fc inhibits tumor growth or reduces tumor burden, and/or increases survival of mice with tumors.

Example 5

The following example demonstrates that both AxlFc and AxlIgFc bind to Gas6 ligand.

In this experiment, AxlFc, composed of the entire extracellular domain of Axl fused to Fc domain of human immunoglobulin (IgG) (SEQ ID NO:17), was expressed in HEK293 cells and was detected as a protein of approximately 115 kD when analyzed by Western blot (FIG. 7B). AxlIgFc, composed of only Ig-like motifs in the extracellular domain of Axl (positions 1-225 of SEQ ID NO:2) fused to the Fc domain of human immunoglobulin (IgG), was detected as a protein of approximately 115 kD 65-75 kD (FIG. 7B). Both AxlFc and AxlIgFc, bound Gas6 in a pulldown assay in which AxlFc/Gas6 or AxlIgFc/Gas6 were pulled down with protein G-Sepharose beads (FIG. 7C). Bound Gas6 was detected by immunoblotting for Gas6.

Example 6

The following example demonstrates that Axl Ig/Fc Does Not Activate Mer.

Figure 8:
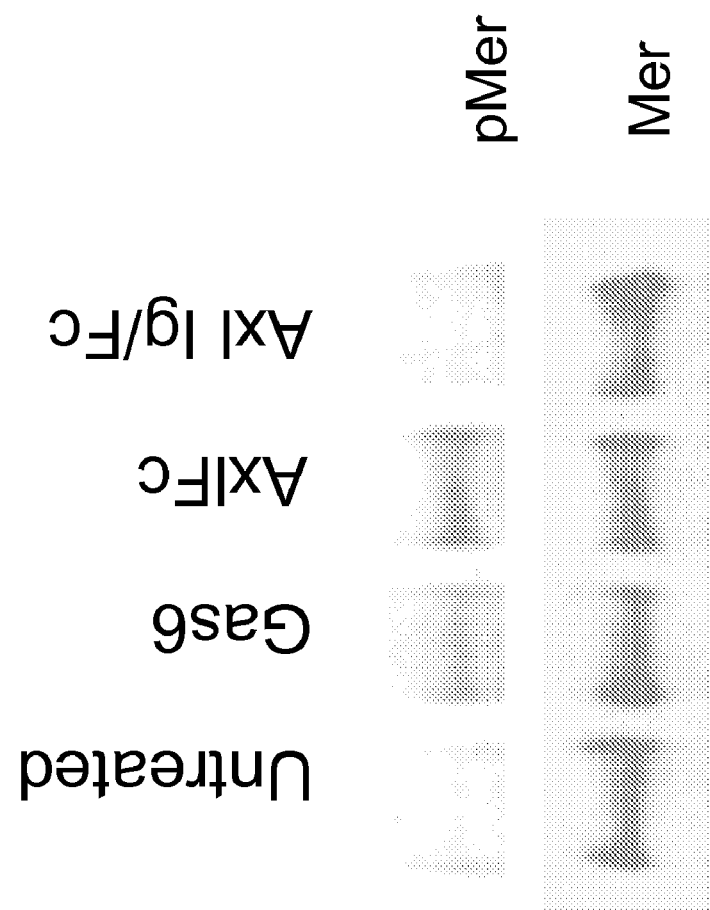
FIG. 8 is a digitized image showing that AxlIgFc does not activate Mer.

In this experiment, the results of which are shown in FIG. 8, Mer is activated (p-Mer) in REH human leukemia cells by addition of AxlFc in the absence of added Gas6 ligand. However, Axl Ig/Fc does not activate Mer in cultured cells. Total Mer is shown as a loading control.

Example 7

The following example demonstrates that Axl Ig/Fc blocks ligand-mediated activation of Axl and Mer.

Figure 9B:
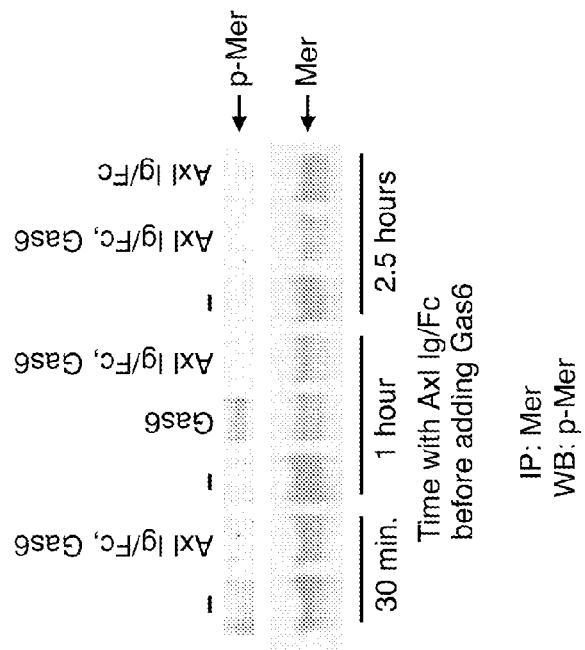
FIG. 9B is a digitized image showing that AxlIgFc blocks ligand-mediated activation of Mer in B cell leukemia 697 cells.
Figure 9A:
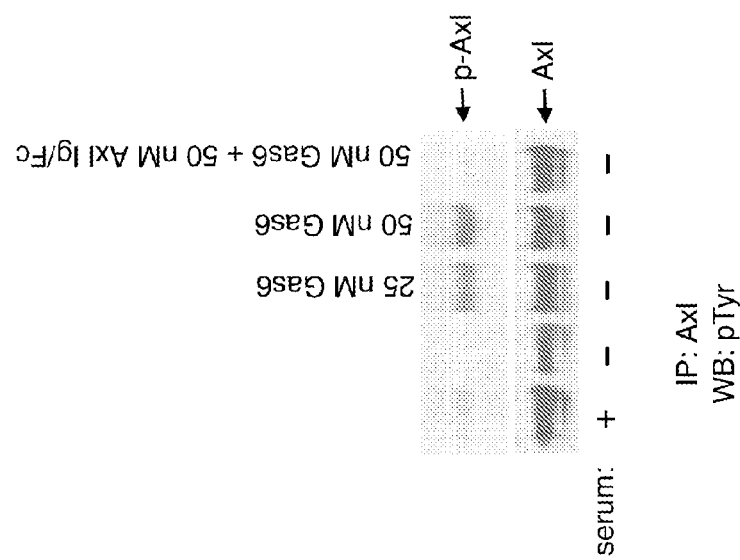
FIG. 9A is a digitized image showing that AxlIgFc blocks ligand-mediated activation of Axl in A172 glioblastoma cells.

Referring to FIG. 9A, phosphorylated Axl (p-Axl) was detected in A172 glioblastoma cells growing in medium containing 10% serum. Starving cells in medium without serum decreased p-Axl. Subsequent stimulation of starved cells with Gas6 activated Axl, but the activation was blocked by simultaneous addition of Axl Ig/Fc. Total Axl is shown as a control for immunoprecipitation efficiency.

Referring to FIG. 9B, Mer in 697 B-cell leukemia cells was activated by addition of Gas6. This activation was inhibited by preincubation of cultures with Axl Ig/Fc for 30 min., 1 hour, or 2.5 hours prior to addition of Gas6. Total Mer is shown as an immunoblotting control.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An Axl fusion protein comprising:
   a) a first protein comprising at least a portion of the extracellular domain of an Axl receptor tyrosine kinase (Axl RTK) that binds to an Axl ligand; and/or at least a portion of the extracellular domain of an Axl receptor tyrosine kinase (Axl RTK) that binds to a receptor selected from the group consisting of Axl, Tyro and Mer and inhibits the binding of a ligand to said receptor or inhibits dimerization, trimerization or formation of any receptor-protein complex of said receptor; and
   b) a second protein that is a heterologous fusion protein, wherein the second protein is fused to the first protein and is at least a portion of the extracellular domain of an Axl receptor tyrosine kinase (Axl RTK) that binds to an Axl ligand.

2. The Axl fusion protein of claim 1, wherein the first and second protein each comprise the entire Axl RTK extracellular domain.

3. The Axl fusion protein of claim 1, wherein the Axl fusion protein does not activate Mer.

4. The Axl fusion protein of claim 1, wherein the fusion protein further comprises a third protein, fused to the first or to the second protein.

5. The Axl fusion protein of claim 4, wherein the third protein is a pro-apoptosis protein.

6. The Axl fusion protein of claim 4, wherein the third protein is an anti-clotting protein.

* * * * *

SEQUENCE LISTING

<160> NUMBER OF SEQ ID NOS: 18

<210> SEQ ID NO 1
<211> LENGTH: 5014
<212> TYPE: DNA
<213> ORGANISM: Homo sapiens
<220> FEATURE:
<221> NAME/KEY: CDS
<222> LOCATION: (459)..(3143)

<400> SEQUENCE: 1

```
gagtggagtt ctggaggaat gtttaccaga cacagagccc agagggacag cgcccagagc    60
ccagatagag agacacggcc tcactggctc agcaccaggg tccccttccc cctcctcagc   120
tccctccctg gcccctttaa gaaagagctg atcctctcct ctcttgagtt aaccctgat    180 tgtccaggtg gcccctggct ctggcctggt gggcggaggc aaaggggag ccaggggcgg   240 agaaagggtt gcccaagtct gggagtgagg aaggaggca ggggtgctga aaggcggct    300 gctgggcaga gccggtggca agggcctccc ctgccgctgt gccaggcagg cagtgccaaa   360
tccggggagc ctggagctgg ggggaggggcc gggacagcc cggccctgcc ccctccccg    420 ctgggagccc agcaacttct gaggaaagtt tggcaccc atg gcg tgg cgg tgc ccc   476
                                        Met Ala Trp Arg Cys Pro
                                          1               5 agg atg ggc agg gtc ccg ctg gcc tgg tgc ttg gcg ctg tgc ggc tgg    524
Arg Met Gly Arg Val Pro Leu Ala Trp Cys Leu Ala Leu Cys Gly Trp
            10                  15                  20 gcg tgc atg gcc ccc agg ggc acg cag gct gaa gaa agt ccc ttc gtg    572
Ala Cys Met Ala Pro Arg Gly Thr Gln Ala Glu Glu Ser Pro Phe Val
        25                  30                  35 ggc aac cca ggg aat atc aca ggt gcc cgg gga ctc acg ggc acc ctt    620
Gly Asn Pro Gly Asn Ile Thr Gly Ala Arg Gly Leu Thr Gly Thr Leu
    40                  45                  50 cgg tgt cag ctc cag gtt cag gga gag ccc ccc gag gta cat tgg ctt    668
Arg Cys Gln Leu Gln Val Gln Gly Glu Pro Pro Glu Val His Trp Leu
55                  60                  65                  70 cgg gat gga cag atc ctg gag ctc gcg gac agc acc cag acc cag gtg    716
Arg Asp Gly Gln Ile Leu Glu Leu Ala Asp Ser Thr Gln Thr Gln Val
                75                  80                  85 ccc ctg ggt gag gat gaa cag gat gac tgg ata gtg gtc agc cag ctc    764
Pro Leu Gly Glu Asp Glu Gln Asp Asp Trp Ile Val Val Ser Gln Leu
            90                  95                 100 aga atc acc tcc ctg cag ctt tcc gac acg gga cag tac cag tgt ttg    812
Arg Ile Thr Ser Leu Gln Leu Ser Asp Thr Gly Gln Tyr Gln Cys Leu
        105                 110                 115 gtg ttt ctg gga cat cag acc ttc gtg tcc cag cct ggc tat gtt ggg    860
Val Phe Leu Gly His Gln Thr Phe Val Ser Gln Pro Gly Tyr Val Gly
    120                 125                 130 ctg gag ggc ttg cct tac ttc ctg gag gag ccc gaa gac agg act gtg    908
Leu Glu Gly Leu Pro Tyr Phe Leu Glu Glu Pro Glu Asp Arg Thr Val
135                 140                 145                 150 gcc gcc aac acc ccc ttc aac ctg agc tgc caa gct cag gga ccc cca    956
Ala Ala Asn Thr Pro Phe Asn Leu Ser Cys Gln Ala Gln Gly Pro Pro
                155                 160                 165 gag ccc gtg gac cta ctc tgg ctc cag gat gct gtc ccc ctg gcc acg   1004
Glu Pro Val Asp Leu Leu Trp Leu Gln Asp Ala Val Pro Leu Ala Thr
            170                 175                 180 gct cca ggt cac ggc ccc cag cgc agc ctg cat gtt cca ggg ctg aac   1052
Ala Pro Gly His Gly Pro Gln Arg Ser Leu His Val Pro Gly Leu Asn
        185                 190                 195
```

```
aag aca tcc tct ttc tcc tgc gaa gcc cat aac gcc aag ggg gtc acc    1100
Lys Thr Ser Ser Phe Ser Cys Glu Ala His Asn Ala Lys Gly Val Thr
    200                 205                 210 aca tcc cgc aca gcc acc atc aca gtg ctc ccc cag cag ccc cgt aac    1148
Thr Ser Arg Thr Ala Thr Ile Thr Val Leu Pro Gln Gln Pro Arg Asn
215                 220                 225                 230 ctc cac ctg gtc tcc cgc caa ccc acg gag ctg gag gtg gct tgg act    1196
Leu His Leu Val Ser Arg Gln Pro Thr Glu Leu Glu Val Ala Trp Thr
                235                 240                 245 cca ggc ctg agc ggc atc tac ccc ctg acc cac tgc acc ctg cag gct    1244
Pro Gly Leu Ser Gly Ile Tyr Pro Leu Thr His Cys Thr Leu Gln Ala
            250                 255                 260 gtg ctg tca gac gat ggg atg ggc atc cag gcg gga gaa cca gac ccc    1292
Val Leu Ser Asp Asp Gly Met Gly Ile Gln Ala Gly Glu Pro Asp Pro
        265                 270                 275 cca gag gag ccc ctc acc tcg caa gca tcc gtg ccc ccc cat cag ctt    1340
Pro Glu Glu Pro Leu Thr Ser Gln Ala Ser Val Pro Pro His Gln Leu
    280                 285                 290 cgg cta ggc agc ctc cat cct cac acc cct tat cac atc cgc gtg gca    1388
Arg Leu Gly Ser Leu His Pro His Thr Pro Tyr His Ile Arg Val Ala
295                 300                 305                 310 tgc acc agc agc cag ggc ccc tca tcc tgg acc cac tgg ctt cct gtg    1436
Cys Thr Ser Ser Gln Gly Pro Ser Ser Trp Thr His Trp Leu Pro Val
                315                 320                 325 gag acg ccg gag gga gtg ccc ctg ggc ccc cct gag aac att agt gct    1484
Glu Thr Pro Glu Gly Val Pro Leu Gly Pro Pro Glu Asn Ile Ser Ala
            330                 335                 340 acg cgg aat ggg agc cag gcc ttc gtg cat tgg caa gag ccc cgg gcg    1532
Thr Arg Asn Gly Ser Gln Ala Phe Val His Trp Gln Glu Pro Arg Ala
        345                 350                 355 ccc ctg cag ggt acc ctg tta ggg tac cgg ctg gcg tat caa ggc cag    1580
Pro Leu Gln Gly Thr Leu Leu Gly Tyr Arg Leu Ala Tyr Gln Gly Gln
    360                 365                 370 gac acc cca gag gtg cta atg gac ata ggg cta agg caa gag gtg acc    1628
Asp Thr Pro Glu Val Leu Met Asp Ile Gly Leu Arg Gln Glu Val Thr
375                 380                 385                 390 ctg gag ctg cag ggg gac ggg tct gtg tcc aat ctg aca gtg tgt gtg    1676
Leu Glu Leu Gln Gly Asp Gly Ser Val Ser Asn Leu Thr Val Cys Val
                395                 400                 405 gca gcc tac act gct gct ggg gat gga ccc tgg agc ctc cca gta ccc    1724
Ala Ala Tyr Thr Ala Ala Gly Asp Gly Pro Trp Ser Leu Pro Val Pro
            410                 415                 420 ctg gag gcc tgg cgc cca ggg caa gca cag cca gtc cac cag ctg gtg    1772
Leu Glu Ala Trp Arg Pro Gly Gln Ala Gln Pro Val His Gln Leu Val
        425                 430                 435 aag gaa cct tca act cct gcc ttc tcg tgg ccc tgg tgg tat gta ctg    1820
Lys Glu Pro Ser Thr Pro Ala Phe Ser Trp Pro Trp Trp Tyr Val Leu
    440                 445                 450 cta gga gca gtc gtg gcc gct gcc tgt gtc ctc atc ttg gct ctc ttc    1868
Leu Gly Ala Val Val Ala Ala Ala Cys Val Leu Ile Leu Ala Leu Phe
455                 460                 465                 470 ctt gtc cac cgg cga aag aag gag acc cgt tat gga gaa gtg ttt gaa    1916
Leu Val His Arg Arg Lys Lys Glu Thr Arg Tyr Gly Glu Val Phe Glu
                475                 480                 485 cca aca gtg gaa aga ggt gaa ctg gta gtc agg tac cgc gtg cgc aag    1964
Pro Thr Val Glu Arg Gly Glu Leu Val Val Arg Tyr Arg Val Arg Lys
            490                 495                 500 tcc tac agt cgt cgg acc act gaa gct acc ttg aac agc ctg ggc atc    2012
Ser Tyr Ser Arg Arg Thr Thr Glu Ala Thr Leu Asn Ser Leu Gly Ile
        505                 510                 515
```

```
agt gaa gag ctg aag gag aag ctg cgg gat gtg atg gtg gac cgg cac        2060
Ser Glu Glu Leu Lys Glu Lys Leu Arg Asp Val Met Val Asp Arg His
    520             525                 530 aag gtg gcc ctg ggg aag act ctg gga gag gga gag ttt gga gct gtg        2108
Lys Val Ala Leu Gly Lys Thr Leu Gly Glu Gly Glu Phe Gly Ala Val
535             540                 545                 550 atg gaa ggc cag ctc aac cag gac gac tcc atc ctc aag gtg gct gtg        2156
Met Glu Gly Gln Leu Asn Gln Asp Asp Ser Ile Leu Lys Val Ala Val
                555                 560                 565 aag acg atg aag att gcc atc tgc acg agg tca gag ctg gag gat ttc        2204
Lys Thr Met Lys Ile Ala Ile Cys Thr Arg Ser Glu Leu Glu Asp Phe
            570                 575                 580 ctg agt gaa gcg gtc tgc atg aag gaa ttt gac cat ccc aac gtc atg        2252
Leu Ser Glu Ala Val Cys Met Lys Glu Phe Asp His Pro Asn Val Met
585             590                 595 agg ctc atc ggt gtc tgt ttc cag ggt tct gaa cga gag agc ttc cca        2300
Arg Leu Ile Gly Val Cys Phe Gln Gly Ser Glu Arg Glu Ser Phe Pro
        600                 605                 610 gca cct gtg gtc atc tta cct ttc atg aaa cat gga gac cta cac agc        2348
Ala Pro Val Val Ile Leu Pro Phe Met Lys His Gly Asp Leu His Ser
615             620                 625                 630 ttc ctc ctc tat tcc cgg ctc ggg gac cag cca gtg tac ctg ccc act        2396
Phe Leu Leu Tyr Ser Arg Leu Gly Asp Gln Pro Val Tyr Leu Pro Thr
                635                 640                 645 cag atg cta gtg aag ttc atg gca gac atc gcc agt ggc atg gag tat        2444
Gln Met Leu Val Lys Phe Met Ala Asp Ile Ala Ser Gly Met Glu Tyr
            650                 655                 660 ctg agt acc aag aga ttc ata cac cgg gac ctg gcg gcc agg aac tgc        2492
Leu Ser Thr Lys Arg Phe Ile His Arg Asp Leu Ala Ala Arg Asn Cys
665             670                 675 atg ctg aat gag aac atg tcc gtg tgt gtg gcg gac ttc ggg ctc tcc        2540
Met Leu Asn Glu Asn Met Ser Val Cys Val Ala Asp Phe Gly Leu Ser
        680                 685                 690 aag aag atc tac aat ggg gac tac tac cgc cag gga cgt atc gcc aag        2588
Lys Lys Ile Tyr Asn Gly Asp Tyr Tyr Arg Gln Gly Arg Ile Ala Lys
695             700                 705                 710 atg cca gtc aag tgg att gcc att gag agt cta gct gac cgt gtc tac        2636
Met Pro Val Lys Trp Ile Ala Ile Glu Ser Leu Ala Asp Arg Val Tyr
                715                 720                 725 acc agc aag agc gat gtg tgg tcc ttc ggg gtg aca atg tgg gag att        2684
Thr Ser Lys Ser Asp Val Trp Ser Phe Gly Val Thr Met Trp Glu Ile
            730                 735                 740 gcc aca aga ggc caa acc cca tat ccg ggc gtg gag aac agc gag att        2732
Ala Thr Arg Gly Gln Thr Pro Tyr Pro Gly Val Glu Asn Ser Glu Ile
745             750                 755 tat gac tat ctg cgc cag gga aat cgc ctg aag cag cct gcg gac tgt        2780
Tyr Asp Tyr Leu Arg Gln Gly Asn Arg Leu Lys Gln Pro Ala Asp Cys
        760                 765                 770 ctg gat gga ctg tat gcc ttg atg tcg cgg tgc tgg gag cta aat ccc        2828
Leu Asp Gly Leu Tyr Ala Leu Met Ser Arg Cys Trp Glu Leu Asn Pro
775             780                 785                 790 cag gac cgg cca agt ttt aca gag ctg cgg gaa gat ttg gag aac aca        2876
Gln Asp Arg Pro Ser Phe Thr Glu Leu Arg Glu Asp Leu Glu Asn Thr
                795                 800                 805 ctg aag gcc ttg cct cct gcc cag gag cct gac gaa atc ctc tat gtc        2924
Leu Lys Ala Leu Pro Pro Ala Gln Glu Pro Asp Glu Ile Leu Tyr Val
            810                 815                 820 aac atg gat gag ggt gga ggt tat cct gaa ccc cct gga gct gca gga        2972
Asn Met Asp Glu Gly Gly Gly Tyr Pro Glu Pro Pro Gly Ala Ala Gly
825                 830                 835
```

```
gga gct gac ccc cca acc cag cca gac cct aag gat tcc tgt agc tgc    3020
Gly Ala Asp Pro Pro Thr Gln Pro Asp Pro Lys Asp Ser Cys Ser Cys
        840                 845                 850 ctc act gcg gct gag gtc cat cct gct gga cgc tat gtc ctc tgc cct    3068
Leu Thr Ala Ala Glu Val His Pro Ala Gly Arg Tyr Val Leu Cys Pro
855                 860                 865                 870 tcc aca acc cct agc ccc gct cag cct gct gat agg ggc tcc cca gca    3116
Ser Thr Thr Pro Ser Pro Ala Gln Pro Ala Asp Arg Gly Ser Pro Ala
                875                 880                 885 gcc cca ggg cag gag gat ggt gcc tga gacaaccctc cacctggtac          3163
Ala Pro Gly Gln Glu Asp Gly Ala
                890 tccctctcag gatccaagct aagcactgcc actggggaaa actccacctt cccactttcc  3223 caccccacgc cttatcccca cttgcagccc tgtcttccta cctatcccac ctccatccca  3283 gacaggtccc tccccttctc tgtgcagtag catcaccttg aaagcagtag catcaccatc  3343 tgtaaaagga aggggttgga ttgcaatatc tgaagccctc ccaggtgtta acattccaag  3403 actctagagt ccaaggttta aagagtctag attcaaaggt tctaggtttc aaagatgctg  3463 tgagtctttg gttctaagga cctgaaattc caaagtctct aattctatta aagtgctaag  3523 gttctaaggc ctactttttt ttttttttt ttttttttt tttttttgc gatagagtct    3583 cactgtgtca cccaggctgg agtgcagtgg tgcaatctcg cctcactgca accttcacct  3643 accgagttca agtgattttc ctgccttggc ctcccaagta gctgggatta caggtgtgtg  3703 ccaccacacc cggctaattt ttatattttt agtagagaca gggtttcacc atgttggcca  3763 ggctggtcta aaactcctga cctcaagtga tctgcccacc tcagcctccc aaagtgctga  3823 gattacaggc atgagccact gcactcaacc ttaagaccta ctgttctaaa gctctgacat  3883 tatgtggttt tagattttct ggttctaaca ttttgataa agcctcaagg ttttaggttc   3943 taaagttcta agattctgat tttaggagct aaggctctat gagtctagat gtttattctt  4003 ctagagttca gagtccttaa aatgtaagat tatagattct aaagattcta tagttctaga  4063 catggaggtt ctaaggccta ggattctaaa atgtgatgtt ctaaggctct gagagtctag  4123 attctctggc tgtaaggctc tagatcataa ggcttcaaaa tgttatcttc tcaagttcta  4183 agattctaat gatgatcaat tatagttttct gaggctttat gataatagat tctcttgtat  4243 aagatcctag atcctaaggg tcgaaagctc tagaatctgc aattcaaaag ttccaagagt  4303 ctaaagatgg agtttctaag gtccggtgtt ctaagatgtg atattctaag acttactcta  4363 agatcttaga ttctctgtgt ctaagattct agatcagatg ctccaagatt ctagatgatt  4423 aaataagatt ctaacggtct gttctgtttc aaggcactct agattccatt ggtccaagat  4483 tccggatcct aagcatctaa gttataagac tctcacactc agttgtgact aactagacac  4543 caaagttcta ataatttcta atgttggaca cctttaggtt ctttgctgca ttctgcctct  4603 ctaggaccat ggttaagagt ccaagaatcc acatttctaa aatcttatag ttctaggcac  4663 tgtagttcta agactcaaat gttctaagtt tctaagattc taaaggtcca caggtctaga  4723 ctattaggtg caatttcaag gttctaaccc tatactgtag tattctttgg ggtgcccctc  4783 tccttcttag ctatcattgc ttcctcctcc ccaactgtgg gggtgtgccc ccttcaagcc  4843 tgtgcaatgc attagggatg cctccttttcc cgcagggat ggacgatctc ccacctttcg   4903 ggccatgttg ccccccgtgag ccaatccctc accttctgag tacagagtgt ggactctggt  4963 gcctccagag gggctcaggt cacataaaac tttgtatatc aacgaaaaaa a           5014
```

```
<210> SEQ ID NO 2
<211> LENGTH: 894
<212> TYPE: PRT
<213> ORGANISM: Homo sapiens

<400> SEQUENCE: 2

Met Ala Trp Arg Cys Pro Arg Met Gly Arg Val Pro Leu Ala Trp Cys
 1               5                  10                  15

Leu Ala Leu Cys Gly Trp Ala Cys Met Ala Pro Arg Gly Thr Gln Ala
             20                  25                  30

Glu Glu Ser Pro Phe Val Gly Asn Pro Gly Asn Ile Thr Gly Ala Arg
         35                  40                  45

Gly Leu Thr Gly Thr Leu Arg Cys Gln Leu Gln Val Gln Gly Glu Pro
     50                  55                  60

Pro Glu Val His Trp Leu Arg Asp Gly Gln Ile Leu Glu Leu Ala Asp
 65                  70                  75                  80

Ser Thr Gln Thr Gln Val Pro Leu Gly Glu Asp Glu Gln Asp Asp Trp
                 85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
    370                 375                 380

Leu Arg Gln Glu Val Thr Leu Glu Leu Gln Gly Asp Gly Ser Val Ser
```

-continued

```
             385                 390                 395                 400
Asn Leu Thr Val Cys Val Ala Ala Tyr Thr Ala Ala Gly Asp Gly Pro
                    405                 410                 415

Trp Ser Leu Pro Val Pro Leu Glu Ala Trp Arg Pro Gly Gln Ala Gln
                    420                 425                 430

Pro Val His Gln Leu Val Lys Glu Pro Ser Thr Pro Ala Phe Ser Trp
                    435                 440                 445

Pro Trp Trp Tyr Val Leu Leu Gly Ala Val Ala Ala Ala Cys Val
            450                 455                 460

Leu Ile Leu Ala Leu Phe Leu Val His Arg Arg Lys Lys Glu Thr Arg
465                 470                 475                 480

Tyr Gly Glu Val Phe Glu Pro Thr Val Glu Arg Gly Glu Leu Val Val
                    485                 490                 495

Arg Tyr Arg Val Arg Lys Ser Tyr Ser Arg Arg Thr Thr Glu Ala Thr
                    500                 505                 510

Leu Asn Ser Leu Gly Ile Ser Glu Glu Leu Lys Glu Lys Leu Arg Asp
                515                 520                 525

Val Met Val Asp Arg His Lys Val Ala Leu Gly Lys Thr Leu Gly Glu
        530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                    565                 570                 575

Ser Glu Leu Glu Asp Phe Leu Ser Glu Ala Val Cys Met Lys Glu Phe
                580                 585                 590

Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
        610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                    645                 650                 655

Ala Ser Gly Met Glu Tyr Leu Ser Thr Lys Arg Phe Ile His Arg Asp
                660                 665                 670

Leu Ala Ala Arg Asn Cys Met Leu Asn Glu Asn Met Ser Val Cys Val
            675                 680                 685

Ala Asp Phe Gly Leu Ser Lys Lys Ile Tyr Asn Gly Asp Tyr Tyr Arg
        690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                    725                 730                 735

Val Thr Met Trp Glu Ile Ala Thr Arg Gly Gln Thr Pro Tyr Pro Gly
                740                 745                 750

Val Glu Asn Ser Glu Ile Tyr Asp Tyr Leu Arg Gln Gly Asn Arg Leu
            755                 760                 765

Lys Gln Pro Ala Asp Cys Leu Asp Gly Leu Tyr Ala Leu Met Ser Arg
        770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                    805                 810                 815
```

```
Asp Glu Ile Leu Tyr Val Asn Met Asp Glu Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 3
<211> LENGTH: 4987
<212> TYPE: DNA
<213> ORGANISM: Homo sapiens
<220> FEATURE:
<221> NAME/KEY: CDS
<222> LOCATION: (459)..(3116)

<400> SEQUENCE: 3
gagtggagtt ctggaggaat gtttaccaga cacagagccc agagggacag cgcccagagc      60
ccagatagag agacacggcc tcactggctc agcaccaggg tccccttccc cctcctcagc     120
tccctccctg gccccttaa gaaagagctg atcctctcct ctcttgagtt aaccctgat      180 tgtccaggtg gccctggct ctggcctggt gggcggaggc aaaggggag ccagggcgg       240 agaaagggtt gcccaagtct gggagtgagg aaggaggca gggtgctga aaggcggct       300 gctgggcaga gccggtggca agggcctccc ctgccgctgt gccaggcagg cagtgccaaa    360
tccggggagc ctggagctgg ggggagggcc gggacagcc cggccctgcc ccctccccg      420 ctgggagccc agcaacttct gaggaaagtt tggcaccc atg gcg tgg cgg tgc ccc   476
                                         Met Ala Trp Arg Cys Pro
                                           1               5 agg atg ggc agg gtc ccg ctg gcc tgg tgc ttg gcg ctg tgc ggc tgg    524
Arg Met Gly Arg Val Pro Leu Ala Trp Cys Leu Ala Leu Cys Gly Trp
        10                  15                  20 gcg tgc atg gcc ccc agg ggc acg cag gct gaa gaa agt ccc ttc gtg    572
Ala Cys Met Ala Pro Arg Gly Thr Gln Ala Glu Glu Ser Pro Phe Val
    25                  30                  35 ggc aac cca ggg aat atc aca ggt gcc cgg gga ctc acg ggc acc ctt    620
Gly Asn Pro Gly Asn Ile Thr Gly Ala Arg Gly Leu Thr Gly Thr Leu
40                  45                  50 cgg tgt cag ctc cag gtt cag gga gag ccc ccc gag gta cat tgg ctt    668
Arg Cys Gln Leu Gln Val Gln Gly Glu Pro Pro Glu Val His Trp Leu
55                  60                  65                  70 cgg gat gga cag atc ctg gag ctc gcg gac agc acc cag acc cag gtg    716
Arg Asp Gly Gln Ile Leu Glu Leu Ala Asp Ser Thr Gln Thr Gln Val
            75                  80                  85 ccc ctg ggt gag gat gaa cag gat gac tgg ata gtg gtc agc cag ctc    764
Pro Leu Gly Glu Asp Glu Gln Asp Asp Trp Ile Val Val Ser Gln Leu
        90                  95                 100 aga atc acc tcc ctg cag ctt tcc gac acg gga cag tac cag tgt ttg    812
Arg Ile Thr Ser Leu Gln Leu Ser Asp Thr Gly Gln Tyr Gln Cys Leu
    105                 110                 115 gtg ttt ctg gga cat cag acc ttc gtg tcc cag cct ggc tat gtt ggg    860
Val Phe Leu Gly His Gln Thr Phe Val Ser Gln Pro Gly Tyr Val Gly
120                 125                 130 ctg gag ggc ttg cct tac ttc ctg gag gag ccc gaa gac agg act gtg    908
Leu Glu Gly Leu Pro Tyr Phe Leu Glu Glu Pro Glu Asp Arg Thr Val
135                 140                 145                 150
```

```
gcc gcc aac acc ccc ttc aac ctg agc tgc caa gct cag gga ccc cca    956
Ala Ala Asn Thr Pro Phe Asn Leu Ser Cys Gln Ala Gln Gly Pro Pro
            155                 160                 165 gag ccc gtg gac cta ctc tgg ctc cag gat gct gtc ccc ctg gcc acg    1004
Glu Pro Val Asp Leu Leu Trp Leu Gln Asp Ala Val Pro Leu Ala Thr
            170                 175                 180 gct cca ggt cac ggc ccc cag cgc agc ctg cat gtt cca ggg ctg aac    1052
Ala Pro Gly His Gly Pro Gln Arg Ser Leu His Val Pro Gly Leu Asn
            185                 190                 195 aag aca tcc tct ttc tcc tgc gaa gcc cat aac gcc aag ggg gtc acc    1100
Lys Thr Ser Ser Phe Ser Cys Glu Ala His Asn Ala Lys Gly Val Thr
            200                 205                 210 aca tcc cgc aca gcc acc atc aca gtg ctc ccc cag cag ccc cgt aac    1148
Thr Ser Arg Thr Ala Thr Ile Thr Val Leu Pro Gln Gln Pro Arg Asn
215             220                 225                 230 ctc cac ctg gtc tcc cgc caa ccc acg gag ctg gag gtg gct tgg act    1196
Leu His Leu Val Ser Arg Gln Pro Thr Glu Leu Glu Val Ala Trp Thr
                235                 240                 245 cca ggc ctg agc ggc atc tac ccc ctg acc cac tgc acc ctg cag gct    1244
Pro Gly Leu Ser Gly Ile Tyr Pro Leu Thr His Cys Thr Leu Gln Ala
            250                 255                 260 gtg ctg tca gac gat ggg atg ggc atc cag gcg gga gaa cca gac ccc    1292
Val Leu Ser Asp Asp Gly Met Gly Ile Gln Ala Gly Glu Pro Asp Pro
            265                 270                 275 cca gag gag ccc ctc acc tcg caa gca tcc gtg ccc ccc cat cag ctt    1340
Pro Glu Glu Pro Leu Thr Ser Gln Ala Ser Val Pro Pro His Gln Leu
            280                 285                 290 cgg cta ggc agc ctc cat cct cac acc cct tat cac atc cgc gtg gca    1388
Arg Leu Gly Ser Leu His Pro His Thr Pro Tyr His Ile Arg Val Ala
295             300                 305                 310 tgc acc agc agc cag ggc ccc tca tcc tgg acc cac tgg ctt cct gtg    1436
Cys Thr Ser Ser Gln Gly Pro Ser Ser Trp Thr His Trp Leu Pro Val
                315                 320                 325 gag acg ccg gag gga gtg ccc ctg ggc ccc cct gag aac att agt gct    1484
Glu Thr Pro Glu Gly Val Pro Leu Gly Pro Pro Glu Asn Ile Ser Ala
            330                 335                 340 acg cgg aat ggg agc cag gcc ttc gtg cat tgg caa gag ccc cgg gcg    1532
Thr Arg Asn Gly Ser Gln Ala Phe Val His Trp Gln Glu Pro Arg Ala
            345                 350                 355 ccc ctg cag ggt acc ctg tta ggg tac cgg ctg gcg tat caa ggc cag    1580
Pro Leu Gln Gly Thr Leu Leu Gly Tyr Arg Leu Ala Tyr Gln Gly Gln
            360                 365                 370 gac acc cca gag gtg cta atg gac ata ggg cta agg caa gag gtg acc    1628
Asp Thr Pro Glu Val Leu Met Asp Ile Gly Leu Arg Gln Glu Val Thr
375             380                 385                 390 ctg gag ctg cag ggg gac ggg tct gtg tcc aat ctg aca gtg tgt gtg    1676
Leu Glu Leu Gln Gly Asp Gly Ser Val Ser Asn Leu Thr Val Cys Val
                395                 400                 405 gca gcc tac act gct gct ggg gat gga ccc tgg agc ctc cca gta ccc    1724
Ala Ala Tyr Thr Ala Ala Gly Asp Gly Pro Trp Ser Leu Pro Val Pro
            410                 415                 420 ctg gag gcc tgg cgc cca gtg aag gaa cct tca act cct gcc ttc tcg    1772
Leu Glu Ala Trp Arg Pro Val Lys Glu Pro Ser Thr Pro Ala Phe Ser
            425                 430                 435 tgg ccc tgg tgg tat gta ctg cta gga gca gtc gtg gcc gct gcc tgt    1820
Trp Pro Trp Trp Tyr Val Leu Leu Gly Ala Val Val Ala Ala Ala Cys
            440                 445                 450 gtc ctc atc ttg gct ctc ttc ctt gtc cac cgg cga aag aag gag acc    1868
Val Leu Ile Leu Ala Leu Phe Leu Val His Arg Arg Lys Lys Glu Thr
455             460                 465                 470
```

```
cgt tat gga gaa gtg ttt gaa cca aca gtg gaa aga ggt gaa ctg gta    1916
Arg Tyr Gly Glu Val Phe Glu Pro Thr Val Glu Arg Gly Glu Leu Val
                475                 480                 485 gtc agg tac cgc gtg cgc aag tcc tac agt cgt cgg acc act gaa gct    1964
Val Arg Tyr Arg Val Arg Lys Ser Tyr Ser Arg Arg Thr Thr Glu Ala
            490                 495                 500 acc ttg aac agc ctg ggc atc agt gaa gag ctg aag gag aag ctg cgg    2012
Thr Leu Asn Ser Leu Gly Ile Ser Glu Glu Leu Lys Glu Lys Leu Arg
        505                 510                 515 gat gtg atg gtg gac cgg cac aag gtg gcc ctg ggg aag act ctg gga    2060
Asp Val Met Val Asp Arg His Lys Val Ala Leu Gly Lys Thr Leu Gly
    520                 525                 530 gag gga gag ttt gga gct gtg atg gaa ggc cag ctc aac cag gac gac    2108
Glu Gly Glu Phe Gly Ala Val Met Glu Gly Gln Leu Asn Gln Asp Asp
535                 540                 545                 550 tcc atc ctc aag gtg gct gtg aag acg atg aag att gcc atc tgc acg    2156
Ser Ile Leu Lys Val Ala Val Lys Thr Met Lys Ile Ala Ile Cys Thr
                555                 560                 565 agg tca gag ctg gag gat ttc ctg agt gaa gcg gtc tgc atg aag gaa    2204
Arg Ser Glu Leu Glu Asp Phe Leu Ser Glu Ala Val Cys Met Lys Glu
            570                 575                 580 ttt gac cat ccc aac gtc atg agg ctc atc ggt gtc tgt ttc cag ggt    2252
Phe Asp His Pro Asn Val Met Arg Leu Ile Gly Val Cys Phe Gln Gly
        585                 590                 595 tct gaa cga gag agc ttc cca gca cct gtg gtc atc tta cct ttc atg    2300
Ser Glu Arg Glu Ser Phe Pro Ala Pro Val Val Ile Leu Pro Phe Met
    600                 605                 610 aaa cat gga gac cta cac agc ttc ctc ctc tat tcc cgg ctc ggg gac    2348
Lys His Gly Asp Leu His Ser Phe Leu Leu Tyr Ser Arg Leu Gly Asp
615                 620                 625                 630 cag cca gtg tac ctg ccc act cag atg cta gtg aag ttc atg gca gac    2396
Gln Pro Val Tyr Leu Pro Thr Gln Met Leu Val Lys Phe Met Ala Asp
                635                 640                 645 atc gcc agt ggc atg gag tat ctg agt acc aag aga ttc ata cac cgg    2444
Ile Ala Ser Gly Met Glu Tyr Leu Ser Thr Lys Arg Phe Ile His Arg
            650                 655                 660 gac ctg gcg gcc agg aac tgc atg ctg aat gag aac atg tcc gtg tgt    2492
Asp Leu Ala Ala Arg Asn Cys Met Leu Asn Glu Asn Met Ser Val Cys
        665                 670                 675 gtg gcg gac ttc ggg ctc tcc aag aag atc tac aat ggg gac tac tac    2540
Val Ala Asp Phe Gly Leu Ser Lys Lys Ile Tyr Asn Gly Asp Tyr Tyr
    680                 685                 690 cgc cag gga cgt atc gcc aag atg cca gtc aag tgg att gcc att gag    2588
Arg Gln Gly Arg Ile Ala Lys Met Pro Val Lys Trp Ile Ala Ile Glu
695                 700                 705                 710 agt cta gct gac cgt gtc tac acc agc aag agc gat gtg tgg tcc ttc    2636
Ser Leu Ala Asp Arg Val Tyr Thr Ser Lys Ser Asp Val Trp Ser Phe
                715                 720                 725 ggg gtg aca atg tgg gag att gcc aca aga ggc caa acc cca tat ccg    2684
Gly Val Thr Met Trp Glu Ile Ala Thr Arg Gly Gln Thr Pro Tyr Pro
            730                 735                 740 ggc gtg gag aac agc gag att tat gac tat ctc gca cag gga aat cgc    2732
Gly Val Glu Asn Ser Glu Ile Tyr Asp Tyr Leu Arg Gln Gly Asn Arg
        745                 750                 755 ctg aag cag cct gcg gac tgt ctg gat gga ctg tat gcc ttg atg tcg    2780
Leu Lys Gln Pro Ala Asp Cys Leu Asp Gly Leu Tyr Ala Leu Met Ser
    760                 765                 770 cgg tgc tgg gag cta aat ccc cag gac cgg cca agt ttt aca gag ctg    2828
Arg Cys Trp Glu Leu Asn Pro Gln Asp Arg Pro Ser Phe Thr Glu Leu
775                 780                 785                 790
```

| | | |
|---|---|---|
| cgg gaa gat ttg gag aac aca ctg aag gcc ttg cct cct gcc cag gag<br>Arg Glu Asp Leu Glu Asn Thr Leu Lys Ala Leu Pro Pro Ala Gln Glu<br>795 800 805 | | 2876 |
| cct gac gaa atc ctc tat gtc aac atg gat gag ggt gga ggt tat cct<br>Pro Asp Glu Ile Leu Tyr Val Asn Met Asp Glu Gly Gly Gly Tyr Pro<br>810 815 820 | | 2924 |
| gaa ccc cct gga gct gca gga gga gct gac ccc cca acc cag cca gac<br>Glu Pro Pro Gly Ala Ala Gly Gly Ala Asp Pro Pro Thr Gln Pro Asp<br>825 830 835 | | 2972 |
| cct aag gat tcc tgt agc tgc ctc act gcg gct gag gtc cat cct gct<br>Pro Lys Asp Ser Cys Ser Cys Leu Thr Ala Ala Glu Val His Pro Ala<br>840 845 850 | | 3020 |
| gga cgc tat gtc ctc tgc cct tcc aca acc cct agc ccc gct cag cct<br>Gly Arg Tyr Val Leu Cys Pro Ser Thr Thr Pro Ser Pro Ala Gln Pro<br>855 860 865 870 | | 3068 |
| gct gat agg ggc tcc cca gca gcc cca ggg cag gag gat ggt gcc tga<br>Ala Asp Arg Gly Ser Pro Ala Ala Pro Gly Gln Glu Asp Gly Ala<br>875 880 885 | | 3116 |
| gacaaccctc cacctggtac tccctctcag gatccaagct aagcactgcc actggggaaa | | 3176 |
| actccacctt cccactttcc caccccacgc cttatcccca cttgcagccc tgtcttccta | | 3236 |
| cctatcccac ctccatccca gacaggtccc tcccttctc tgtgcagtag catcaccttg | | 3296 |
| aaagcagtag catcaccatc tgtaaaagga aggggttgga ttgcaatatc tgaagccctc | | 3356 |
| ccaggtgtta acattccaag actctagagt ccaaggttta aagagtctag attcaaaggt | | 3416 |
| tctaggtttc aaagatgctg tgagtctttg gttctaagga cctgaaattc caaagtctct | | 3476 |
| aattctatta aagtgctaag gttctaaggc ctactttttt tttttttttt tttttttttt | | 3536 |
| ttttttttgc gatagagtct cactgtgtca cccaggctgg agtgcagtgg tgcaatctcg | | 3596 |
| cctcactgca accttcacct accgagttca agtgattttc ctgccttggc ctcccaagta | | 3656 |
| gctgggatta caggtgtgtg ccaccacacc cggctaattt ttatattttt agtagagaca | | 3716 |
| gggtttcacc atgttggcca ggctggtcta aaactcctga cctcaagtga tctgcccacc | | 3776 |
| tcagcctccc aaagtgctga gattacaggc atgagccact gcactcaacc ttaagaccta | | 3836 |
| ctgttctaaa gctctgacat tatgtggttt tagattttct ggttctaaca tttttgataa | | 3896 |
| agcctcaagg ttttaggttc taaagttcta agattctgat tttaggagct aaggctctat | | 3956 |
| gagtctagat gtttattctt ctagagttca gagtccttaa aatgtaagat tatagattct | | 4016 |
| aaagattcta tagttctaga catggaggtt ctaaggccta ggattctaaa atgtgatgtt | | 4076 |
| ctaaggctct gagagtctag attctctggc tgtaaggctc tagatcataa ggcttcaaaa | | 4136 |
| tgttatcttc tcaagttcta agattctaat gatgatcaat tatagtttct gaggctttat | | 4196 |
| gataatagat tctcttgtat aagatcctag atcctaaggg tcgaaagctc tagaatctgc | | 4256 |
| aattcaaaag ttccaagagt ctaaagatgg agtttctaag gtccggtgtt ctaagatgtg | | 4316 |
| atattctaag acttactcta agatcttaga ttctctgtgt ctaagattct agatcagatg | | 4376 |
| ctccaagatt ctagatgatt aaataagatt ctaacggtct gttctgtttc aaggcactct | | 4436 |
| agattccatt ggtccaagat tccggatcct aagcatctaa gttataagac tctcacactc | | 4496 |
| agttgtgact aactagacac caaagttcta ataatttcta atgttggaca cctttaggtt | | 4556 |
| ctttgctgca ttctgcctct ctaggaccat ggttaagagt ccaagaatcc acatttctaa | | 4616 |
| aatcttatag ttctaggcac tgtagttcta agactcaaat gttctaagtt tctaagattc | | 4676 |
| taaaggtcca caggtctaga ctattaggtg caatttcaag gttctaaccc tatactgtag | | 4736 |
| tattctttgg ggtgcccctc tccttcttag ctatcattgc ttcctcctcc caactgtgg | | 4796 |

-continued

```
gggtgtgccc ccttcaagcc tgtgcaatgc attagggatg cctcctttcc cgcaggggat      4856
ggacgatctc ccacctttcg ggccatgttg cccccgtgag ccaatccctc accttctgag      4916
tacagagtgt ggactctggt gcctccagag gggctcaggt cacataaaac tttgtatatc      4976
aacgaaaaaa a                                                            4987
```

<210> SEQ ID NO 4
<211> LENGTH: 885
<212> TYPE: PRT
<213> ORGANISM: Homo sapiens

<400> SEQUENCE: 4

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
```

```
                    340                 345                 350
Trp Gln Glu Pro Arg Ala Pro Leu Gln Gly Thr Leu Leu Gly Tyr Arg
                355                 360                 365
Leu Ala Tyr Gln Gly Gln Asp Thr Pro Glu Val Leu Met Asp Ile Gly
            370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Gly Asp Gly Pro
                405                 410                 415
Trp Ser Leu Pro Val Pro Leu Glu Ala Trp Arg Pro Val Lys Glu Pro
                420                 425                 430
Ser Thr Pro Ala Phe Ser Trp Pro Trp Trp Tyr Val Leu Leu Gly Ala
                435                 440                 445
Val Val Ala Ala Ala Cys Val Leu Ile Leu Ala Leu Phe Leu Val His
            450                 455                 460
Arg Arg Lys Lys Glu Thr Arg Tyr Gly Glu Val Phe Glu Pro Thr Val
465                 470                 475                 480
Glu Arg Gly Glu Leu Val Val Arg Tyr Arg Val Arg Lys Ser Tyr Ser
                485                 490                 495
Arg Arg Thr Thr Glu Ala Thr Leu Asn Ser Leu Gly Ile Ser Glu Glu
                500                 505                 510
Leu Lys Glu Lys Leu Arg Asp Val Met Val Asp Arg His Lys Val Ala
            515                 520                 525
Leu Gly Lys Thr Leu Gly Glu Gly Glu Phe Gly Ala Val Met Glu Gly
            530                 535                 540
Gln Leu Asn Gln Asp Asp Ser Ile Leu Lys Val Ala Lys Thr Met
545                 550                 555                 560
Lys Ile Ala Ile Cys Thr Arg Ser Glu Leu Glu Asp Phe Leu Ser Glu
                565                 570                 575
Ala Val Cys Met Lys Glu Phe Asp His Pro Asn Val Met Arg Leu Ile
                580                 585                 590
Gly Val Cys Phe Gln Gly Ser Glu Arg Glu Ser Phe Pro Ala Pro Val
            595                 600                 605
Val Ile Leu Pro Phe Met Lys His Gly Asp Leu His Ser Phe Leu Leu
            610                 615                 620
Tyr Ser Arg Leu Gly Asp Gln Pro Val Tyr Leu Pro Thr Gln Met Leu
625                 630                 635                 640
Val Lys Phe Met Ala Asp Ile Ala Ser Gly Met Glu Tyr Leu Ser Thr
                645                 650                 655
Lys Arg Phe Ile His Arg Asp Leu Ala Ala Arg Asn Cys Met Leu Asn
                660                 665                 670
Glu Asn Met Ser Val Cys Val Ala Asp Phe Gly Leu Ser Lys Lys Ile
            675                 680                 685
Tyr Asn Gly Asp Tyr Tyr Arg Gln Gly Arg Ile Ala Lys Met Pro Val
            690                 695                 700
Lys Trp Ile Ala Ile Glu Ser Leu Ala Asp Arg Val Tyr Thr Ser Lys
705                 710                 715                 720
Ser Asp Val Trp Ser Phe Gly Val Thr Met Trp Glu Ile Ala Thr Arg
                725                 730                 735
Gly Gln Thr Pro Tyr Pro Gly Val Glu Asn Ser Glu Ile Tyr Asp Tyr
            740                 745                 750
Leu Arg Gln Gly Asn Arg Leu Lys Gln Pro Ala Asp Cys Leu Asp Gly
            755                 760                 765
```

```
Leu Tyr Ala Leu Met Ser Arg Cys Trp Glu Leu Asn Pro Gln Asp Arg
        770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Tyr Pro Glu Pro Gly Ala Ala Gly Ala Asp
                820                 825                 830

Pro Pro Thr Gln Pro Asp Pro Lys Asp Ser Cys Ser Cys Leu Thr Ala
            835                 840                 845

Ala Glu Val His Pro Ala Gly Arg Tyr Val Leu Cys Pro Ser Thr Thr
        850                 855                 860

Pro Ser Pro Ala Gln Pro Ala Asp Arg Gly Ser Pro Ala Ala Pro Gly
865                 870                 875                 880

Gln Glu Asp Gly Ala
                885

<210> SEQ ID NO 5
<211> LENGTH: 4200
<212> TYPE: DNA
<213> ORGANISM: Mus musculus
<220> FEATURE:
<221> NAME/KEY: CDS
<222> LOCATION: (144)..(2783)

<400> SEQUENCE: 5
ggaggagttg agccagccga ggggctcccg ctgtgccagg cgggcagtgc caaatcccag       60
gagccctgcc cccttttccta gcgaggtgcc catcaacttc ggaagaaagt ttggcatcaa     120
tctgagctgt ggtgtctgg agg atg ggc agg gtc ccg ctg gcc tgg tgg ttg      173
                         Met Gly Arg Val Pro Leu Ala Trp Trp Leu
                          1               5                  10 gcg ctg tgc tgc tgg ggg tgt gca gcc cat aag gac aca cag acc gag      221
Ala Leu Cys Cys Trp Gly Cys Ala Ala His Lys Asp Thr Gln Thr Glu
             15                  20                  25 gct ggc agc ccg ttt gtg ggg aac cca ggg aat atc aca ggt gcc aga      269
Ala Gly Ser Pro Phe Val Gly Asn Pro Gly Asn Ile Thr Gly Ala Arg
         30                  35                  40 gga ctc acg ggg aca ctt cgg tgt gag ctc cag gtt cag ggg gaa ccc      317
Gly Leu Thr Gly Thr Leu Arg Cys Glu Leu Gln Val Gln Gly Glu Pro
     45                  50                  55 cct gag gtg gtg tgg ctt cga gat gga cag atc cta gaa ctg gct gat      365
Pro Glu Val Val Trp Leu Arg Asp Gly Gln Ile Leu Glu Leu Ala Asp
 60                  65                  70 aac acc cag acc cag gtg cct ctg ggc gaa gac tgg caa gat gaa tgg      413
Asn Thr Gln Thr Gln Val Pro Leu Gly Glu Asp Trp Gln Asp Glu Trp
 75                  80                  85                  90 aaa gtt gtc agt cag ctc aga atc tca gcc ctg caa ctt tca gat gca      461
Lys Val Val Ser Gln Leu Arg Ile Ser Ala Leu Gln Leu Ser Asp Ala
                 95                 100                 105 ggg gag tac cag tgt atg gtg cat cta gaa gga cgg acc ttt gtg tct      509
Gly Glu Tyr Gln Cys Met Val His Leu Glu Gly Arg Thr Phe Val Ser
             110                 115                 120 cag ccg ggc ttt gta ggg ctg gaa ggt ctc ccg tac ttc ctg gag gag      557
Gln Pro Gly Phe Val Gly Leu Glu Gly Leu Pro Tyr Phe Leu Glu Glu
         125                 130                 135 cct gag gac aaa gct gtg cct gcc aac acc cct ttc aac cta agc tgc      605
Pro Glu Asp Lys Ala Val Pro Ala Asn Thr Pro Phe Asn Leu Ser Cys
     140                 145                 150 cag gcc cag gga ccc ccg gaa ccc gtg acc cta ctc tgg ctt caa gat      653
```

```
Gln Ala Gln Gly Pro Pro Glu Pro Val Thr Leu Leu Trp Leu Gln Asp
155                 160                 165                 170 gct gtc ccc ctg gcc cca gtc aca gga cac agc tcc cag cac agt ctg      701
Ala Val Pro Leu Ala Pro Val Thr Gly His Ser Ser Gln His Ser Leu
                175                 180                 185 caa act cca ggc ctg aac aag aca tct tct ttc tca tgt gaa gcc cac      749
Gln Thr Pro Gly Leu Asn Lys Thr Ser Ser Phe Ser Cys Glu Ala His
                    190                 195                 200 aat gcc aag gga gtc acc acc tcc cgc aca gcc acc atc aca gtg ctc      797
Asn Ala Lys Gly Val Thr Thr Ser Arg Thr Ala Thr Ile Thr Val Leu
            205                 210                 215 ccc cag agg cct cac cat ctc cac gtg gtt tcc aga caa cct acg gag      845
Pro Gln Arg Pro His His Leu His Val Val Ser Arg Gln Pro Thr Glu
220                 225                 230 cta gag gta gct tgg acc cct ggc ctg agt ggc atc tac ccg ctc acc      893
Leu Glu Val Ala Trp Thr Pro Gly Leu Ser Gly Ile Tyr Pro Leu Thr
235                 240                 245                 250 cac tgc aac ctg cag gcc gtg ctg tca gac gat ggg gtg ggt atc tgg      941
His Cys Asn Leu Gln Ala Val Leu Ser Asp Asp Gly Val Gly Ile Trp
                    255                 260                 265 ctg gga aag tca gat cct cct gaa gac ccc ctc acc ttg caa gta tca      989
Leu Gly Lys Ser Asp Pro Pro Glu Asp Pro Leu Thr Leu Gln Val Ser
                270                 275                 280 gtg ccc ccc cac cag ctt cgg ctg gaa aag ctc ctt cct cac acc ccg     1037
Val Pro Pro His Gln Leu Arg Leu Glu Lys Leu Leu Pro His Thr Pro
            285                 290                 295 tat cac atc cgg ata tcc tgc agc agc agc cag ggc ccc tca cct tgg     1085
Tyr His Ile Arg Ile Ser Cys Ser Ser Ser Gln Gly Pro Ser Pro Trp
300                 305                 310 acc cac tgg ctt cct gtg gag acc aca gag gga gtg ccc ttg ggt ccc     1133
Thr His Trp Leu Pro Val Glu Thr Thr Glu Gly Val Pro Leu Gly Pro
315                 320                 325                 330 cct gag aac gtt agc gcc atg cgg aat ggg agc cag gtc ctc gtg cgt     1181
Pro Glu Asn Val Ser Ala Met Arg Asn Gly Ser Gln Val Leu Val Arg
                    335                 340                 345 tgg cag gag cca agg gtg ccc ctg caa ggc acc ctg tta ggg tac cgg     1229
Trp Gln Glu Pro Arg Val Pro Leu Gln Gly Thr Leu Leu Gly Tyr Arg
                350                 355                 360 ctg gca tat cga ggc cag gac acc ccc gag gta ctt atg gat ata ggg     1277
Leu Ala Tyr Arg Gly Gln Asp Thr Pro Glu Val Leu Met Asp Ile Gly
            365                 370                 375 cta act cga gag gtg acc ttg gaa ctg cgg ggg gac agg cct gtg gct     1325
Leu Thr Arg Glu Val Thr Leu Glu Leu Arg Gly Asp Arg Pro Val Ala
380                 385                 390 aac ctg act gtg tct gtg aca gcc tat acc tcg gct ggg gat ggg ccc     1373
Asn Leu Thr Val Ser Val Thr Ala Tyr Thr Ser Ala Gly Asp Gly Pro
395                 400                 405                 410 tgg agc ctt cct gtg ccc cta gag ccc tgg cgc cca gtg agt gaa ccc     1421
Trp Ser Leu Pro Val Pro Leu Glu Pro Trp Arg Pro Val Ser Glu Pro
                415                 420                 425 cca cct cgc gcc ttc tcg tgg cct tgg tgg tat gta ctg ctg gga gca     1469
Pro Pro Arg Ala Phe Ser Trp Pro Trp Trp Tyr Val Leu Leu Gly Ala
                430                 435                 440 ctt gtg gct gcc gcc tgc gtc ctc atc ttg gcc ctg ttc ctt gtc cat     1517
Leu Val Ala Ala Ala Cys Val Leu Ile Leu Ala Leu Phe Leu Val His
            445                 450                 455 cgg agg aag aag gag act cga tat ggg gag gtg ttt gag cca acc gtg     1565
Arg Arg Lys Lys Glu Thr Arg Tyr Gly Glu Val Phe Glu Pro Thr Val
460                 465                 470 gaa aga ggt gaa ctg gta gtc agg tac cgt gtc cga aag tcc tac agc     1613
```

```
Glu Arg Gly Glu Leu Val Val Arg Tyr Arg Val Arg Lys Ser Tyr Ser
475                 480                 485                 490 cgg cgg acc act gaa gcc acc ttg aac agt ctg ggc atc agt gaa gag   1661
Arg Arg Thr Thr Glu Ala Thr Leu Asn Ser Leu Gly Ile Ser Glu Glu
                495                 500                 505 ctg aag gag aaa cta cga gac gtc atg gta gat cgg cat aag gtg gcc   1709
Leu Lys Glu Lys Leu Arg Asp Val Met Val Asp Arg His Lys Val Ala
            510                 515                 520 ttg ggg aag acc ctg gga gaa gga gaa ttt ggc gct gtg atg gaa ggt   1757
Leu Gly Lys Thr Leu Gly Glu Gly Glu Phe Gly Ala Val Met Glu Gly
            525                 530                 535 cag ctc aat cag gat gac tcc atc ctc aag gtc gct gtg aag acc atg   1805
Gln Leu Asn Gln Asp Asp Ser Ile Leu Lys Val Ala Val Lys Thr Met
        540                 545                 550 aaa att gcc atc tgc aca aga tca gag ctg gag gat ttc ctg agt gaa   1853
Lys Ile Ala Ile Cys Thr Arg Ser Glu Leu Glu Asp Phe Leu Ser Glu
555                 560                 565                 570 gct gtc tgc atg aag gaa ttt gac cac ccc aac gtc atg agg ctc att   1901
Ala Val Cys Met Lys Glu Phe Asp His Pro Asn Val Met Arg Leu Ile
                575                 580                 585 ggc gtc tgt ttt cag ggc tct gac aga gag ggt ttc cca gaa cct gtg   1949
Gly Val Cys Phe Gln Gly Ser Asp Arg Glu Gly Phe Pro Glu Pro Val
            590                 595                 600 gtc atc ttg cct ttc atg aaa cac gga gac cta cac agt ttc ctc ctg   1997
Val Ile Leu Pro Phe Met Lys His Gly Asp Leu His Ser Phe Leu Leu
            605                 610                 615 tac tcc cgg ctc ggg gac cag cca gtg ttc ctg ccc act cag atg cta   2045
Tyr Ser Arg Leu Gly Asp Gln Pro Val Phe Leu Pro Thr Gln Met Leu
        620                 625                 630 gtg aag ttc atg gcc gac att gcc agt ggt atg gag tac ctg agt acc   2093
Val Lys Phe Met Ala Asp Ile Ala Ser Gly Met Glu Tyr Leu Ser Thr
635                 640                 645                 650 aag aga ttc ata cat cgg gac ctg gct gcc agg aac tgc atg ctg aat   2141
Lys Arg Phe Ile His Arg Asp Leu Ala Ala Arg Asn Cys Met Leu Asn
                655                 660                 665 gag aac atg tcc gtg tgt gtg gca gac ttc ggg ctc tcc aag aag atc   2189
Glu Asn Met Ser Val Cys Val Ala Asp Phe Gly Leu Ser Lys Lys Ile
            670                 675                 680 tac aac ggg gat tac tac cgc caa ggg cgc att gcc aag atg cca gtc   2237
Tyr Asn Gly Asp Tyr Tyr Arg Gln Gly Arg Ile Ala Lys Met Pro Val
            685                 690                 695 aag tgg att gct att gag agt ctg gca gat cgg gtc tac acc agc aag   2285
Lys Trp Ile Ala Ile Glu Ser Leu Ala Asp Arg Val Tyr Thr Ser Lys
700                 705                 710 agc gat gtg tgg tcc ttc ggt gtg aca atg tgg gag atc gcc acc cga   2333
Ser Asp Val Trp Ser Phe Gly Val Thr Met Trp Glu Ile Ala Thr Arg
715                 720                 725                 730 ggc caa act ccc tat cca ggg gtg gag aac agt gag att tac gac tac   2381
Gly Gln Thr Pro Tyr Pro Gly Val Glu Asn Ser Glu Ile Tyr Asp Tyr
                735                 740                 745 ctc cgt caa gga aat cgg ctg aaa cag cct gtg gac tgt ctg gac ggc   2429
Leu Arg Gln Gly Asn Arg Leu Lys Gln Pro Val Asp Cys Leu Asp Gly
            750                 755                 760 ctg tat gcc ctg atg tct cgg tgc tgg gaa ctg aac cct cga gac cgg   2477
Leu Tyr Ala Leu Met Ser Arg Cys Trp Glu Leu Asn Pro Arg Asp Arg
        765                 770                 775 cca agt ttt gcg gag ctc cgg gaa gac ttg gag aac aca ctg aag gct   2525
Pro Ser Phe Ala Glu Leu Arg Glu Asp Leu Glu Asn Thr Leu Lys Ala
        780                 785                 790 ctg ccc cct gct cag gag cca gat gaa atc ctc tat gtc aac atg gat   2573
```

| | | | | | | | | | | | | | | |
|---|---|---|---|---|---|---|---|---|---|---|---|---|---|---|
| Leu | Pro | Pro | Ala | Gln | Glu | Pro | Asp | Glu | Ile | Leu | Tyr | Val | Asn | Met | Asp |
| 795 | | | | | 800 | | | | | 805 | | | | | 810 |

```
gag ggc gga agc cac ctt gaa ccc cgt ggg gct gct gga gga gct gac    2621
Glu Gly Gly Ser His Leu Glu Pro Arg Gly Ala Ala Gly Gly Ala Asp
            815                 820                 825 ccc cca acc caa cct gat cct aag gat tcc tgt agc tgt ctc act gca    2669
Pro Pro Thr Gln Pro Asp Pro Lys Asp Ser Cys Ser Cys Leu Thr Ala
            830                 835                 840 gct gac gtc cac tca gct gga cgc tat gtc ctt tgt cct tct aca gcc    2717
Ala Asp Val His Ser Ala Gly Arg Tyr Val Leu Cys Pro Ser Thr Ala
            845                 850                 855 cca gga ccc act ctg tct gct gac aga ggc tgc cca gca cct cca ggg    2765
Pro Gly Pro Thr Leu Ser Ala Asp Arg Gly Cys Pro Ala Pro Pro Gly
            860                 865                 870 cag gag gac gga gcc tga gacaatcttc cacctgggac atcctctcag           2813
Gln Glu Asp Gly Ala
875 gacccaagct aggcactgcc actggggaa agctcacccc cccactccgt cactccaggc    2873 cttctcccca gatgcagaat ggccttccct cccttctcag atgcagtcca tgccttatgc    2933 accctatcca taacagtttc aagggatcgt ctcacatctt ccatcccagc gttctagatt    2993 ttaaggtttg agtttagagt tcaaagttct caaagatgat gagtctttgg accgagatgc    3053 ttgtttctag gtctgcagcg ctgttgctat agacaggccc actgctcgaa ggctctgaga    3113 ttctatggct ctagattttt ctggctctat aattcgtggc aatgctccca tggttttagg    3173 ttgcacgact ctgagattcc aggacctaag gcttctagac tttatttttc tggagccagg    3233 ggtcctgtca gtggaagatt gtagattttt aaattctaaa gattctaggc atgaaggttc    3293 taaggcatac tgcttctcca gtttaacagt ttagggctca tgttggaata ctccagatca    3353 taatgtttca aacttttatt ttttttaatt tctaagaccc cagtgatggt caactacaga    3413 ttctgaagcc ttatgaccat agattctttt atataaaaat cctgtatctc aaggaaatat    3473 gattctagac tctgaaattc caaagcttta agagtctcca gatggagttt ctaagctatg    3533 atgtggtgat aatctaaagt ttagtccaag gttctagatt cctaagcttc cacgtcatct    3593 gctcccagga ttccagatta ttaaaactcta aaactctaat gttggcctga tcttcgtctc    3653 aggccctgta ggatgctgtg ggtcctcagc atctaagtca caagaggctc cagttaacga    3713 ggactaatga gacaccaaag ttctaaccac ttctaatgct ggacacctct aggttctatg    3773 ctgcttttg cctttctagc acataattaa atgcccaaga atacatatgt ctaaagatct    3833 taaatctcta agcactatgg agccaatgtt ttgagtgtct gagattctaa aggtccacag    3893 tctagagtat taggtacgac tccaagggtg ggcgcttgta gccatcctaa gtcctttccc    3953 tccttaagca cctatgctcc tcctctcctt gtgtgggta caccccacct taagcctgtg    4013 cgatgcactg ggaatgcctg ctttcctcca agggatgggt catctcccct catttggggc    4073 catgttgccc cttgagccag tccctatgc ctgttctgaa gtgtggactc tggtgcctcc    4133 agagaggctc agatcacata aaactttgt cagtcactaa aaaaaaaaa aaaaaaaaa    4193 aaaaaaa                                                             4200
```

<210> SEQ ID NO 6
<211> LENGTH: 879
<212> TYPE: PRT
<213> ORGANISM: Mus musculus

<400> SEQUENCE: 6

Met Gly Arg Val Pro Leu Ala Trp Trp Leu Ala Leu Cys Cys Trp Gly

-continued

```
1               5                   10                  15
Cys Ala Ala His Lys Asp Thr Gln Thr Glu Ala Gly Ser Pro Phe Val
                20                  25                  30
Gly Asn Pro Gly Asn Ile Thr Gly Ala Arg Gly Leu Thr Gly Thr Leu
            35                  40                  45
Arg Cys Glu Leu Gln Val Gln Gly Glu Pro Pro Glu Val Val Trp Leu
        50                  55                  60
Arg Asp Gly Gln Ile Leu Glu Leu Ala Asp Asn Thr Gln Thr Gln Val
65                  70                  75                  80
Pro Leu Gly Glu Asp Trp Gln Asp Glu Trp Lys Val Val Ser Gln Leu
                85                  90                  95
Arg Ile Ser Ala Leu Gln Leu Ser Asp Ala Gly Glu Tyr Gln Cys Met
            100                 105                 110
Val His Leu Glu Gly Arg Thr Phe Val Ser Gln Pro Gly Phe Val Gly
        115                 120                 125
Leu Glu Gly Leu Pro Tyr Phe Leu Glu Glu Pro Glu Asp Lys Ala Val
        130                 135                 140
Pro Ala Asn Thr Pro Phe Asn Leu Ser Cys Gln Ala Gln Gly Pro Pro
145                 150                 155                 160
Glu Pro Val Thr Leu Leu Trp Leu Gln Asp Ala Val Pro Leu Ala Pro
                165                 170                 175
Val Thr Gly His Ser Ser Gln His Ser Leu Gln Thr Pro Gly Leu Asn
            180                 185                 190
Lys Thr Ser Ser Phe Ser Cys Glu Ala His Asn Ala Lys Gly Val Thr
        195                 200                 205
Thr Ser Arg Thr Ala Thr Ile Thr Val Leu Pro Gln Arg Pro His His
210                 215                 220
Leu His Val Val Ser Arg Gln Pro Thr Glu Leu Glu Val Ala Trp Thr
225                 230                 235                 240
Pro Gly Leu Ser Gly Ile Tyr Pro Leu Thr His Cys Asn Leu Gln Ala
            245                 250                 255
Val Leu Ser Asp Asp Gly Val Gly Ile Trp Leu Gly Lys Ser Asp Pro
        260                 265                 270
Pro Glu Asp Pro Leu Thr Leu Gln Val Ser Val Pro Pro His Gln Leu
    275                 280                 285
Arg Leu Glu Lys Leu Leu Pro His Thr Pro Tyr His Ile Arg Ile Ser
    290                 295                 300
Cys Ser Ser Ser Gln Gly Pro Ser Pro Trp Thr His Trp Leu Pro Val
305                 310                 315                 320
Glu Thr Thr Glu Gly Val Pro Leu Gly Pro Pro Glu Asn Val Ser Ala
                325                 330                 335
Met Arg Asn Gly Ser Gln Val Leu Val Arg Trp Gln Glu Pro Arg Val
            340                 345                 350
Pro Leu Gln Gly Thr Leu Leu Gly Tyr Arg Leu Ala Tyr Arg Gly Gln
        355                 360                 365
Asp Thr Pro Glu Val Leu Met Asp Ile Gly Leu Thr Arg Glu Val Thr
        370                 375                 380
Leu Glu Leu Arg Gly Asp Arg Pro Val Ala Asn Leu Thr Val Ser Val
385                 390                 395                 400
Thr Ala Tyr Thr Ser Ala Gly Asp Gly Pro Trp Ser Leu Pro Val Pro
                405                 410                 415
Leu Glu Pro Trp Arg Pro Val Ser Glu Pro Pro Arg Ala Phe Ser
            420                 425                 430
```

-continued

```
Trp Pro Trp Trp Tyr Val Leu Leu Gly Ala Leu Val Ala Ala Cys
        435                 440                 445

Val Leu Ile Leu Ala Leu Phe Leu Val His Arg Arg Lys Lys Glu Thr
450                 455                 460

Arg Tyr Gly Glu Val Phe Glu Pro Thr Val Glu Arg Gly Glu Leu Val
465                 470                 475                 480

Val Arg Tyr Arg Val Arg Lys Ser Tyr Ser Arg Arg Thr Thr Glu Ala
                485                 490                 495

Thr Leu Asn Ser Leu Gly Ile Ser Glu Glu Leu Lys Glu Lys Leu Arg
                500                 505                 510

Asp Val Met Val Asp Arg His Lys Val Ala Leu Gly Lys Thr Leu Gly
                515                 520                 525

Glu Gly Glu Phe Gly Ala Val Met Glu Gly Gln Leu Asn Gln Asp Asp
530                 535                 540

Ser Ile Leu Lys Val Ala Val Lys Thr Met Lys Ile Ala Ile Cys Thr
545                 550                 555                 560

Arg Ser Glu Leu Glu Asp Phe Leu Ser Glu Ala Val Cys Met Lys Glu
                565                 570                 575

Phe Asp His Pro Asn Val Met Arg Leu Ile Gly Val Cys Phe Gln Gly
                580                 585                 590

Ser Asp Arg Glu Gly Phe Pro Glu Pro Val Val Ile Leu Pro Phe Met
595                 600                 605

Lys His Gly Asp Leu His Ser Phe Leu Leu Tyr Ser Arg Leu Gly Asp
610                 615                 620

Gln Pro Val Phe Leu Pro Thr Gln Met Leu Val Lys Phe Met Ala Asp
625                 630                 635                 640

Ile Ala Ser Gly Met Glu Tyr Leu Ser Thr Lys Arg Phe Ile His Arg
                645                 650                 655

Asp Leu Ala Ala Arg Asn Cys Met Leu Asn Glu Asn Met Ser Val Cys
                660                 665                 670

Val Ala Asp Phe Gly Leu Ser Lys Lys Ile Tyr Asn Gly Asp Tyr Tyr
                675                 680                 685

Arg Gln Gly Arg Ile Ala Lys Met Pro Val Lys Trp Ile Ala Ile Glu
                690                 695                 700

Ser Leu Ala Asp Arg Val Tyr Thr Ser Lys Ser Asp Val Trp Ser Phe
705                 710                 715                 720

Gly Val Thr Met Trp Glu Ile Ala Thr Arg Gly Gln Thr Pro Tyr Pro
                725                 730                 735

Gly Val Glu Asn Ser Glu Ile Tyr Asp Tyr Leu Arg Gln Gly Asn Arg
                740                 745                 750

Leu Lys Gln Pro Val Asp Cys Leu Asp Gly Leu Tyr Ala Leu Met Ser
                755                 760                 765

Arg Cys Trp Glu Leu Asn Pro Arg Asp Arg Pro Ser Phe Ala Glu Leu
770                 775                 780

Arg Glu Asp Leu Glu Asn Thr Leu Lys Ala Leu Pro Pro Ala Gln Glu
785                 790                 795                 800

Pro Asp Glu Ile Leu Tyr Val Asn Met Asp Glu Gly Gly Ser His Leu
                805                 810                 815

Glu Pro Arg Gly Ala Ala Gly Gly Ala Asp Pro Pro Thr Gln Pro Asp
                820                 825                 830

Pro Lys Asp Ser Cys Ser Cys Leu Thr Ala Ala Asp Val His Ser Ala
                835                 840                 845

Gly Arg Tyr Val Leu Cys Pro Ser Thr Ala Pro Gly Pro Thr Leu Ser
850                 855                 860
```

```
Ala Asp Arg Gly Cys Pro Ala Pro Pro Gly Gln Glu Asp Gly Ala
865                 870                 875

<210> SEQ ID NO 7
<211> LENGTH: 2667
<212> TYPE: DNA
<213> ORGANISM: Rattus norvegicus
<220> FEATURE:
<221> NAME/KEY: CDS
<222> LOCATION: (1)..(2667)

<400> SEQUENCE: 7 atg ggc agg gtc ccg ctg gcc tgg tgc gtg gcg ctg tgc tgc tgg ggg      48
Met Gly Arg Val Pro Leu Ala Trp Cys Val Ala Leu Cys Cys Trp Gly
1               5                   10                  15 tgt gca gcc cct aag gac aca cag acc gag gct gac agc cca ttc gtg      96
Cys Ala Ala Pro Lys Asp Thr Gln Thr Glu Ala Asp Ser Pro Phe Val
                20                  25                  30 ggg aac cca ggg aat atc acg ggt gcc aga gga ctc acg ggg acc ctt     144
Gly Asn Pro Gly Asn Ile Thr Gly Ala Arg Gly Leu Thr Gly Thr Leu
            35                  40                  45 cgg tgt gag ctc cag gtt cag ggg gag ccc cct gag gtg atg tgg ctt     192
Arg Cys Glu Leu Gln Val Gln Gly Glu Pro Pro Glu Val Met Trp Leu
        50                  55                  60 cga gat gga cag atc cta gaa ctg gct gat aac acc cag acc cag gtg     240
Arg Asp Gly Gln Ile Leu Glu Leu Ala Asp Asn Thr Gln Thr Gln Val
65                  70                  75                  80 cct ctg ggc gaa gac tgg caa gat gaa tgg aaa gtc gtc agt cag ctc     288
Pro Leu Gly Glu Asp Trp Gln Asp Glu Trp Lys Val Val Ser Gln Leu
                85                  90                  95 aga atc tca gcc ctg caa ctt tca gat gca gga gag tac cag tgt atg     336
Arg Ile Ser Ala Leu Gln Leu Ser Asp Ala Gly Glu Tyr Gln Cys Met
                100                 105                 110 gtg cac ctg gaa gga cgg acc ttt gtg tct cag ccg ggc ttt gta gga     384
Val His Leu Glu Gly Arg Thr Phe Val Ser Gln Pro Gly Phe Val Gly
            115                 120                 125 ctg gaa ggt ctc ccg tac ttc ctg gag gaa cct gaa gac aaa gct gtg     432
Leu Glu Gly Leu Pro Tyr Phe Leu Glu Glu Pro Glu Asp Lys Ala Val
        130                 135                 140 cct gcc aac acc ccc ttc aac cta agc tgc cag gcc cag gga ccc ccg     480
Pro Ala Asn Thr Pro Phe Asn Leu Ser Cys Gln Ala Gln Gly Pro Pro
145                 150                 155                 160 gaa ccc gtg acc ctg ctc tgg ctt caa gat gct gtc cct ctg gcc cca     528
Glu Pro Val Thr Leu Leu Trp Leu Gln Asp Ala Val Pro Leu Ala Pro
                165                 170                 175 gtc gca gga tac agc ttt cag cac agt ttg caa gct cca ggc ctg aac     576
Val Ala Gly Tyr Ser Phe Gln His Ser Leu Gln Ala Pro Gly Leu Asn
            180                 185                 190 aag aca tct tct ttc tca tgt gaa gcc cac aat gcc aag gga gtc acc     624
Lys Thr Ser Ser Phe Ser Cys Glu Ala His Asn Ala Lys Gly Val Thr
        195                 200                 205 acc tcc cgc aca gct acc atc aca gtg ctc cca cag aga cct cac aat     672
Thr Ser Arg Thr Ala Thr Ile Thr Val Leu Pro Gln Arg Pro His Asn
    210                 215                 220 ctc cac gtg gtt tcc aga cat ccc acg gag cta gag gta gct tgg atc     720
Leu His Val Val Ser Arg His Pro Thr Glu Leu Glu Val Ala Trp Ile
225                 230                 235                 240 cct acc ctg agt ggc atc tac ccg ctc acc cac tgc acc ctg cag gct     768
Pro Thr Leu Ser Gly Ile Tyr Pro Leu Thr His Cys Thr Leu Gln Ala
                245                 250                 255 gtg ctg tca aac gat ggg gtg ggc gtc tgg ctg gga aag tca gat cct     816
```

-continued

```
Val Leu Ser Asn Asp Gly Val Gly Val Trp Leu Gly Lys Ser Asp Pro
            260                 265                 270 cct gaa gaa ccc ctc acc gtg caa gta tca gtg ccc ccc cac cag ctt      864
Pro Glu Glu Pro Leu Thr Val Gln Val Ser Val Pro Pro His Gln Leu
        275                 280                 285 cgg ctg gaa aag ctc ctt cct cac acc cca tat cac atc cgg gta tcc      912
Arg Leu Glu Lys Leu Leu Pro His Thr Pro Tyr His Ile Arg Val Ser
    290                 295                 300 tgc act agc agc cag ggc ccc tca cct tgg acc cac tgg ctt cct gtg      960
Cys Thr Ser Ser Gln Gly Pro Ser Pro Trp Thr His Trp Leu Pro Val
305                 310                 315                 320 gag acc acg gag gga gtg ccc ttg ggt ccc cct gag aac gtt agc gcc     1008
Glu Thr Thr Glu Gly Val Pro Leu Gly Pro Pro Glu Asn Val Ser Ala
                325                 330                 335 atg cgg aat ggg agc cag gcc ctc gtg cgt tgg cag gag cca agg gag     1056
Met Arg Asn Gly Ser Gln Ala Leu Val Arg Trp Gln Glu Pro Arg Glu
            340                 345                 350 ccc ttg cag ggc acc ctg tta ggg tac cgg ctg gca tat cga ggc cag     1104
Pro Leu Gln Gly Thr Leu Leu Gly Tyr Arg Leu Ala Tyr Arg Gly Gln
        355                 360                 365 gac acc ccc gag gta ctt atg gat ata ggg cta act cga gag gtg acc     1152
Asp Thr Pro Glu Val Leu Met Asp Ile Gly Leu Thr Arg Glu Val Thr
    370                 375                 380 ttg gaa ctt cgg ggg gac agg cct gtg gct aac ctg act gtg tct gtg     1200
Leu Glu Leu Arg Gly Asp Arg Pro Val Ala Asn Leu Thr Val Ser Val
385                 390                 395                 400 gca gcc tat acc tca gct ggg gat ggg ccc tgg agc ctt cct gtg ccc     1248
Ala Ala Tyr Thr Ser Ala Gly Asp Gly Pro Trp Ser Leu Pro Val Pro
                405                 410                 415 cta gag ccc tgg cgc cca ggg caa gga cag cca ctc cac cat ctg gtg     1296
Leu Glu Pro Trp Arg Pro Gly Gln Gly Gln Pro Leu His His Leu Val
            420                 425                 430 agt gaa ccc cca cct ccc gcc ttc tcg tgg cct tgg tgg tat gta ctg     1344
Ser Glu Pro Pro Pro Pro Ala Phe Ser Trp Pro Trp Trp Tyr Val Leu
        435                 440                 445 ctg gga gca ctt gtg gcc gcc gcc tgt gtc ctt atc ttg acc ctg ttc     1392
Leu Gly Ala Leu Val Ala Ala Ala Cys Val Leu Ile Leu Thr Leu Phe
    450                 455                 460 ctt gtc cat cgg agg aag aag gag acg aga tat ggg gag gtg ttc gag     1440
Leu Val His Arg Arg Lys Lys Glu Thr Arg Tyr Gly Glu Val Phe Glu
465                 470                 475                 480 cca act gtg gaa agg ggt gaa ctg gta gtc agg tac cgt gcc cga aag     1488
Pro Thr Val Glu Arg Gly Glu Leu Val Val Arg Tyr Arg Ala Arg Lys
                485                 490                 495 tcc tac agt cgc cgg acc acg gaa gcc acc ttg aac agt ctg ggc atc     1536
Ser Tyr Ser Arg Arg Thr Thr Glu Ala Thr Leu Asn Ser Leu Gly Ile
            500                 505                 510 agc gaa gag ctg aag gag aaa cta cga gac gtc atg gta gat cgg cat     1584
Ser Glu Glu Leu Lys Glu Lys Leu Arg Asp Val Met Val Asp Arg His
        515                 520                 525 aag gtg gcc ttg ggg aag acc ctg gga gag gga gaa ttt ggt gct gtg     1632
Lys Val Ala Leu Gly Lys Thr Leu Gly Glu Gly Glu Phe Gly Ala Val
    530                 535                 540 atg gag ggc cag ctc aac cag gat gac tcc atc ctc aag gtc gct gtg     1680
Met Glu Gly Gln Leu Asn Gln Asp Asp Ser Ile Leu Lys Val Ala Val
545                 550                 555                 560 aag acc atg aaa att gcc atc tgc aca aga tca gag ctg gag gat ttc     1728
Lys Thr Met Lys Ile Ala Ile Cys Thr Arg Ser Glu Leu Glu Asp Phe
                565                 570                 575 ctg agt gaa gct gtc tgc atg aag gaa ttt gac cac ccc aac gtc atg     1776
Leu Ser Glu Ala Val Cys Met Lys Glu Phe Asp His Pro Asn Val Met
```

```
         Leu Ser Glu Ala Val Cys Met Lys Glu Phe Asp His Pro Asn Val Met
                     580                 585                 590 agg ctc att ggc gtc tgt ttc cag ggt tct gac cga gag ggt ttc cca    1824
         Arg Leu Ile Gly Val Cys Phe Gln Gly Ser Asp Arg Glu Gly Phe Pro
                     595                 600                 605 gaa ccg gtg gtc atc ttg cct ttc atg aaa cat gga gac ctc cac agt    1872
         Glu Pro Val Val Ile Leu Pro Phe Met Lys His Gly Asp Leu His Ser
             610                 615                 620 ttc ctc ctg tac tcg cgg ctc ggg gac cag cca gtg ttc ctg ccc act    1920
         Phe Leu Leu Tyr Ser Arg Leu Gly Asp Gln Pro Val Phe Leu Pro Thr
         625                 630                 635                 640 cag atg cta gtg aag ttt atg gcc gac att gcc agt ggc atg gag tac    1968
         Gln Met Leu Val Lys Phe Met Ala Asp Ile Ala Ser Gly Met Glu Tyr
                         645                 650                 655 ctc agt acc aag aga ttc ata cac cgg gac cta gct gcc agg aac tgc    2016
         Leu Ser Thr Lys Arg Phe Ile His Arg Asp Leu Ala Ala Arg Asn Cys
                     660                 665                 670 atg ctg aat gag aac atg tcc gtg tgc gtg gca gac ttc ggg ctc tcc    2064
         Met Leu Asn Glu Asn Met Ser Val Cys Val Ala Asp Phe Gly Leu Ser
                 675                 680                 685 aag aag atc tac aat ggg gat tac tac cgc caa ggg cgc att gcc aag    2112
         Lys Lys Ile Tyr Asn Gly Asp Tyr Tyr Arg Gln Gly Arg Ile Ala Lys
             690                 695                 700 atg cca gtc aag tgg att gct atc gag agt ctg gca gat cga gtc tac    2160
         Met Pro Val Lys Trp Ile Ala Ile Glu Ser Leu Ala Asp Arg Val Tyr
         705                 710                 715                 720 acc agc aag agt gac gtg tgg tcc ttc ggt gtg aca atg tgg gag atc    2208
         Thr Ser Lys Ser Asp Val Trp Ser Phe Gly Val Thr Met Trp Glu Ile
                         725                 730                 735 gcc acc cga ggc caa act ccc tat cca ggg gtg gag aac agt gag att    2256
         Ala Thr Arg Gly Gln Thr Pro Tyr Pro Gly Val Glu Asn Ser Glu Ile
                     740                 745                 750 tac gac tac cta cgt caa gga aat cgc ctg aaa cag cct ctg gac tgt    2304
         Tyr Asp Tyr Leu Arg Gln Gly Asn Arg Leu Lys Gln Pro Leu Asp Cys
                 755                 760                 765 ctg gat ggc ctc tat gcc ctg atg tcc cgg tgc tgg gag ctg aac cct    2352
         Leu Asp Gly Leu Tyr Ala Leu Met Ser Arg Cys Trp Glu Leu Asn Pro
             770                 775                 780 cga gac cgg cca agt ttt gca gag ctc cgg gaa gac ttg gag aac aca    2400
         Arg Asp Arg Pro Ser Phe Ala Glu Leu Arg Glu Asp Leu Glu Asn Thr
         785                 790                 795                 800 ttg aag gct cta ccc cct gct cag gag cct gat gaa atc ctc tat gtc    2448
         Leu Lys Ala Leu Pro Pro Ala Gln Glu Pro Asp Glu Ile Leu Tyr Val
                         805                 810                 815 aac atg gat gag ggc gga agt cac ctt gaa ccc cgt ggg gct gct gga    2496
         Asn Met Asp Glu Gly Gly Ser His Leu Glu Pro Arg Gly Ala Ala Gly
                     820                 825                 830 gga gct gac ccc cca acc caa cct gat cct aag gat tac tgt agc tgt    2544
         Gly Ala Asp Pro Pro Thr Gln Pro Asp Pro Lys Asp Tyr Cys Ser Cys
                 835                 840                 845 ctc act gca gct gac gtc cac tca gct gga cgc tat gtc ctt tgt cct    2592
         Leu Thr Ala Ala Asp Val His Ser Ala Gly Arg Tyr Val Leu Cys Pro
         850                 855                 860 tct aca gcc cca gga ccc act ctg tct gct gac aga ggc tgc cca gca    2640
         Ser Thr Ala Pro Gly Pro Thr Leu Ser Ala Asp Arg Gly Cys Pro Ala
         865                 870                 875                 880 cct cca ggg cag gag gac gga gcc tga                                2667
         Pro Pro Gly Gln Glu Asp Gly Ala
                         885
```

<210> SEQ ID NO 8
<211> LENGTH: 888
<212> TYPE: PRT
<213> ORGANISM: Rattus norvegicus

<400> SEQUENCE: 8

```
Met Gly Arg Val Pro Leu Ala Trp Cys Val Ala Leu Cys Cys Trp Gly
1               5                   10                  15

Cys Ala Ala Pro Lys Asp Thr Gln Thr Glu Ala Asp Ser Pro Phe Val
            20                  25                  30

Gly Asn Pro Gly Asn Ile Thr Gly Ala Arg Gly Leu Thr Gly Thr Leu
        35                  40                  45

Arg Cys Glu Leu Gln Val Gln Gly Glu Pro Pro Glu Val Met Trp Leu
    50                  55                  60

Arg Asp Gly Gln Ile Leu Glu Leu Ala Asp Asn Thr Gln Thr Gln Val
65                  70                  75                  80

Pro Leu Gly Glu Asp Trp Gln Asp Glu Trp Lys Val Val Ser Gln Leu
                85                  90                  95

Arg Ile Ser Ala Leu Gln Leu Ser Asp Ala Gly Glu Tyr Gln Cys Met
            100                 105                 110

Val His Leu Glu Gly Arg Thr Phe Val Ser Gln Pro Gly Phe Val Gly
        115                 120                 125

Leu Glu Gly Leu Pro Tyr Phe Leu Glu Glu Pro Glu Asp Lys Ala Val
    130                 135                 140

Pro Ala Asn Thr Pro Phe Asn Leu Ser Cys Gln Ala Gln Gly Pro Pro
145                 150                 155                 160

Glu Pro Val Thr Leu Leu Trp Leu Gln Asp Ala Val Pro Leu Ala Pro
                165                 170                 175

Val Ala Gly Tyr Ser Phe Gln His Ser Leu Gln Ala Pro Gly Leu Asn
            180                 185                 190

Lys Thr Ser Ser Phe Ser Cys Glu Ala His Asn Ala Lys Gly Val Thr
        195                 200                 205

Thr Ser Arg Thr Ala Thr Ile Thr Val Leu Pro Gln Arg Pro His Asn
    210                 215                 220

Leu His Val Val Ser Arg His Pro Thr Glu Leu Glu Val Ala Trp Ile
225                 230                 235                 240

Pro Thr Leu Ser Gly Ile Tyr Pro Leu Thr His Cys Thr Leu Gln Ala
                245                 250                 255

Val Leu Ser Asn Asp Gly Val Gly Val Trp Leu Gly Lys Ser Asp Pro
            260                 265                 270

Pro Glu Glu Pro Leu Thr Val Gln Val Ser Val Pro Pro His Gln Leu
        275                 280                 285

Arg Leu Glu Lys Leu Leu Pro His Thr Pro Tyr His Ile Arg Val Ser
    290                 295                 300

Cys Thr Ser Ser Gln Gly Pro Ser Pro Trp Thr His Trp Leu Pro Val
305                 310                 315                 320

Glu Thr Thr Glu Gly Val Pro Leu Gly Pro Pro Glu Asn Val Ser Ala
                325                 330                 335

Met Arg Asn Gly Ser Gln Ala Leu Val Arg Trp Gln Glu Pro Arg Glu
            340                 345                 350

Pro Leu Gln Gly Thr Leu Leu Gly Tyr Arg Leu Ala Tyr Arg Gly Gln
        355                 360                 365

Asp Thr Pro Glu Val Leu Met Asp Ile Gly Leu Thr Arg Glu Val Thr
    370                 375                 380

Leu Glu Leu Arg Gly Asp Arg Pro Val Ala Asn Leu Thr Val Ser Val
```

```
             385                 390                 395                 400
Ala Ala Tyr Thr Ser Ala Gly Asp Gly Pro Trp Ser Leu Pro Val Pro
                405                 410                 415

Leu Glu Pro Trp Arg Pro Gly Gln Gly Gln Pro Leu His His Leu Val
                420                 425                 430

Ser Glu Pro Pro Pro Ala Phe Ser Trp Pro Trp Trp Tyr Val Leu
                435                 440                 445

Leu Gly Ala Leu Val Ala Ala Cys Val Leu Ile Leu Thr Leu Phe
    450                 455                 460

Leu Val His Arg Arg Lys Lys Glu Thr Arg Tyr Gly Glu Val Phe Glu
465                 470                 475                 480

Pro Thr Val Glu Arg Gly Glu Leu Val Val Arg Tyr Arg Ala Arg Lys
                485                 490                 495

Ser Tyr Ser Arg Arg Thr Thr Glu Ala Thr Leu Asn Ser Leu Gly Ile
                500                 505                 510

Ser Glu Glu Leu Lys Glu Lys Leu Arg Asp Val Met Val Asp Arg His
            515                 520                 525

Lys Val Ala Leu Gly Lys Thr Leu Gly Glu Gly Glu Phe Gly Ala Val
    530                 535                 540

Met Glu Gly Gln Leu Asn Gln Asp Asp Ser Ile Leu Lys Val Ala Val
545                 550                 555                 560

Lys Thr Met Lys Ile Ala Ile Cys Thr Arg Ser Glu Leu Glu Asp Phe
                565                 570                 575

Leu Ser Glu Ala Val Cys Met Lys Glu Phe Asp His Pro Asn Val Met
                580                 585                 590

Arg Leu Ile Gly Val Cys Phe Gln Gly Ser Asp Arg Glu Gly Phe Pro
                595                 600                 605

Glu Pro Val Val Ile Leu Pro Phe Met Lys His Gly Asp Leu His Ser
    610                 615                 620

Phe Leu Leu Tyr Ser Arg Leu Gly Asp Gln Pro Val Phe Leu Pro Thr
625                 630                 635                 640

Gln Met Leu Val Lys Phe Met Ala Asp Ile Ala Ser Gly Met Glu Tyr
                645                 650                 655

Leu Ser Thr Lys Arg Phe Ile His Arg Asp Leu Ala Ala Arg Asn Cys
                660                 665                 670

Met Leu Asn Glu Asn Met Ser Val Cys Val Ala Asp Phe Gly Leu Ser
            675                 680                 685

Lys Lys Ile Tyr Asn Gly Asp Tyr Tyr Arg Gln Gly Arg Ile Ala Lys
    690                 695                 700

Met Pro Val Lys Trp Ile Ala Ile Glu Ser Leu Ala Asp Arg Val Tyr
705                 710                 715                 720

Thr Ser Lys Ser Asp Val Trp Ser Phe Gly Val Thr Met Trp Glu Ile
                725                 730                 735

Ala Thr Arg Gly Gln Thr Pro Tyr Pro Gly Val Glu Asn Ser Glu Ile
            740                 745                 750

Tyr Asp Tyr Leu Arg Gln Gly Asn Arg Leu Lys Gln Pro Leu Asp Cys
            755                 760                 765

Leu Asp Gly Leu Tyr Ala Leu Met Ser Arg Cys Trp Glu Leu Asn Pro
    770                 775                 780

Arg Asp Arg Pro Ser Phe Ala Glu Leu Arg Glu Asp Leu Glu Asn Thr
785                 790                 795                 800

Leu Lys Ala Leu Pro Pro Ala Gln Glu Pro Asp Glu Ile Leu Tyr Val
                805                 810                 815
```

```
Asn Met Asp Glu Gly Gly Ser His Leu Glu Pro Arg Gly Ala Ala Gly
            820                 825                 830

Gly Ala Asp Pro Pro Thr Gln Pro Asp Pro Lys Asp Tyr Cys Ser Cys
            835                 840                 845

Leu Thr Ala Ala Asp Val His Ser Ala Gly Arg Tyr Val Leu Cys Pro
        850                 855                 860

Ser Thr Ala Pro Gly Pro Thr Leu Ser Ala Asp Arg Gly Cys Pro Ala
865                 870                 875                 880

Pro Pro Gly Gln Glu Asp Gly Ala
                885

<210> SEQ ID NO 9
<211> LENGTH: 4961
<212> TYPE: DNA
<213> ORGANISM: Gallus gallus
<220> FEATURE:
<221> NAME/KEY: CDS
<222> LOCATION: (229)..(2850)

<400> SEQUENCE: 9
```

| | | |
|---|---|---|
| agcgcggtgg cggagggccg ggcccggccc cggaggaggc gccgcgcggc cgcgcgccga | 60 |
| taggggagag cgcccggca ctcagcgccc ggcggcggca ccgcaccgca ccgcgttcgg | 120 |
| agcgccgctg cccggccgga gccgccgcgg aacttggagc gttcccacag cgtcccagcg | 180 |
| cggcccggcg gagccgagga gccggggggag gatggtggtg cgggagag atg gag ctg | 237 |

```
                                                  Met Glu Leu
                                                    1 agg cgg agc atg gcg ctg ccg cgg ctc ctc ttg ctg gga ctg tgg gct    285
Arg Arg Ser Met Ala Leu Pro Arg Leu Leu Leu Leu Gly Leu Trp Ala
    5                   10                  15 gcg gcg ctt cgg gac ggc gcc gtg gcg gca ggt atg aag ttt aca gga    333
Ala Ala Leu Arg Asp Gly Ala Val Ala Ala Gly Met Lys Phe Thr Gly
20                  25                  30                  35 tct cca atc aaa tta aag gtg tcc cag ggt caa ccc gtc aaa cta aat    381
Ser Pro Ile Lys Leu Lys Val Ser Gln Gly Gln Pro Val Lys Leu Asn
                40                  45                  50 tgc agc ctg gag gga atg gaa gat ccc gag atg ttg tgg atc aag gac    429
Cys Ser Leu Glu Gly Met Glu Asp Pro Glu Met Leu Trp Ile Lys Asp
            55                  60                  65 gga gca gtg gtg caa agc gta gac cag gtg tac att cca gta gat gaa    477
Gly Ala Val Val Gln Ser Val Asp Gln Val Tyr Ile Pro Val Asp Glu
        70                  75                  80 gat cac tgg atc ggc ttc ctc agc ctg aaa tcc gtc gag agg aca gat    525
Asp His Trp Ile Gly Phe Leu Ser Leu Lys Ser Val Glu Arg Thr Asp
    85                  90                  95 tct ggg aag tac tgg tgc cag gtt gag aac ggg ggg aag aag gaa gaa    573
Ser Gly Lys Tyr Trp Cys Gln Val Glu Asn Gly Gly Lys Lys Glu Glu
100                 105                 110                 115 tca cag caa gtg tgg ctc ata gtg gaa ggt gtg ccc tac ttt act gtg    621
Ser Gln Gln Val Trp Leu Ile Val Glu Gly Val Pro Tyr Phe Thr Val
                120                 125                 130 gaa cct gag gat gtg tcc gtg tcc cct aat gcc cca ttt cat atg gcc    669
Glu Pro Glu Asp Val Ser Val Ser Pro Asn Ala Pro Phe His Met Ala
            135                 140                 145 tgt gct gct gtt ggt ccc cct gaa cca gtg aca att gtc tgg tgg atg    717
Cys Ala Ala Val Gly Pro Pro Glu Pro Val Thr Ile Val Trp Trp Met
        150                 155                 160 gga gac tct aga gtg ggg ctt cca gac atc tcc ccc tcc atc cta aac    765
Gly Asp Ser Arg Val Gly Leu Pro Asp Ile Ser Pro Ser Ile Leu Asn
    165                 170                 175
```

| | | |
|---|---|---|
| gtg tca ggt att aat caa agc aca atg ttc tcc tgc gaa gct cac aac<br>Val Ser Gly Ile Asn Gln Ser Thr Met Phe Ser Cys Glu Ala His Asn<br>180                      185                     190                  195 | 813 |
| gta aag gga ttg tct tca tct cgg aca gcc act gtt cag att aaa gcc<br>Val Lys Gly Leu Ser Ser Ser Arg Thr Ala Thr Val Gln Ile Lys Ala<br>                    200                     205                    210 | 861 |
| atg cct ctg cca ccc ctc aac gtg acg gtg agc cag gtc acc agc agc<br>Met Pro Leu Pro Pro Leu Asn Val Thr Val Ser Gln Val Thr Ser Ser<br>              215                     220                    225 | 909 |
| aat gcc agt gtg gtc tgg gtg ccg ggg ttt gat ggc cgt gct ccc ctc<br>Asn Ala Ser Val Val Trp Val Pro Gly Phe Asp Gly Arg Ala Pro Leu<br>        230                     235                    240 | 957 |
| cat tct tgc act ctt cag gtt gct gag tcc cca gat ggc cag gag gtc<br>His Ser Cys Thr Leu Gln Val Ala Glu Ser Pro Asp Gly Gln Glu Val<br>245                      250                     255 | 1005 |
| tcc acc gaa gtc gcc cca gtg cct ccc ttt gcc tat ggc gtg cag ggc<br>Ser Thr Glu Val Ala Pro Val Pro Pro Phe Ala Tyr Gly Val Gln Gly<br>260                      265                     270                    275 | 1053 |
| ctg aag cac tcc acc aac tac agt gtt cgt gtg cag tgc agc aat gag<br>Leu Lys His Ser Thr Asn Tyr Ser Val Arg Val Gln Cys Ser Asn Glu<br>                         280                     285                    290 | 1101 |
| atg ggc agc tcc cct ttc aca gag aga gtt tac ttc cag aca ctg gag<br>Met Gly Ser Ser Pro Phe Thr Glu Arg Val Tyr Phe Gln Thr Leu Glu<br>                295                     300                    305 | 1149 |
| ctt gct cca agc agc acc caa aat atc cat gtg atc caa agg gat<br>Leu Ala Pro Ser Ser Thr Pro Gln Asn Ile His Val Ile Gln Arg Asp<br>310                      315                     320 | 1197 |
| cct ggt ttg gtt ttg gag tgg gaa ggc gtg gct cca gac gtg ctg aaa<br>Pro Gly Leu Val Leu Glu Trp Glu Gly Val Ala Pro Asp Val Leu Lys<br>325                      330                     335 | 1245 |
| gaa aat gtc ctg gga tac agg ctg gag tgg att cag gat aat gtg act<br>Glu Asn Val Leu Gly Tyr Arg Leu Glu Trp Ile Gln Asp Asn Val Thr<br>340                      345                     350                    355 | 1293 |
| cag ggg gag atg atc gtg cag gat aca aaa gca aat ctc aca acg tgg<br>Gln Gly Glu Met Ile Val Gln Asp Thr Lys Ala Asn Leu Thr Thr Trp<br>                    360                     365                    370 | 1341 |
| aac cct ctc aaa gac cta atc atc agg gtg tgt gtg ctg aac tcg gct<br>Asn Pro Leu Lys Asp Leu Ile Ile Arg Val Cys Val Leu Asn Ser Ala<br>                375                     380                    385 | 1389 |
| ggg tgc gga cca tgg agt gac ctc ttc ctg ctg gaa gcc cag gag gtc<br>Gly Cys Gly Pro Trp Ser Asp Leu Phe Leu Leu Glu Ala Gln Glu Val<br>              390                     395                    400 | 1437 |
| atg ggt ggt cag aga cag cct cct tat ggg aca tcc tgg gtt cct gtg<br>Met Gly Gly Gln Arg Gln Pro Pro Tyr Gly Thr Ser Trp Val Pro Val<br>405                      410                     415 | 1485 |
| gca ttg ggc att ctc aca gct ctg gtc aca gct gtt gcc ttg gct ctt<br>Ala Leu Gly Ile Leu Thr Ala Leu Val Thr Ala Val Ala Leu Ala Leu<br>420                      425                     430                    435 | 1533 |
| att ctc ctt cga aaa aga aga aag gaa act cga ttt ggc cat gcc ttt<br>Ile Leu Leu Arg Lys Arg Arg Lys Glu Thr Arg Phe Gly His Ala Phe<br>                    440                     445                    450 | 1581 |
| ggt agt gtg gtt ggc aga ggg gat cca gct gtc cat ttc aga gct gcc<br>Gly Ser Val Val Gly Arg Gly Asp Pro Ala Val His Phe Arg Ala Ala<br>                455                     460                    465 | 1629 |
| agg tct ttc aac agg gag ggc cca gag ctc att gaa gca aca ttg gag<br>Arg Ser Phe Asn Arg Glu Gly Pro Glu Leu Ile Glu Ala Thr Leu Glu<br>              470                     475                    480 | 1677 |
| agt gta ggg atc agt gat gag ctg aag aca aaa ctg aaa gat gtc ctt<br>Ser Val Gly Ile Ser Asp Glu Leu Lys Thr Lys Leu Lys Asp Val Leu<br>485                      490                     495 | 1725 |

```
atc cag gag cag cag ttc acc ttg gga cga atg tta ggc aaa gga gag    1773
Ile Gln Glu Gln Gln Phe Thr Leu Gly Arg Met Leu Gly Lys Gly Glu
500                 505                 510                 515 ttt ggg tca gtt cga gag gca cta ctg aag cta gat gat ggc tct ttc    1821
Phe Gly Ser Val Arg Glu Ala Leu Leu Lys Leu Asp Asp Gly Ser Phe
                520                 525                 530 cag aaa gtg gca gtt aag atg ctg aaa gcg gac atc ttc acc tcc act    1869
Gln Lys Val Ala Val Lys Met Leu Lys Ala Asp Ile Phe Thr Ser Thr
535                 540                 545 gac atc gag gag ttc ctg cgg gag gct gcg tgt atg aag gag ttt gac    1917
Asp Ile Glu Glu Phe Leu Arg Glu Ala Ala Cys Met Lys Glu Phe Asp
        550                 555                 560 cac cca cat gtc act aag ctg att gga gtc agt cta cgg agc cgt ccc    1965
His Pro His Val Thr Lys Leu Ile Gly Val Ser Leu Arg Ser Arg Pro
565                 570                 575 aag ggc cgt ctc cca att ccc atg gtg atc ctg ccc ttc atg aag cat    2013
Lys Gly Arg Leu Pro Ile Pro Met Val Ile Leu Pro Phe Met Lys His
580                 585                 590                 595 gga gac ctt cat gct ttt ctg ctg atg tca agg atc ggg gaa aac cct    2061
Gly Asp Leu His Ala Phe Leu Leu Met Ser Arg Ile Gly Glu Asn Pro
            600                 605                 610 ttt aac ttg cct ctt cag aca ctc ctc aag ttc atg att gac att gcc    2109
Phe Asn Leu Pro Leu Gln Thr Leu Leu Lys Phe Met Ile Asp Ile Ala
                615                 620                 625 agt ggg atg gag tac ttg agc tca aaa aat ttc ata cac aga gac ctt    2157
Ser Gly Met Glu Tyr Leu Ser Ser Lys Asn Phe Ile His Arg Asp Leu
                630                 635                 640 gca gct cgg aac tgc atg ctg gat gag aac atg aat gtg agt gtt gca    2205
Ala Ala Arg Asn Cys Met Leu Asp Glu Asn Met Asn Val Ser Val Ala
645                 650                 655 gac ttc ggc ctt tct aag aaa atc tac agt gga gac tac tac cgt cag    2253
Asp Phe Gly Leu Ser Lys Lys Ile Tyr Ser Gly Asp Tyr Tyr Arg Gln
660                 665                 670                 675 ggc tgt gcc tcc aag ctg cca gtg aag tgg ctt gct ctg gaa agc ctg    2301
Gly Cys Ala Ser Lys Leu Pro Val Lys Trp Leu Ala Leu Glu Ser Leu
                680                 685                 690 gcg gat aat ctg tac aca aca cac agc gat gtg tgg gcg ttt ggg gtg    2349
Ala Asp Asn Leu Tyr Thr Thr His Ser Asp Val Trp Ala Phe Gly Val
                695                 700                 705 acc atg tgg gag att gtg acc cga ggg caa acc cct tat gct ggc att    2397
Thr Met Trp Glu Ile Val Thr Arg Gly Gln Thr Pro Tyr Ala Gly Ile
            710                 715                 720 gag aat gca gaa atc tac aac tac ctc atc agt ggg aac agg ctg aag    2445
Glu Asn Ala Glu Ile Tyr Asn Tyr Leu Ile Ser Gly Asn Arg Leu Lys
725                 730                 735 cag cca ccg gag tgc ctg gaa gat gtc tac gat ctc atg tgc aga tgt    2493
Gln Pro Pro Glu Cys Leu Glu Asp Val Tyr Asp Leu Met Cys Arg Cys
740                 745                 750                 755 tgg cat cct gag ccc aag cta cgc cca agc ttt gga gtg ctc cgg tcc    2541
Trp His Pro Glu Pro Lys Leu Arg Pro Ser Phe Gly Val Leu Arg Ser
                760                 765                 770 cag ctg gaa atg att cgg ggg agg atg tcc aca ctc tcc tta agc caa    2589
Gln Leu Glu Met Ile Arg Gly Arg Met Ser Thr Leu Ser Leu Ser Gln
            775                 780                 785 gac cct ctc tat gtc aac att ggg aag gac aaa gag tca tct gtc agt    2637
Asp Pro Leu Tyr Val Asn Ile Gly Lys Asp Lys Glu Ser Ser Val Ser
                790                 795                 800 gac cct gcc gtg cac acc tct ttt gga aac acg gac ggt gat gag acc    2685
Asp Pro Ala Val His Thr Ser Phe Gly Asn Thr Asp Gly Asp Glu Thr
805                 810                 815
```

| | | | | | | | | | | | | | | | | |
|---|---|---|---|---|---|---|---|---|---|---|---|---|---|---|---|---|
| att | gct | ggg | gca | gca | gct | gct | gcc | atc | acg | agt | gac | tat | cgc | tac | atc | 2733 |
| Ile | Ala | Gly | Ala | Ala | Ala | Ala | Ala | Ile | Thr | Ser | Asp | Tyr | Arg | Tyr | Ile | |
| 820 | | | | | 825 | | | | | 830 | | | | | 835 | |
| atg | agc | ccc | ttg | tgc | ctt | gga | gat | gat | gtc | gag | ggt | gaa | agg | cat | cca | 2781 |
| Met | Ser | Pro | Leu | Cys | Leu | Gly | Asp | Asp | Val | Glu | Gly | Glu | Arg | His | Pro | |
| | | | | 840 | | | | | 845 | | | | | 850 | | |
| gaa | ggg | cag | gaa | ggg | gag | aac | aaa | agc | ctt | ctg | tat | gag | ctg | gag | aca | 2829 |
| Glu | Gly | Gln | Glu | Gly | Glu | Asn | Lys | Ser | Leu | Leu | Tyr | Glu | Leu | Glu | Thr | |
| | | 855 | | | | | 860 | | | | | 865 | | | | |

| | | | | | | | |
|---|---|---|---|---|---|---|---|
| gaa | gga | gag | aaa | agt | tgt | tag tctgtacata gcagtgacac tctgcttccc | 2880 |
| Glu | Gly | Glu | Lys | Ser | Cys | | |
| | | 870 | | | | | | tgggacggga tgtgtgcagc cacagtgccg cgtcgcctga gtcttcgatg ccggatctgg    2940
agtggcttta acagcacag gctggagctc ttgggcagct ttggcagctt tcatttctgt    3000
atgggctgca gttgcggaca gcttggatgg accgcagccc tgacatgccc ttggatttgg    3060
ggagggaggc ggtagggtgg caggctgttc acatcccgca gaaagaaggt caaagccaag    3120
gtgggcagtc agagcctctg ctctggtctt tctcactggc agctggagca gagctgaacg    3180
caccttctgt tcggtcagtg ctcgctctcg tgtagatgtt gtctttgatc ctggctgcgt    3240
gacttcggga ctggtacctc tgaaaacact agtgggtatt tacaccgtca tcaggacacc    3300
gggggaagtt cctcttgtgt tcactcagca gtgctgccta gacgtcttgc ctacctcagt    3360
ggttctcaaa ctacgatctg cagatctgca ttcacccgac attgaacatc tggcacattt    3420
catgcagtaa tgctcgctgc tccctctacc cagggctctt ttaaggtact cagacttgca    3480
gtgagcaatg aaattagaaa aaaaaaaaga aaatggagca tccctctctg ccccacatgc    3540
ctcttttatg tgttttttctt tctgtttggt gccggtttag gcctgaccaa ccttgcagtt    3600
ggccttcaaa tgggaaggga gggagagcag ctggcatggg tgagggcaga atctaacttc    3660
aaaggaattg agaggaaact gtgtagagag acttgtcgg cagtgtgggg aagcagtgct    3720
aattaatgca aaatgctgcc ctccaggaga ggaaggagca tgcttagata gagaatggcg    3780
gacacgcatc actttcagca ggagcaggat tcagcatttg cttgaaagta ggattccttt    3840
aatctttctc tttttaacca tcctctgact ttttcaaaca atccagtgct gtagctgctg    3900
tggtgaaggt ctgaagtcag tttggggaag gtatgtgtga gatggggga agggaccaac    3960
cgggaaatct ctttctaaag agagaatcct tatcacgaaa aagcttgaga ccactggcc     4020
gtcttattta ggaggtcttc tggcacactg taaaagccac atcagatcat agacccgtat    4080
caccgcagcc ttcacgcag gcaaaattg atggttttgc tctttgggtt ttgtttccca     4140
atcagcatgt ctgactcact gtaactgcaa gtgcttttgt ggtttttaat aatttaatat    4200
tttaatgtaa aatcagcatt tgttttgtgc agtgtttccc agcaaggaag tgcagctaca    4260
tcttactcta gttatcctaa atatttgcta gatcttcatt tgttttattt tcagcgtgct    4320
gaaaactcag cagtaccaca ggacttagga ttccacactg cttttcctca gacacaaata    4380
ccaccaacgt cgtcgcttgc caggttggcg aaggtggaac caatgagcca gttagactg     4440
caggctcagt atcaggacac cctaccattc gatgccccgt tcttggctgt tgccgggtga    4500
ggggctcact gcaaaatttg gtccagtttt catcccttgc tgagagcacc ttcctgcgga    4560
agggaaagtt cagcctgggg cttgggcatg ggtccttttct gtaagatttc ctactaccca   4620
acgctgccct acagctggaa gcccagtatg gtttcttggt cacaaactgc aaaacattac    4680
accccaggca gtacgggttt ttttccatca tttagctgga tcgctgtcaa tgcaggtgag    4740
aaaataacag ctaacgaagg ttagcagaaa cgtgtgcggt gcacacattg gcagtgaggg    4800

-continued

```
cagaaggctg tgctccctgt aactgcctgg gaagcgcaga tgtacataga gactctaact    4860
ttgggaagca tgtcatagtt tttatgcatt tttttaaata ataaaacatg tactgtgtct    4920
gaaaaaaaaa aaaaaaaaaa aaaaaaaaaa aaaaaaaaaa a                        4961
```

<210> SEQ ID NO 10
<211> LENGTH: 873
<212> TYPE: PRT
<213> ORGANISM: Gallus gallus

<400> SEQUENCE: 10

```
Met Glu Leu Arg Arg Ser Met Ala Leu Pro Arg Leu Leu Leu Leu Gly
1               5                   10                  15

Leu Trp Ala Ala Ala Leu Arg Asp Gly Ala Val Ala Ala Gly Met Lys
            20                  25                  30

Phe Thr Gly Ser Pro Ile Lys Leu Lys Val Ser Gln Gly Gln Pro Val
        35                  40                  45

Lys Leu Asn Cys Ser Leu Glu Gly Met Glu Asp Pro Glu Met Leu Trp
    50                  55                  60

Ile Lys Asp Gly Ala Val Val Gln Ser Val Asp Gln Val Tyr Ile Pro
65                  70                  75                  80

Val Asp Glu Asp His Trp Ile Gly Phe Leu Ser Leu Lys Ser Val Glu
                85                  90                  95

Arg Thr Asp Ser Gly Lys Tyr Trp Cys Gln Val Glu Asn Gly Gly Lys
            100                 105                 110

Lys Glu Glu Ser Gln Gln Val Trp Leu Ile Val Glu Gly Val Pro Tyr
        115                 120                 125

Phe Thr Val Glu Pro Glu Asp Val Ser Val Ser Pro Asn Ala Pro Phe
    130                 135                 140

His Met Ala Cys Ala Ala Val Gly Pro Pro Glu Pro Val Thr Ile Val
145                 150                 155                 160

Trp Trp Met Gly Asp Ser Arg Val Gly Leu Pro Asp Ile Ser Pro Ser
                165                 170                 175

Ile Leu Asn Val Ser Gly Ile Asn Gln Ser Thr Met Phe Ser Cys Glu
            180                 185                 190

Ala His Asn Val Lys Gly Leu Ser Ser Ser Arg Thr Ala Thr Val Gln
        195                 200                 205

Ile Lys Ala Met Pro Leu Pro Pro Leu Asn Val Thr Val Ser Gln Val
    210                 215                 220

Thr Ser Ser Asn Ala Ser Val Val Trp Val Pro Gly Phe Asp Gly Arg
225                 230                 235                 240

Ala Pro Leu His Ser Cys Thr Leu Gln Val Ala Glu Ser Pro Asp Gly
                245                 250                 255

Gln Glu Val Ser Thr Glu Val Ala Pro Val Pro Phe Ala Tyr Gly
            260                 265                 270

Val Gln Gly Leu Lys His Ser Thr Asn Tyr Ser Val Arg Val Gln Cys
        275                 280                 285

Ser Asn Glu Met Gly Ser Ser Pro Phe Thr Glu Arg Val Tyr Phe Gln
    290                 295                 300

Thr Leu Glu Leu Ala Pro Ser Ser Thr Pro Gln Asn Ile His Val Ile
305                 310                 315                 320

Gln Arg Asp Pro Gly Leu Val Leu Glu Trp Glu Val Ala Pro Asp
                325                 330                 335

Val Leu Lys Glu Asn Val Leu Gly Tyr Arg Leu Glu Trp Ile Gln Asp
            340                 345                 350
```

```
Asn Val Thr Gln Gly Glu Met Ile Val Gln Asp Thr Lys Ala Asn Leu
        355                 360                 365

Thr Thr Trp Asn Pro Leu Lys Asp Leu Ile Ile Arg Val Cys Val Leu
    370                 375                 380

Asn Ser Ala Gly Cys Gly Pro Trp Ser Asp Leu Phe Leu Leu Glu Ala
385                 390                 395                 400

Gln Glu Val Met Gly Gly Gln Arg Gln Pro Pro Tyr Gly Thr Ser Trp
                405                 410                 415

Val Pro Val Ala Leu Gly Ile Leu Thr Ala Leu Val Thr Ala Val Ala
                420                 425                 430

Leu Ala Leu Ile Leu Leu Arg Lys Arg Lys Glu Thr Arg Phe Gly
        435                 440                 445

His Ala Phe Gly Ser Val Val Gly Arg Gly Asp Pro Ala Val His Phe
    450                 455                 460

Arg Ala Ala Arg Ser Phe Asn Arg Glu Gly Pro Glu Leu Ile Glu Ala
465                 470                 475                 480

Thr Leu Glu Ser Val Gly Ile Ser Asp Glu Leu Lys Thr Lys Leu Lys
                485                 490                 495

Asp Val Leu Ile Gln Glu Gln Phe Thr Leu Gly Arg Met Leu Gly
        500                 505                 510

Lys Gly Glu Phe Gly Ser Val Arg Glu Ala Leu Leu Lys Leu Asp Asp
    515                 520                 525

Gly Ser Phe Gln Lys Val Ala Val Lys Met Leu Lys Ala Asp Ile Phe
530                 535                 540

Thr Ser Thr Asp Ile Glu Glu Phe Leu Arg Glu Ala Ala Cys Met Lys
545                 550                 555                 560

Glu Phe Asp His Pro His Val Thr Lys Leu Ile Gly Val Ser Leu Arg
                565                 570                 575

Ser Arg Pro Lys Gly Arg Leu Pro Ile Pro Met Val Ile Leu Pro Phe
        580                 585                 590

Met Lys His Gly Asp Leu His Ala Phe Leu Leu Met Ser Arg Ile Gly
    595                 600                 605

Glu Asn Pro Phe Asn Leu Pro Leu Gln Thr Leu Leu Lys Phe Met Ile
610                 615                 620

Asp Ile Ala Ser Gly Met Glu Tyr Leu Ser Ser Lys Asn Phe Ile His
625                 630                 635                 640

Arg Asp Leu Ala Ala Arg Asn Cys Met Leu Asp Glu Asn Met Asn Val
                645                 650                 655

Ser Val Ala Asp Phe Gly Leu Ser Lys Lys Ile Tyr Ser Gly Asp Tyr
        660                 665                 670

Tyr Arg Gln Gly Cys Ala Ser Lys Leu Pro Val Lys Trp Leu Ala Leu
    675                 680                 685

Glu Ser Leu Ala Asp Asn Leu Tyr Thr Thr His Ser Asp Val Trp Ala
690                 695                 700

Phe Gly Val Thr Met Trp Glu Ile Val Thr Arg Gly Gln Thr Pro Tyr
705                 710                 715                 720

Ala Gly Ile Glu Asn Ala Glu Ile Tyr Asn Tyr Leu Ile Ser Gly Asn
                725                 730                 735

Arg Leu Lys Gln Pro Pro Glu Cys Leu Glu Asp Val Tyr Asp Leu Met
        740                 745                 750

Cys Arg Cys Trp His Pro Glu Pro Lys Leu Arg Pro Ser Phe Gly Val
    755                 760                 765

Leu Arg Ser Gln Leu Glu Met Ile Arg Gly Arg Met Ser Thr Leu Ser
770                 775                 780
```

```
Leu Ser Gln Asp Pro Leu Tyr Val Asn Ile Gly Lys Asp Lys Glu Ser
785                 790                 795                 800

Ser Val Ser Asp Pro Ala Val His Thr Ser Phe Gly Asn Thr Asp Gly
            805                 810                 815

Asp Glu Thr Ile Ala Gly Ala Ala Ala Ala Ile Thr Ser Asp Tyr
                820                 825                 830

Arg Tyr Ile Met Ser Pro Leu Cys Leu Gly Asp Asp Val Glu Gly Glu
                835                 840                 845

Arg His Pro Glu Gly Gln Glu Gly Glu Asn Lys Ser Leu Leu Tyr Glu
            850                 855                 860

Leu Glu Thr Glu Gly Glu Lys Ser Cys
865                 870

<210> SEQ ID NO 11
<211> LENGTH: 4510
<212> TYPE: DNA
<213> ORGANISM: Bos taurus
<220> FEATURE:
<221> NAME/KEY: CDS
<222> LOCATION: (1)..(3012)

<400> SEQUENCE: 11
```

| | | | | | | | | | | | | | | | | |
|---|---|---|---|---|---|---|---|---|---|---|---|---|---|---|---|---|
| atg | gga | cag | aca | gac | agg | aga | cgc | gga | ggg | cta | ggg | gct | ggg | ctt | gac | 48 |
| Met | Gly | Gln | Thr | Asp | Arg | Arg | Arg | Gly | Gly | Leu | Gly | Ala | Gly | Leu | Asp | |
| 1 | | | | 5 | | | | | 10 | | | | | 15 | | |
| ctg | ggg | gcc | tcg | cag | aga | ggg | gct | gag | cgg | agg | ctc | cct | ccc | atc | tcc | 96 |
| Leu | Gly | Ala | Ser | Gln | Arg | Gly | Ala | Glu | Arg | Arg | Leu | Pro | Pro | Ile | Ser | |
| | | | 20 | | | | | 25 | | | | | 30 | | | |
| ttt | tct | tcc | cca | cca | tcc | acc | agc | cca | gtc | tgt | gaa | gtc | tct | aga | gac | 144 |
| Phe | Ser | Ser | Pro | Pro | Ser | Thr | Ser | Pro | Val | Cys | Glu | Val | Ser | Arg | Asp | |
| | | 35 | | | | | 40 | | | | | 45 | | | | |
| cct | aag | cag | ggg | cag | gcc | agc | cgg | gca | gtc | agg | gcg | tgg | gag | gct | gcc | 192 |
| Pro | Lys | Gln | Gly | Gln | Ala | Ser | Arg | Ala | Val | Arg | Ala | Trp | Glu | Ala | Ala | |
| | 50 | | | | | 55 | | | | | 60 | | | | | |
| aga | tgc | tgg | gcc | tac | ttc | cca | acg | gga | tgg | agg | ccg | gac | ccc | agt | ccc | 240 |
| Arg | Cys | Trp | Ala | Tyr | Phe | Pro | Thr | Gly | Trp | Arg | Pro | Asp | Pro | Ser | Pro | |
| 65 | | | | | 70 | | | | | 75 | | | | | 80 | |
| ctg | gga | agg | ctc | cca | tcc | tcc | tca | cga | agc | ctc | cac | cct | ccg | ccc | ccc | 288 |
| Leu | Gly | Arg | Leu | Pro | Ser | Ser | Ser | Arg | Ser | Leu | His | Pro | Pro | Pro | Pro | |
| | | | | 85 | | | | | 90 | | | | | 95 | | |
| cag | ctg | agg | tca | ctc | aac | aac | tat | gtg | ggc | cta | agg | gcc | tgg | cgg | ggt | 336 |
| Gln | Leu | Arg | Ser | Leu | Asn | Asn | Tyr | Val | Gly | Leu | Arg | Ala | Trp | Arg | Gly | |
| | | | | | 100 | | | | | 105 | | | | | 110 | |
| cct | ggc | agc | cgt | agg | cag | gcc | ggc | agg | gat | gga | acc | gag | gag | tcc | agg | 384 |
| Pro | Gly | Ser | Arg | Arg | Gln | Ala | Gly | Arg | Asp | Gly | Thr | Glu | Glu | Ser | Arg | |
| | | | 115 | | | | | 120 | | | | | 125 | | | |
| gaa | gca | ggg | gtt | ccc | aag | cta | atg | ttc | ttc | cat | ctc | cct | gca | ggc | cca | 432 |
| Glu | Ala | Gly | Val | Pro | Lys | Leu | Met | Phe | Phe | His | Leu | Pro | Ala | Gly | Pro | |
| | 130 | | | | | 135 | | | | | 140 | | | | | |
| cag | act | gaa | gtg | tcc | ccc | ttt | gtg | ggg | agt | ccg | ggg | aac | atc | acc | ggt | 480 |
| Gln | Thr | Glu | Val | Ser | Pro | Phe | Val | Gly | Ser | Pro | Gly | Asn | Ile | Thr | Gly | |
| 145 | | | | | 150 | | | | | 155 | | | | | 160 | |
| gcc | cga | gga | ctc | atg | ggc | acc | ctt | cgg | tgt | gag | ctc | cag | gtt | cag | ggg | 528 |
| Ala | Arg | Gly | Leu | Met | Gly | Thr | Leu | Arg | Cys | Glu | Leu | Gln | Val | Gln | Gly | |
| | | | | 165 | | | | | 170 | | | | | 175 | | |
| gag | ccc | cct | gag | gtg | acc | tgg | ctt | cgg | gat | gga | cag | gtc | cta | gag | ctg | 576 |
| Glu | Pro | Pro | Glu | Val | Thr | Trp | Leu | Arg | Asp | Gly | Gln | Val | Leu | Glu | Leu | |
| | | | 180 | | | | | 185 | | | | | 190 | | | |
| gca | gac | agc | acc | cag | acc | cag | gtg | ccc | ctg | ggc | gaa | gac | ggg | cag | gat | 624 |
| Ala | Asp | Ser | Thr | Gln | Thr | Gln | Val | Pro | Leu | Gly | Glu | Asp | Gly | Gln | Asp | |

-continued

```
              195                 200                 205
gac tgg aaa gtg gtc agc caa ctc aga atc tcg tct ctg cag ctc tca      672
Asp Trp Lys Val Val Ser Gln Leu Arg Ile Ser Ser Leu Gln Leu Ser
210                 215                 220 gat gcg gga tgg tac cag tgc acg gtg gtc ctg gga gaa aag acc ttt      720
Asp Ala Gly Trp Tyr Gln Cys Thr Val Val Leu Gly Glu Lys Thr Phe
225                 230                 235                 240 gtg tct cag cct ggc tac gtg ggg ctg gaa ggc ctg cct tac ttc ctg      768
Val Ser Gln Pro Gly Tyr Val Gly Leu Glu Gly Leu Pro Tyr Phe Leu
                    245                 250                 255 gag gag cct gag gac agg act gtg gtt gcc aac act ccc ttc aac ctg      816
Glu Glu Pro Glu Asp Arg Thr Val Val Ala Asn Thr Pro Phe Asn Leu
            260                 265                 270 agc tgc cgg gcg cag gga ccc cca gag ccc gtg gac ctc ctc tgg ctc      864
Ser Cys Arg Ala Gln Gly Pro Pro Glu Pro Val Asp Leu Leu Trp Leu
        275                 280                 285 cag gat gct gtc tcc ctg gct tca gcc atg gac cac agc ccc cag cac      912
Gln Asp Ala Val Ser Leu Ala Ser Ala Met Asp His Ser Pro Gln His
    290                 295                 300 aca ctc cgt gtt cca ggc ctg aac aag act gcg tct ttc tcc tgt gaa      960
Thr Leu Arg Val Pro Gly Leu Asn Lys Thr Ala Ser Phe Ser Cys Glu
305                 310                 315                 320 gcc cac aat gcc aag ggg atc acc aca tcc cgc acg gcc acc atc aca     1008
Ala His Asn Ala Lys Gly Ile Thr Thr Ser Arg Thr Ala Thr Ile Thr
                    325                 330                 335 gtg ctc ccc cag cgg ccc cac gac ctc cac ttg gtt tcc acc cag ccg     1056
Val Leu Pro Gln Arg Pro His Asp Leu His Leu Val Ser Thr Gln Pro
            340                 345                 350 acg gaa ctg gag gtg gct tgg acc cca ggc ctg agt ggc atc tac ccc     1104
Thr Glu Leu Glu Val Ala Trp Thr Pro Gly Leu Ser Gly Ile Tyr Pro
        355                 360                 365 ctc acc cac tgc att ctg cag gct gtg ctg tca gat gac agg gtg ggc     1152
Leu Thr His Cys Ile Leu Gln Ala Val Leu Ser Asp Asp Arg Val Gly
    370                 375                 380 gcc tgg ctg gga gag cca gac ccc cca gag gag ccc ctc acc tta caa     1200
Ala Trp Leu Gly Glu Pro Asp Pro Pro Glu Glu Pro Leu Thr Leu Gln
385                 390                 395                 400 gca tcc gtt cct cct cat caa cta cgg ctg ggc agc ctc cat cct cac     1248
Ala Ser Val Pro Pro His Gln Leu Arg Leu Gly Ser Leu His Pro His
                    405                 410                 415 acc cct tac cac ctc cgg gtg gcc tgt gtc agt agc cag ggc ccc tca     1296
Thr Pro Tyr His Leu Arg Val Ala Cys Val Ser Ser Gln Gly Pro Ser
            420                 425                 430 ccc tgg acc cac tgg ctt cct gtg gag aca ccg gaa gga gaa tac tgg     1344
Pro Trp Thr His Trp Leu Pro Val Glu Thr Pro Glu Gly Glu Tyr Trp
        435                 440                 445 agt ggg ttg cca tgc cct cct cca ggg aat ctt cct gac ccc aga gat     1392
Ser Gly Leu Pro Cys Pro Pro Pro Gly Asn Leu Pro Asp Pro Arg Asp
    450                 455                 460 cca acc cac gtc tcc tgg atc aga ccc aaa tcc cct gca ttg caa ggt     1440
Pro Thr His Val Ser Trp Ile Arg Pro Lys Ser Pro Ala Leu Gln Gly
465                 470                 475                 480 gga ttc tta acc act gga cca cca ggg aca tcc cct cac act cct cct     1488
Gly Phe Leu Thr Thr Gly Pro Pro Gly Thr Ser Pro His Thr Pro Pro
                    485                 490                 495 cca acg tcc act cct ttc atg tcc atc gca tgc ccc gtc cag ccc tgt     1536
Pro Thr Ser Thr Pro Phe Met Ser Ile Ala Cys Pro Val Gln Pro Cys
            500                 505                 510 cca tca ccc aat gaa cct aca cct gcc tcc ctt caa cac cac ccc cct     1584
Pro Ser Pro Asn Glu Pro Thr Pro Ala Ser Leu Gln His His Pro Pro
```

```
                    515                 520                 525
ggg gac cca agg aac caa gac ctc cac cat gac ctg tct gcg tac ccc    1632
Gly Asp Pro Arg Asn Gln Asp Leu His His Asp Leu Ser Ala Tyr Pro
530                 535                 540 gtg aca gtg agt gaa ccc cca gcc ccc gcc ttc tcg tgg ccc tgg tgg    1680
Val Thr Val Ser Glu Pro Pro Ala Pro Ala Phe Ser Trp Pro Trp Trp
545                 550                 555                 560 tat gta ctg ctg gga gca gtg gtg gcc gcc gcc tgt gtc ctc atc ctg    1728
Tyr Val Leu Leu Gly Ala Val Val Ala Ala Ala Cys Val Leu Ile Leu
                565                 570                 575 gcc ctg ttc ctc ttc cac cgg cgg aag aag gag acc cgt tat gga gag    1776
Ala Leu Phe Leu Phe His Arg Arg Lys Lys Glu Thr Arg Tyr Gly Glu
                580                 585                 590 gtg ttt gaa cca acc gtg gag agg ggt gag ctg gtg gtc agg tac cgt    1824
Val Phe Glu Pro Thr Val Glu Arg Gly Glu Leu Val Val Arg Tyr Arg
                595                 600                 605 gtt cgc aag tcc tac agt cgg agg acc act gaa gcc acc ttg aac agc    1872
Val Arg Lys Ser Tyr Ser Arg Arg Thr Thr Glu Ala Thr Leu Asn Ser
610                 615                 620 ctc ggc atc agc gaa gag ctg aag gag aaa ctg cgg gat gtg atg gtg    1920
Leu Gly Ile Ser Glu Glu Leu Lys Glu Lys Leu Arg Asp Val Met Val
625                 630                 635                 640 gac cgg cat aag gtg gct ctg ggg aag acc ctg gga gag gga gag ttc    1968
Asp Arg His Lys Val Ala Leu Gly Lys Thr Leu Gly Glu Gly Glu Phe
                645                 650                 655 gga gct gtg atg gaa ggc cag ctc aac cag gac gac tcc gtc ctc aag    2016
Gly Ala Val Met Glu Gly Gln Leu Asn Gln Asp Asp Ser Val Leu Lys
                660                 665                 670 gtg gct gtg aag acc atg aag att gcc atc tgc aca agg tcg gag ctg    2064
Val Ala Val Lys Thr Met Lys Ile Ala Ile Cys Thr Arg Ser Glu Leu
                675                 680                 685 gag gat ttc ctg agt gaa gcc gtc tgc atg aag gaa ttc gac cac ccc    2112
Glu Asp Phe Leu Ser Glu Ala Val Cys Met Lys Glu Phe Asp His Pro
690                 695                 700 aac gtc atg agg ctc att ggc gtt tgt ttc cag ggt tct gaa cga gaa    2160
Asn Val Met Arg Leu Ile Gly Val Cys Phe Gln Gly Ser Glu Arg Glu
705                 710                 715                 720 ggc ttc ccg gcg ccc gtg gtc atc tta ccc ttc atg aaa cac gga gac    2208
Gly Phe Pro Ala Pro Val Val Ile Leu Pro Phe Met Lys His Gly Asp
                725                 730                 735 cta cac agt ttc ctt ctc tat tcc cgg ctc ggg gac cag cca gtg ttc    2256
Leu His Ser Phe Leu Leu Tyr Ser Arg Leu Gly Asp Gln Pro Val Phe
                740                 745                 750 ctg ccc acc cag atg ctg gtg aag ttc atg gca gat att gcc agt ggc    2304
Leu Pro Thr Gln Met Leu Val Lys Phe Met Ala Asp Ile Ala Ser Gly
                755                 760                 765 atg gag tat ctg agt acc aag aga ttc ata cac cgg gac ctg gct gct    2352
Met Glu Tyr Leu Ser Thr Lys Arg Phe Ile His Arg Asp Leu Ala Ala
770                 775                 780 agg aat tgc atg ctg aat gag aac atg tcg gtg tgt gtg gct gac ttt    2400
Arg Asn Cys Met Leu Asn Glu Asn Met Ser Val Cys Val Ala Asp Phe
785                 790                 795                 800 ggg ctc tcc aag aag atc tac aat ggg gac tac tac cgt cag gga cgc    2448
Gly Leu Ser Lys Lys Ile Tyr Asn Gly Asp Tyr Tyr Arg Gln Gly Arg
                805                 810                 815 atc gcc aag atg ccg gtc aag tgg att gcc atc gag agc ctg gcg gac    2496
Ile Ala Lys Met Pro Val Lys Trp Ile Ala Ile Glu Ser Leu Ala Asp
                820                 825                 830 cgt gtc tat acc agc aag agc gat gta tgg tcc ttt ggg gtg acg atg    2544
Arg Val Tyr Thr Ser Lys Ser Asp Val Trp Ser Phe Gly Val Thr Met
```

-continued

```
              835                 840                 845
tgg gag att gcc acg cga ggg caa acc cca tat cca gga gtg gag aac      2592
Trp Glu Ile Ala Thr Arg Gly Gln Thr Pro Tyr Pro Gly Val Glu Asn
    850                 855                 860 agt gag att tat gac tac ctg cgc cag gga aac cgc ctg aag cag ccc      2640
Ser Glu Ile Tyr Asp Tyr Leu Arg Gln Gly Asn Arg Leu Lys Gln Pro
865                 870                 875                 880 gtg gac tgt ctg gac gga ctg tac gcc ctg atg tcc cgg tgc tgg gag      2688
Val Asp Cys Leu Asp Gly Leu Tyr Ala Leu Met Ser Arg Cys Trp Glu
                885                 890                 895 cta aac ccc cgg gac cgg ccg agt ttt gca gag ctg cgg gaa gac ctg      2736
Leu Asn Pro Arg Asp Arg Pro Ser Phe Ala Glu Leu Arg Glu Asp Leu
    900                 905                 910 gag aat acg ctg aag gcc ctg ccc cct gct cag gag cca gac gaa atc      2784
Glu Asn Thr Leu Lys Ala Leu Pro Pro Ala Gln Glu Pro Asp Glu Ile
915                 920                 925 ctc tat gtc aac atg gat gag ggt gga ggt cat tct gaa cca ctt gga      2832
Leu Tyr Val Asn Met Asp Glu Gly Gly Gly His Ser Glu Pro Leu Gly
                930                 935                 940 gct gct gga gga gcg gac ccc cca gct cag cct gac cct aag gat tcc      2880
Ala Ala Gly Gly Ala Asp Pro Pro Ala Gln Pro Asp Pro Lys Asp Ser
945                 950                 955                 960 tgc agc tgc ctc acc gcc gct gaa gtc cat cct gcc ggc cgc tat gtc      2928
Cys Ser Cys Leu Thr Ala Ala Glu Val His Pro Ala Gly Arg Tyr Val
                965                 970                 975 ctc tgc cct tct aca gcc cct ggc ccc atc ctg cct gct gaa agg agc      2976
Leu Cys Pro Ser Thr Ala Pro Gly Pro Ile Leu Pro Ala Glu Arg Ser
                980                 985                 990 tcc cca gca ccc ccg ggg cag gag     gac ggc gcc tga gaccaccctc       3022
Ser Pro Ala Pro Pro Gly Gln Glu     Asp Gly Ala
                995                 1000 cacctgggac ttcctctcag acccaagct aggcactgcc actggggac ggccccctac      3082
tttcccactc cagaccctac ccccaaccat agccctctct tcctacctgt tccacttcca    3142
tcccagacag atcctctccc ttttccatac cttagtgtcc ccatgcgtaa aagaaaggga    3202
ttagactgaa atccctgagg gccctcccag gtttaacatt ccaagattct agattctaag    3262
gtttaaagag tctagattca cagggtctaa gtttcagagc tgaatctttg agtctaaaga    3322
cttTgaattc cagtctctaa ttctaaagtg ctaaggttct agacatggaa gttctaaggc    3382
ctacattcta aggctctgag atgctgtggc tctagatttt tctggttctg agattcttca    3442
taaagcccat gaaattttag gttacaaagc tctaagattc tatttctaga atctaaggct    3502
ctgtgatttt agatttttat ttttctaggg ttttaagtcc tgagggtgta agatactaga    3562
tcctacaatt ctaaaaatcc tacagttcta gacatggagg ttctaaggcc ttatgttcta    3622
aaatttgaag ttctgggcct cttagagtat aacttttctg gttttaagac tccagatcat    3682
aagccacaag atttgatctt ctcaagttct aagattctaa tgatggtcag tgacagagtc    3742
taaggcttta tgatccttga aacccttgtt atgagactgt ggatcctaaa gatctaaaat    3802
gctagcatct gcaattcaaa agttctaata gtctaaagat ggaggttcta aggtctaatg    3862
ttctaagatg tgatgttcta aggcttagtc taagaaccta gagtctctgt gtctaagatt    3922
ccagatcata tgcttcaaga ttctagatta ttaaactcta agattctaat gttgttctgt    3982
tctgtgttcc aaggcattct agatcctatt ggtccaagat tctggatcct cagcatctat    4042
ggtatagata ttcacggtt agtggtgaca aactggatgc caaagttcta atcatttta     4102
atttcggaca cctttaagtt ctatgctgca tcttctcttt ccaggatttt agttaaggt     4162
```

```
ctaggaattc atggttctaa gttttacgat tctgggttcc aagattcaca tgttataaga    4222
ttctaaaggt ctagaattcc aaagtaaaat tctgaggttc taaccttata gttttatcct    4282
gtgtgaccct tcccttctta gccacctctg cttcctcttc ctttcatgtg ggggcgtgcc    4342
ccctcaaacc tgtgcaatgc aataaagacg cctccttttcc ccagaggaca atatccctct    4402
tttgggggcc atattgcccc cctgagccag tcctttatgc ctcctgaaca gagtgtgaac    4462
cctggcacct ccagtggggc tcagatcaca taaaactttg taaccatg                  4510
```

<210> SEQ ID NO 12
<211> LENGTH: 1003
<212> TYPE: PRT
<213> ORGANISM: Bos taurus

<400> SEQUENCE: 12

```
Met Gly Gln Thr Asp Arg Arg Gly Gly Leu Gly Ala Gly Leu Asp
1               5                   10                  15

Leu Gly Ala Ser Gln Arg Gly Ala Glu Arg Arg Leu Pro Pro Ile Ser
            20                  25                  30

Phe Ser Ser Pro Pro Ser Thr Ser Pro Val Cys Glu Val Ser Arg Asp
        35                  40                  45

Pro Lys Gln Gly Gln Ala Ser Arg Ala Val Arg Ala Trp Glu Ala Ala
    50                  55                  60

Arg Cys Trp Ala Tyr Phe Pro Thr Gly Trp Arg Pro Asp Pro Ser Pro
65                  70                  75                  80

Leu Gly Arg Leu Pro Ser Ser Ser Arg Ser Leu His Pro Pro Pro
                85                  90                  95

Gln Leu Arg Ser Leu Asn Asn Tyr Val Gly Leu Arg Ala Trp Arg Gly
            100                 105                 110

Pro Gly Ser Arg Arg Gln Ala Gly Arg Asp Gly Thr Glu Glu Ser Arg
        115                 120                 125

Glu Ala Gly Val Pro Lys Leu Met Phe Phe His Leu Pro Ala Gly Pro
    130                 135                 140

Gln Thr Glu Val Ser Pro Phe Val Gly Ser Pro Gly Asn Ile Thr Gly
145                 150                 155                 160

Ala Arg Gly Leu Met Gly Thr Leu Arg Cys Glu Leu Gln Val Gln Gly
                165                 170                 175

Glu Pro Pro Glu Val Thr Trp Leu Arg Asp Gly Gln Val Leu Glu Leu
            180                 185                 190

Ala Asp Ser Thr Gln Thr Gln Val Pro Leu Gly Glu Asp Gly Gln Asp
        195                 200                 205

Asp Trp Lys Val Val Ser Gln Leu Arg Ile Ser Ser Leu Gln Leu Ser
    210                 215                 220

Asp Ala Gly Trp Tyr Gln Cys Thr Val Val Leu Gly Glu Lys Thr Phe
225                 230                 235                 240

Val Ser Gln Pro Gly Tyr Val Gly Leu Glu Gly Leu Pro Tyr Phe Leu
                245                 250                 255

Glu Glu Pro Glu Asp Arg Thr Val Val Ala Asn Thr Pro Phe Asn Leu
            260                 265                 270

Ser Cys Arg Ala Gln Gly Pro Pro Glu Pro Val Asp Leu Leu Trp Leu
        275                 280                 285

Gln Asp Ala Val Ser Leu Ala Ser Ala Met Asp His Ser Pro Gln His
    290                 295                 300

Thr Leu Arg Val Pro Gly Leu Asn Lys Thr Ala Ser Phe Ser Cys Glu
305                 310                 315                 320
```

-continued

```
Ala His Asn Ala Lys Gly Ile Thr Thr Ser Arg Thr Ala Thr Ile Thr
                325                 330                 335

Val Leu Pro Gln Arg Pro His Asp Leu His Leu Val Ser Thr Gln Pro
                340                 345                 350

Thr Glu Leu Glu Val Ala Trp Thr Pro Gly Leu Ser Gly Ile Tyr Pro
                355                 360                 365

Leu Thr His Cys Ile Leu Gln Ala Val Leu Ser Asp Asp Arg Val Gly
                370                 375                 380

Ala Trp Leu Gly Glu Pro Asp Pro Glu Glu Pro Leu Thr Leu Gln
385                 390                 395                 400

Ala Ser Val Pro Pro His Gln Leu Arg Leu Gly Ser Leu His Pro His
                405                 410                 415

Thr Pro Tyr His Leu Arg Val Ala Cys Val Ser Ser Gln Gly Pro Ser
                420                 425                 430

Pro Trp Thr His Trp Leu Pro Val Glu Thr Pro Glu Gly Glu Tyr Trp
                435                 440                 445

Ser Gly Leu Pro Cys Pro Pro Gly Asn Leu Pro Asp Pro Arg Asp
                450                 455                 460

Pro Thr His Val Ser Trp Ile Arg Pro Lys Ser Pro Ala Leu Gln Gly
465                 470                 475                 480

Gly Phe Leu Thr Thr Gly Pro Pro Gly Thr Ser Pro His Thr Pro Pro
                485                 490                 495

Pro Thr Ser Thr Pro Phe Met Ser Ile Ala Cys Pro Val Gln Pro Cys
                500                 505                 510

Pro Ser Pro Asn Glu Pro Thr Pro Ala Ser Leu Gln His His Pro Pro
                515                 520                 525

Gly Asp Pro Arg Asn Gln Asp Leu His His Asp Leu Ser Ala Tyr Pro
                530                 535                 540

Val Thr Val Ser Glu Pro Pro Ala Pro Ala Phe Ser Trp Pro Trp Trp
545                 550                 555                 560

Tyr Val Leu Leu Gly Ala Val Val Ala Ala Cys Val Leu Ile Leu
                565                 570                 575

Ala Leu Phe Leu Phe His Arg Arg Lys Lys Glu Thr Arg Tyr Gly Glu
                580                 585                 590

Val Phe Glu Pro Thr Val Glu Arg Gly Glu Leu Val Val Arg Tyr Arg
                595                 600                 605

Val Arg Lys Ser Tyr Ser Arg Arg Thr Thr Glu Ala Thr Leu Asn Ser
                610                 615                 620

Leu Gly Ile Ser Glu Glu Leu Lys Glu Lys Leu Arg Asp Val Met Val
625                 630                 635                 640

Asp Arg His Lys Val Ala Leu Gly Lys Thr Leu Gly Glu Gly Glu Phe
                645                 650                 655

Gly Ala Val Met Glu Gly Gln Leu Asn Gln Asp Asp Ser Val Leu Lys
                660                 665                 670

Val Ala Val Lys Thr Met Lys Ile Ala Ile Cys Thr Arg Ser Glu Leu
                675                 680                 685

Glu Asp Phe Leu Ser Glu Ala Val Cys Met Lys Glu Phe Asp His Pro
                690                 695                 700

Asn Val Met Arg Leu Ile Gly Val Cys Phe Gln Gly Ser Glu Arg Glu
705                 710                 715                 720

Gly Phe Pro Ala Pro Val Val Ile Leu Pro Phe Met Lys His Gly Asp
                725                 730                 735

Leu His Ser Phe Leu Leu Tyr Ser Arg Leu Gly Asp Gln Pro Val Phe
                740                 745                 750
```

```
Leu Pro Thr Gln Met Leu Val Lys Phe Met Ala Asp Ile Ala Ser Gly
            755                 760                 765

Met Glu Tyr Leu Ser Thr Lys Arg Phe Ile His Arg Asp Leu Ala Ala
        770                 775                 780

Arg Asn Cys Met Leu Asn Glu Asn Met Ser Val Cys Val Ala Asp Phe
785                 790                 795                 800

Gly Leu Ser Lys Lys Ile Tyr Asn Gly Asp Tyr Tyr Arg Gln Gly Arg
                805                 810                 815

Ile Ala Lys Met Pro Val Lys Trp Ile Ala Ile Glu Ser Leu Ala Asp
            820                 825                 830

Arg Val Tyr Thr Ser Lys Ser Asp Val Trp Ser Phe Gly Val Thr Met
        835                 840                 845

Trp Glu Ile Ala Thr Arg Gly Gln Thr Pro Tyr Pro Gly Val Glu Asn
    850                 855                 860

Ser Glu Ile Tyr Asp Tyr Leu Arg Gln Gly Asn Arg Leu Lys Gln Pro
865                 870                 875                 880

Val Asp Cys Leu Asp Gly Leu Tyr Ala Leu Met Ser Arg Cys Trp Glu
                885                 890                 895

Leu Asn Pro Arg Asp Arg Pro Ser Phe Ala Glu Leu Arg Glu Asp Leu
            900                 905                 910

Glu Asn Thr Leu Lys Ala Leu Pro Pro Ala Gln Glu Pro Asp Glu Ile
        915                 920                 925

Leu Tyr Val Asn Met Asp Glu Gly Gly Gly His Ser Glu Pro Leu Gly
    930                 935                 940

Ala Ala Gly Gly Ala Asp Pro Pro Ala Gln Pro Asp Pro Lys Asp Ser
945                 950                 955                 960

Cys Ser Cys Leu Thr Ala Ala Glu Val His Pro Ala Gly Arg Tyr Val
                965                 970                 975

Leu Cys Pro Ser Thr Ala Pro Gly Pro Ile Leu Pro Ala Glu Arg Ser
            980                 985                 990

Ser Pro Ala Pro Pro Gly Gln Glu  Asp Gly Ala
        995                 1000

<210> SEQ ID NO 13
<211> LENGTH: 2664
<212> TYPE: DNA
<213> ORGANISM: Canis familiaris
<220> FEATURE:
<221> NAME/KEY: CDS
<222> LOCATION: (1)..(2664)

<400> SEQUENCE: 13 atg ggc agg gtc ccg ctg gcc tgg tgc ttg gcg ctg tgc tgc tgg ggg      48
Met Gly Arg Val Pro Leu Ala Trp Cys Leu Ala Leu Cys Cys Trp Gly
1               5                   10                  15 tgc ctg gcc ccc ccg ggc aca cag gct gag gca gac ccc ttt gtg ggg      96
Cys Leu Ala Pro Pro Gly Thr Gln Ala Glu Ala Asp Pro Phe Val Gly
            20                  25                  30 agt cca agg aac atc acc ggt gcc cga gga ctc acc ggg gcc ctt cgg     144
Ser Pro Arg Asn Ile Thr Gly Ala Arg Gly Leu Thr Gly Ala Leu Arg
        35                  40                  45 tgt gag ctc cag gtt cag ggg gag ccc cct gag gtg acg tgg ctt cgg     192
Cys Glu Leu Gln Val Gln Gly Glu Pro Pro Glu Val Thr Trp Leu Arg
    50                  55                  60 gat gga cag gtg ctg gag ctg gcg gac agt acc cag acc cag gtg ccc     240
Asp Gly Gln Val Leu Glu Leu Ala Asp Ser Thr Gln Thr Gln Val Pro
65                  70                  75                  80
```

```
ctg ggt gaa gac ggg cag gat gac tgg aag gtg gtc agc caa ctc aga    288
Leu Gly Glu Asp Gly Gln Asp Asp Trp Lys Val Val Ser Gln Leu Arg
                85                  90                  95 atc tca tcc ctg cag ctc tca gac gcc ggg tgg tac caa tgt gcc gtg    336
Ile Ser Ser Leu Gln Leu Ser Asp Ala Gly Trp Tyr Gln Cys Ala Val
            100                 105                 110 gtc ctg gga gga aag acc ttc gtg tcg cag cct ggc tac gtt ggg ctg    384
Val Leu Gly Gly Lys Thr Phe Val Ser Gln Pro Gly Tyr Val Gly Leu
        115                 120                 125 gag ggc ctg cct tac ttc ctg gag gag ccc gag gac aga acc gtg gcc    432
Glu Gly Leu Pro Tyr Phe Leu Glu Glu Pro Glu Asp Arg Thr Val Ala
    130                 135                 140 gcc aat acc ccc ttt aac ctg agc tgc cgg gct gag gga ccc cca gag    480
Ala Asn Thr Pro Phe Asn Leu Ser Cys Arg Ala Glu Gly Pro Pro Glu
145                 150                 155                 160 cct gtg gat cta ctc tgg ctc cag gat gcc gtc ccc cta cct cta gcc    528
Pro Val Asp Leu Leu Trp Leu Gln Asp Ala Val Pro Leu Pro Leu Ala
                165                 170                 175 gcg acc cac agt gcc cag cac acg ctg cgc att cca ggc ttg aac aag    576
Ala Thr His Ser Ala Gln His Thr Leu Arg Ile Pro Gly Leu Asn Lys
            180                 185                 190 aca tct tct ttc tcc tgt gaa gcc cat aat gcc aag ggg gtc acc aca    624
Thr Ser Ser Phe Ser Cys Glu Ala His Asn Ala Lys Gly Val Thr Thr
        195                 200                 205 tcc cgc aca gcc acc atc aca gtg ctc ccc cag cgg ccc cgc aac ctc    672
Ser Arg Thr Ala Thr Ile Thr Val Leu Pro Gln Arg Pro Arg Asn Leu
    210                 215                 220 cac ctg gtt tcc cgc cag ccc aca gag ctg gag gtg gct tgg act cca    720
His Leu Val Ser Arg Gln Pro Thr Glu Leu Glu Val Ala Trp Thr Pro
225                 230                 235                 240 ggc ctg agt ggc atc tat ccc ctc acg cac tgc acc ctg cag cct caa    768
Gly Leu Ser Gly Ile Tyr Pro Leu Thr His Cys Thr Leu Gln Pro Gln
                245                 250                 255 gtc cca cca gat gtc ctg ggt tca aat cct gac tcc ccc aac ccc ccg    816
Val Pro Pro Asp Val Leu Gly Ser Asn Pro Asp Ser Pro Asn Pro Pro
            260                 265                 270 gag gag cct ctc acc ttg caa gcg ttt gtc ccc cct cac caa ctt cgg    864
Glu Glu Pro Leu Thr Leu Gln Ala Phe Val Pro Pro His Gln Leu Arg
        275                 280                 285 gtg ggc agc ctc cat cct cac act cct tac cac atc cgg gtg gcc tgt    912
Val Gly Ser Leu His Pro His Thr Pro Tyr His Ile Arg Val Ala Cys
    290                 295                 300 acc agt agc cag ggg ccc tca ccc tgg acc cac tgg ctt cct gtg gag    960
Thr Ser Ser Gln Gly Pro Ser Pro Trp Thr His Trp Leu Pro Val Glu
305                 310                 315                 320 aca cca gag gga gtg ccc ctg ggt ccc ccc gag aac gtt agc gcc ttg   1008
Thr Pro Glu Gly Val Pro Leu Gly Pro Pro Glu Asn Val Ser Ala Leu
                325                 330                 335 cgg aat ggg agc caa gcc ctc gtg cgt tgg cag gag cca agg gcg ccc   1056
Arg Asn Gly Ser Gln Ala Leu Val Arg Trp Gln Glu Pro Arg Ala Pro
            340                 345                 350 ctg cag ggc acc ctg tta ggg tac cgg ctg gcc tac cga ggc cag gac   1104
Leu Gln Gly Thr Leu Leu Gly Tyr Arg Leu Ala Tyr Arg Gly Gln Asp
        355                 360                 365 acc ccc gag gtg ctc atg gac ata ggc cta aag aga gag gtg acc ctg   1152
Thr Pro Glu Val Leu Met Asp Ile Gly Leu Lys Arg Glu Val Thr Leu
    370                 375                 380 gag ctg caa ggg gat ggg acg gtg ccc aac ctg aca gtg tgt gtg gca   1200
Glu Leu Gln Gly Asp Gly Thr Val Pro Asn Leu Thr Val Cys Val Ala
385                 390                 395                 400
```

```
gcc tac act gct gct ggg gat gga ccc tgg agc ctc cct gtg ccc ctg    1248
Ala Tyr Thr Ala Ala Gly Asp Gly Pro Trp Ser Leu Pro Val Pro Leu
        405                 410                 415 gag ccc tgg cgc cca ggg caa gga caa cca atc cac cag ctg gtg agt    1296
Glu Pro Trp Arg Pro Gly Gln Gly Gln Pro Ile His Gln Leu Val Ser
    420                 425                 430 gag ccc cca gcc cct gcc ttc tca tgg ccc tgg tgg tat gta ttg ctg    1344
Glu Pro Pro Ala Pro Ala Phe Ser Trp Pro Trp Trp Tyr Val Leu Leu
            435                 440                 445 gga gca gtc gtg gct gcc ggt tgt gtc ctc atc ttg gcc ctg ttc ctt    1392
Gly Ala Val Val Ala Ala Gly Cys Val Leu Ile Leu Ala Leu Phe Leu
450                 455                 460 gtc cac cgg cgg aag aag gag acc cgc tat gga gag gtg ttt gaa cca    1440
Val His Arg Arg Lys Lys Glu Thr Arg Tyr Gly Glu Val Phe Glu Pro
465                 470                 475                 480 aca gtg gag agg ggt gag ctg gtg gtt agg tac cgt gtt cgc aag tcc    1488
Thr Val Glu Arg Gly Glu Leu Val Val Arg Tyr Arg Val Arg Lys Ser
                485                 490                 495 tac agt cgc cgg acc act gaa gcc acc ttg aac agc ctg ggc atc agt    1536
Tyr Ser Arg Arg Thr Thr Glu Ala Thr Leu Asn Ser Leu Gly Ile Ser
            500                 505                 510 gaa gag ctg aag gag aag ctt cgg gat gtg atg gtg gac cgg cat aag    1584
Glu Glu Leu Lys Glu Lys Leu Arg Asp Val Met Val Asp Arg His Lys
        515                 520                 525 gtg gcg ctg ggg aag acc ctg gga gaa gga gaa ttt gga gca gtg atg    1632
Val Ala Leu Gly Lys Thr Leu Gly Glu Gly Glu Phe Gly Ala Val Met
    530                 535                 540 gag ggc cag ctc aac cag gat gac tct atc ctc aag gtg gct gtg aag    1680
Glu Gly Gln Leu Asn Gln Asp Asp Ser Ile Leu Lys Val Ala Val Lys
545                 550                 555                 560 aca atg aag att gct atc tgc aca agg tcg gag ctg gag gat ttc ctg    1728
Thr Met Lys Ile Ala Ile Cys Thr Arg Ser Glu Leu Glu Asp Phe Leu
                565                 570                 575 agt gaa gct gtc tgc atg aag gaa ttt gac cac ccc aac gtg atg agg    1776
Ser Glu Ala Val Cys Met Lys Glu Phe Asp His Pro Asn Val Met Arg
            580                 585                 590 ctc att ggc gtc tgt ttc cag ggt tcc gaa cga gag ggc ttc ccg gca    1824
Leu Ile Gly Val Cys Phe Gln Gly Ser Glu Arg Glu Gly Phe Pro Ala
        595                 600                 605 ccg gtg gtc atc tta cct ttc atg aag cat gga gac ctg cac agt ttc    1872
Pro Val Val Ile Leu Pro Phe Met Lys His Gly Asp Leu His Ser Phe
    610                 615                 620 ctt ctc tat tcc cgg ctt ggg gac cag cca gtg ttc ctg ccc act cag    1920
Leu Leu Tyr Ser Arg Leu Gly Asp Gln Pro Val Phe Leu Pro Thr Gln
625                 630                 635                 640 atg ctg gtg aag ttc atg gca gac atc gcc agt ggc atg gag tat ctg    1968
Met Leu Val Lys Phe Met Ala Asp Ile Ala Ser Gly Met Glu Tyr Leu
                645                 650                 655 agt acc aag aga ttc ata cac cga gac ctg gcc gcc agg aac tgc atg    2016
Ser Thr Lys Arg Phe Ile His Arg Asp Leu Ala Ala Arg Asn Cys Met
            660                 665                 670 ctg aat gag aac atg tcc gtg tgt gtg gcg gat ttt ggg ctt tcc aag    2064
Leu Asn Glu Asn Met Ser Val Cys Val Ala Asp Phe Gly Leu Ser Lys
        675                 680                 685 aag atc tac aat ggg gac tac tac cgc cag gga cgc atc gcc aag atg    2112
Lys Ile Tyr Asn Gly Asp Tyr Tyr Arg Gln Gly Arg Ile Ala Lys Met
    690                 695                 700 cca gtc aag tgg att gcc att gag agc ctg gct gac cgt gtc tac acc    2160
Pro Val Lys Trp Ile Ala Ile Glu Ser Leu Ala Asp Arg Val Tyr Thr
705                 710                 715                 720
```

```
agc aag agt gat gtg tgg tcc ttt ggg gtg acg atg tgg gag att gct    2208
Ser Lys Ser Asp Val Trp Ser Phe Gly Val Thr Met Trp Glu Ile Ala
            725                 730                 735 aca cgg ggc caa acc cca tat cca gga gtg gaa aac agc gag att tac    2256
Thr Arg Gly Gln Thr Pro Tyr Pro Gly Val Glu Asn Ser Glu Ile Tyr
        740                 745                 750 gac tac ctg tgc cag gga aat cga cta aag cag cct gtg ggc tgt ctg    2304
Asp Tyr Leu Cys Gln Gly Asn Arg Leu Lys Gln Pro Val Gly Cys Leu
    755                 760                 765 gat gga cta tat gcc ctg atg tcc cgg tgc tgg gag cta aac ccc cgg    2352
Asp Gly Leu Tyr Ala Leu Met Ser Arg Cys Trp Glu Leu Asn Pro Arg
770                 775                 780 gac cgg ccg agt ttc tca gag ctt cgg gaa gat ctg gag aac aca ctg    2400
Asp Arg Pro Ser Phe Ser Glu Leu Arg Glu Asp Leu Glu Asn Thr Leu
785                 790                 795                 800 aaa gcc ctg ccc cct gcc cag gag ccc gag gaa atc ctc tat gtc aac    2448
Lys Ala Leu Pro Pro Ala Gln Glu Pro Glu Glu Ile Leu Tyr Val Asn
            805                 810                 815 atg gat gag ggt ggg agt cat tct gaa cca ctt gga gct gct gga gga    2496
Met Asp Glu Gly Gly Ser His Ser Glu Pro Leu Gly Ala Ala Gly Gly
        820                 825                 830 gct gac ccc cca act cag cct gac ccc aag gat tcc tgc agt tgc ctc    2544
Ala Asp Pro Pro Thr Gln Pro Asp Pro Lys Asp Ser Cys Ser Cys Leu
    835                 840                 845 acc gcg gct gag gtc cat cct gct gga cgc tat gtc ctc tgc cct tct    2592
Thr Ala Ala Glu Val His Pro Ala Gly Arg Tyr Val Leu Cys Pro Ser
850                 855                 860 aca gcc cct ggc ccc gcc ctg cct act gac agg agc tcc cca gct cct    2640
Thr Ala Pro Gly Pro Ala Leu Pro Thr Asp Arg Ser Ser Pro Ala Pro
865                 870                 875                 880 cca ggg cag gag gat gga gcc tga                                    2664
Pro Gly Gln Glu Asp Gly Ala
            885
```

<210> SEQ ID NO 14
<211> LENGTH: 887
<212> TYPE: PRT
<213> ORGANISM: Canis familiaris

<400> SEQUENCE: 14

```
Met Gly Arg Val Pro Leu Ala Trp Cys Leu Ala Leu Cys Cys Trp Gly
1               5                   10                  15

Cys Leu Ala Pro Pro Gly Thr Gln Ala Glu Ala Asp Pro Phe Val Gly
            20                  25                  30

Ser Pro Arg Asn Ile Thr Gly Ala Arg Gly Leu Thr Gly Ala Leu Arg
        35                  40                  45

Cys Glu Leu Gln Val Gln Gly Glu Pro Pro Glu Val Thr Trp Leu Arg
    50                  55                  60

Asp Gly Gln Val Leu Glu Leu Ala Asp Ser Thr Gln Thr Gln Val Pro
65                  70                  75                  80

Leu Gly Glu Asp Gly Gln Asp Asp Trp Lys Val Val Ser Gln Leu Arg
                85                  90                  95

Ile Ser Ser Leu Gln Leu Ser Asp Ala Gly Trp Tyr Gln Cys Ala Val
            100                 105                 110

Val Leu Gly Gly Lys Thr Phe Val Ser Gln Pro Gly Tyr Val Gly Leu
        115                 120                 125

Glu Gly Leu Pro Tyr Phe Leu Glu Glu Pro Gly Asp Arg Thr Val Ala
    130                 135                 140

Ala Asn Thr Pro Phe Asn Leu Ser Cys Arg Ala Glu Gly Pro Pro Glu
```

```
                145                 150                 155                 160
        Pro Val Asp Leu Leu Trp Leu Gln Asp Ala Val Pro Leu Pro Leu Ala
                        165                 170                 175

Ala Thr His Ser Ala Gln His Thr Leu Arg Ile Pro Gly Leu Asn Lys
                        180                 185                 190

Thr Ser Ser Phe Ser Cys Glu Ala His Asn Ala Lys Gly Val Thr Thr
                        195                 200                 205

Ser Arg Thr Ala Thr Ile Thr Val Leu Pro Gln Arg Pro Arg Asn Leu
                210                 215                 220

His Leu Val Ser Arg Gln Pro Thr Glu Leu Glu Val Ala Trp Thr Pro
        225                 230                 235                 240

Gly Leu Ser Gly Ile Tyr Pro Leu Thr His Cys Thr Leu Gln Pro Gln
                        245                 250                 255

Val Pro Pro Asp Val Leu Gly Ser Asn Pro Asp Ser Pro Asn Pro Pro
                        260                 265                 270

Glu Glu Pro Leu Thr Leu Gln Ala Phe Val Pro Pro His Gln Leu Arg
                        275                 280                 285

Val Gly Ser Leu His Pro His Thr Pro Tyr His Ile Arg Val Ala Cys
                        290                 295                 300

Thr Ser Ser Gln Gly Pro Ser Pro Trp Thr His Trp Leu Pro Val Glu
        305                 310                 315                 320

Thr Pro Glu Gly Val Pro Leu Gly Pro Pro Glu Asn Val Ser Ala Leu
                        325                 330                 335

Arg Asn Gly Ser Gln Ala Leu Val Arg Trp Gln Glu Pro Arg Ala Pro
                        340                 345                 350

Leu Gln Gly Thr Leu Leu Gly Tyr Arg Leu Ala Tyr Arg Gly Gln Asp
                        355                 360                 365

Thr Pro Glu Val Leu Met Asp Ile Gly Leu Lys Arg Glu Val Thr Leu
                        370                 375                 380

Glu Leu Gln Gly Asp Gly Thr Val Pro Asn Leu Thr Val Cys Val Ala
        385                 390                 395                 400

Ala Tyr Thr Ala Ala Gly Asp Gly Pro Trp Ser Leu Pro Val Pro Leu
                        405                 410                 415

Glu Pro Trp Arg Pro Gly Gln Gly Gln Pro Ile His Gln Leu Val Ser
                        420                 425                 430

Glu Pro Pro Ala Pro Ala Phe Ser Trp Pro Trp Trp Tyr Val Leu Leu
                        435                 440                 445

Gly Ala Val Val Ala Ala Gly Cys Val Leu Ile Leu Ala Leu Phe Leu
                        450                 455                 460

Val His Arg Arg Lys Lys Glu Thr Arg Tyr Gly Glu Val Phe Glu Pro
        465                 470                 475                 480

Thr Val Glu Arg Gly Glu Leu Val Val Arg Tyr Arg Val Arg Lys Ser
                        485                 490                 495

Tyr Ser Arg Arg Thr Thr Glu Ala Thr Leu Asn Ser Leu Gly Ile Ser
                        500                 505                 510

Glu Glu Leu Lys Glu Lys Leu Arg Asp Val Met Val Asp Arg His Lys
                        515                 520                 525

Val Ala Leu Gly Lys Thr Leu Gly Glu Gly Glu Phe Gly Ala Val Met
                        530                 535                 540

Glu Gly Gln Leu Asn Gln Asp Asp Ser Ile Leu Lys Val Ala Val Lys
        545                 550                 555                 560

Thr Met Lys Ile Ala Ile Cys Thr Arg Ser Glu Leu Glu Asp Phe Leu
                        565                 570                 575
```

```
Ser Glu Ala Val Cys Met Lys Glu Phe Asp His Pro Asn Val Met Arg
                580                 585                 590

Leu Ile Gly Val Cys Phe Gln Gly Ser Glu Arg Glu Gly Phe Pro Ala
            595                 600                 605

Pro Val Val Ile Leu Pro Phe Met Lys His Gly Asp Leu His Ser Phe
        610                 615                 620

Leu Leu Tyr Ser Arg Leu Gly Asp Gln Pro Val Phe Leu Pro Thr Gln
625                 630                 635                 640

Met Leu Val Lys Phe Met Ala Asp Ile Ala Ser Gly Met Glu Tyr Leu
                645                 650                 655

Ser Thr Lys Arg Phe Ile His Arg Asp Leu Ala Ala Arg Asn Cys Met
            660                 665                 670

Leu Asn Glu Asn Met Ser Val Cys Val Ala Asp Phe Gly Leu Ser Lys
        675                 680                 685

Lys Ile Tyr Asn Gly Asp Tyr Tyr Arg Gln Gly Arg Ile Ala Lys Met
690                 695                 700

Pro Val Lys Trp Ile Ala Ile Glu Ser Leu Ala Asp Arg Val Tyr Thr
705                 710                 715                 720

Ser Lys Ser Asp Val Trp Ser Phe Gly Val Thr Met Trp Glu Ile Ala
                725                 730                 735

Thr Arg Gly Gln Thr Pro Tyr Pro Gly Val Glu Asn Ser Glu Ile Tyr
            740                 745                 750

Asp Tyr Leu Cys Gln Gly Asn Arg Leu Lys Gln Pro Val Gly Cys Leu
        755                 760                 765

Asp Gly Leu Tyr Ala Leu Met Ser Arg Cys Trp Glu Leu Asn Pro Arg
770                 775                 780

Asp Arg Pro Ser Phe Ser Glu Leu Arg Glu Asp Leu Glu Asn Thr Leu
785                 790                 795                 800

Lys Ala Leu Pro Pro Ala Gln Glu Pro Glu Glu Ile Leu Tyr Val Asn
                805                 810                 815

Met Asp Glu Gly Gly Ser His Ser Glu Pro Leu Gly Ala Ala Gly Gly
            820                 825                 830

Ala Asp Pro Pro Thr Gln Pro Asp Pro Lys Asp Ser Cys Ser Cys Leu
        835                 840                 845

Thr Ala Ala Glu Val His Pro Ala Gly Arg Tyr Val Leu Cys Pro Ser
850                 855                 860

Thr Ala Pro Gly Pro Ala Leu Pro Thr Asp Arg Ser Ser Pro Ala Pro
865                 870                 875                 880

Pro Gly Gln Glu Asp Gly Ala
                885

<210> SEQ ID NO 15
<211> LENGTH: 2682
<212> TYPE: DNA
<213> ORGANISM: Danio rerio
<220> FEATURE:
<221> NAME/KEY: CDS
<222> LOCATION: (1)..(2682)

<400> SEQUENCE: 15 atg cag ctt gga aag ccc cat gca cac cca gtc tac cat gct tgt aac      48
Met Gln Leu Gly Lys Pro His Ala His Pro Val Tyr His Ala Cys Asn
1               5                   10                  15 cct aaa ttc aaa aag aaa tct aaa aaa tta ttg aca aaa tgg atc cca      96
Pro Lys Phe Lys Lys Lys Ser Lys Lys Leu Leu Thr Lys Trp Ile Pro
            20                  25                  30 aaa caa gat gcc cgt gag ctt ctg ctg gac ctg agt ttt gcc caa gtg     144
```

-continued

| | | | | | | | | | | | | | | |
|---|---|---|---|---|---|---|---|---|---|---|---|---|---|---|
| Lys | Gln | Asp | Ala | Arg | Glu | Leu | Leu | Leu | Asp | Leu | Ser | Phe | Ala | Gln | Val |
| | | 35 | | | | 40 | | | | 45 | | | | |

| gac | cag | cag | cct | ctt | tac | atc | ttt | gtt | att | aaa | tct | aac | cag | tct | cag | 192 |
|---|---|---|---|---|---|---|---|---|---|---|---|---|---|---|---|---|
| Asp | Gln | Gln | Pro | Leu | Tyr | Ile | Phe | Val | Ile | Lys | Ser | Asn | Gln | Ser | Gln | |
| | 50 | | | | 55 | | | | 60 | | | | | | | |

| aag | cca | tat | gga | cca | caa | aaa | cca | gtt | ctt | gca | atc | aca | gtc | cag | cat | 240 |
|---|---|---|---|---|---|---|---|---|---|---|---|---|---|---|---|---|
| Lys | Pro | Tyr | Gly | Pro | Gln | Lys | Pro | Val | Leu | Ala | Ile | Thr | Val | Gln | His | |
| 65 | | | | 70 | | | | 75 | | | | 80 | | | | |

| cca | ttc | ctt | gca | aac | ggc | tat | cct | cgg | gat | gag | gac | ctg | agt | cat | gcc | 288 |
|---|---|---|---|---|---|---|---|---|---|---|---|---|---|---|---|---|
| Pro | Phe | Leu | Ala | Asn | Gly | Tyr | Pro | Arg | Asp | Glu | Asp | Leu | Ser | His | Ala | |
| | | | | 85 | | | | | 90 | | | | | 95 | | |

| aag | gct | cta | aat | ttg | gga | aac | atc | tct | gag | aac | ggc | ttt | tac | ctg | gcg | 336 |
|---|---|---|---|---|---|---|---|---|---|---|---|---|---|---|---|---|
| Lys | Ala | Leu | Asn | Leu | Gly | Asn | Ile | Ser | Glu | Asn | Gly | Phe | Tyr | Leu | Ala | |
| | | | | 100 | | | | | 105 | | | | | 110 | | |

| ttt | tta | tac | agc | gga | aac | tgc | atg | ttc | att | gct | tca | gtc | cag | gtg | ttc | 384 |
|---|---|---|---|---|---|---|---|---|---|---|---|---|---|---|---|---|
| Phe | Leu | Tyr | Ser | Gly | Asn | Cys | Met | Phe | Ile | Ala | Ser | Val | Gln | Val | Phe | |
| | | | | 115 | | | | | 120 | | | | | 125 | | |

| ttc | ctc | aaa | tgt | cca | gct | ttt | gca | tgg | aag | cag | atg | aag | ttt | gag | gaa | 432 |
|---|---|---|---|---|---|---|---|---|---|---|---|---|---|---|---|---|
| Phe | Leu | Lys | Cys | Pro | Ala | Phe | Ala | Trp | Lys | Gln | Met | Lys | Phe | Glu | Glu | |
| | 130 | | | | | 135 | | | | | 140 | | | | | |

| act | gca | gca | gga | ggg | tcg | agg | aga | gga | gtg | tgt | gtg | gat | gga | gca | gtg | 480 |
|---|---|---|---|---|---|---|---|---|---|---|---|---|---|---|---|---|
| Thr | Ala | Ala | Gly | Gly | Ser | Arg | Arg | Gly | Val | Cys | Val | Asp | Gly | Ala | Val | |
| 145 | | | | | 150 | | | | | 155 | | | | | 160 | |

| gag | att | tcg | acc | ccg | ctg | act | gag | tgt | cag | tct | aat | ggg | aca | tgg | gct | 528 |
|---|---|---|---|---|---|---|---|---|---|---|---|---|---|---|---|---|
| Glu | Ile | Ser | Thr | Pro | Leu | Thr | Glu | Cys | Gln | Ser | Asn | Gly | Thr | Trp | Ala | |
| | | | | 165 | | | | | 170 | | | | | 175 | | |

| tca | ccg | caa | ggc | tca | ggt | gtc | ggc | agg | gca | gaa | tac | cag | agc | agt | gga | 576 |
|---|---|---|---|---|---|---|---|---|---|---|---|---|---|---|---|---|
| Ser | Pro | Gln | Gly | Ser | Gly | Val | Gly | Arg | Ala | Glu | Tyr | Gln | Ser | Ser | Gly | |
| | | | | 180 | | | | | 185 | | | | | 190 | | |

| gac | aca | ggc | aaa | ggt | gag | gaa | gtg | ttt | tat | gtg | ttt | aac | agt | gcc | ctt | 624 |
|---|---|---|---|---|---|---|---|---|---|---|---|---|---|---|---|---|
| Asp | Thr | Gly | Lys | Gly | Glu | Glu | Val | Phe | Tyr | Val | Phe | Asn | Ser | Ala | Leu | |
| | | 195 | | | | | 200 | | | | | 205 | | | | |

| aga | ggg | cca | cct | ctg | atg | tac | att | att | gat | tac | att | gcg | caa | atg | tcc | 672 |
|---|---|---|---|---|---|---|---|---|---|---|---|---|---|---|---|---|
| Arg | Gly | Pro | Pro | Leu | Met | Tyr | Ile | Ile | Asp | Tyr | Ile | Ala | Gln | Met | Ser | |
| | 210 | | | | | 215 | | | | | 220 | | | | | |

| act | att | ggt | gga | aca | gct | gaa | tgg | aat | gct | cta | aac | cag | ggg | gtt | gat | 720 |
|---|---|---|---|---|---|---|---|---|---|---|---|---|---|---|---|---|
| Thr | Ile | Gly | Gly | Thr | Ala | Glu | Trp | Asn | Ala | Leu | Asn | Gln | Gly | Val | Asp | |
| 225 | | | | | 230 | | | | | 235 | | | | | 240 | |

| gag | att | ctt | ctt | acc | tac | aac | tgg | tgg | ccc | gag | tgc | aat | tcc | aaa | ccc | 768 |
|---|---|---|---|---|---|---|---|---|---|---|---|---|---|---|---|---|
| Glu | Ile | Leu | Leu | Thr | Tyr | Asn | Trp | Trp | Pro | Glu | Cys | Asn | Ser | Lys | Pro | |
| | | | | 245 | | | | | 250 | | | | | 255 | | |

| tcc | aaa | gca | cat | gag | aat | ccc | atg | cgc | ctg | acc | aag | ccg | ttc | aat | gcc | 816 |
|---|---|---|---|---|---|---|---|---|---|---|---|---|---|---|---|---|
| Ser | Lys | Ala | His | Glu | Asn | Pro | Met | Arg | Leu | Thr | Lys | Pro | Phe | Asn | Ala | |
| | | | 260 | | | | | 265 | | | | | 270 | | | |

| cac | aat | ctt | ggt | agt | gat | tct | gga | tct | gat | ctc | aaa | acc | aaa | ccc | ggc | 864 |
|---|---|---|---|---|---|---|---|---|---|---|---|---|---|---|---|---|
| His | Asn | Leu | Gly | Ser | Asp | Ser | Gly | Ser | Asp | Leu | Lys | Thr | Lys | Pro | Gly | |
| | | 275 | | | | | 280 | | | | | 285 | | | | |

| tta | gcc | gaa | aac | act | acc | aca | gtg | aaa | ctg | ttg | atc | aac | aaa | gac | ccc | 912 |
|---|---|---|---|---|---|---|---|---|---|---|---|---|---|---|---|---|
| Leu | Ala | Glu | Asn | Thr | Thr | Thr | Val | Lys | Leu | Leu | Ile | Asn | Lys | Asp | Pro | |
| | 290 | | | | | 295 | | | | | 300 | | | | | |

| aca | gag | cta | caa | gac | agt | gaa | gga | gaa | cgg | aaa | gtc | cac | ata | ttg | tcc | 960 |
|---|---|---|---|---|---|---|---|---|---|---|---|---|---|---|---|---|
| Thr | Glu | Leu | Gln | Asp | Ser | Glu | Gly | Glu | Arg | Lys | Val | His | Ile | Leu | Ser | |
| 305 | | | | | 310 | | | | | 315 | | | | | 320 | |

| agt | tca | ata | ata | gca | cga | gcc | att | aag | aag | tgg | atg | cgt | cca | tat | gga | 1008 |
|---|---|---|---|---|---|---|---|---|---|---|---|---|---|---|---|---|
| Ser | Ser | Ile | Ile | Ala | Arg | Ala | Ile | Lys | Lys | Trp | Met | Arg | Pro | Tyr | Gly | |
| | | | | 325 | | | | | 330 | | | | | 335 | | |

| cag | tat | ttc | tgc | gaa | aca | gta | gag | ctc | cta | cag | gac | cgg | gtc | ttc | atg | 1056 |
|---|---|---|---|---|---|---|---|---|---|---|---|---|---|---|---|---|
| Gln | Tyr | Phe | Cys | Glu | Thr | Val | Glu | Leu | Leu | Gln | Asp | Arg | Val | Phe | Met | |
| | | | 340 | | | | | 345 | | | | | 350 | | | |

| gct | ttc | tgt | atc | gcc | atg | ttt | ctg | ttt | agc | tta | gga | gca | ttt | cca | cct | 1104 |

```
            Ala Phe Cys Ile Ala Met Phe Leu Phe Ser Leu Gly Ala Phe Pro Pro
                355                 360                 365 gtg ctc ttc atg gag gac gtg gcc cag agc gaa ggg ctt att gat ggg             1152
Val Leu Phe Met Glu Asp Val Ala Gln Ser Glu Gly Leu Ile Asp Gly
370                 375                 380 att gcg ctg ata cca ctg gtc tcc att gtt gcg atg act aca ggc atc             1200
Ile Ala Leu Ile Pro Leu Val Ser Ile Val Ala Met Thr Thr Gly Ile
385                 390                 395                 400 ggt aag ctg att ctg ggt gtg ctg gcc gac atg cga tgg gtc aac agt             1248
Gly Lys Leu Ile Leu Gly Val Leu Ala Asp Met Arg Trp Val Asn Ser
                405                 410                 415 ctg tat ctg tac gcc ctg aca ctc att ggc tct gga acg gct ctg ctt             1296
Leu Tyr Leu Tyr Ala Leu Thr Leu Ile Gly Ser Gly Thr Ala Leu Leu
                420                 425                 430 ctc atc cct gtg tcc aag agc tat ttg ggt cta cag att ctt tca gcc             1344
Leu Ile Pro Val Ser Lys Ser Tyr Leu Gly Leu Gln Ile Leu Ser Ala
            435                 440                 445 gct gtt ggg ttt ttc tca ggg aac tgg tct ctt aca tca tac atc act             1392
Ala Val Gly Phe Phe Ser Gly Asn Trp Ser Leu Thr Ser Tyr Ile Thr
            450                 455                 460 acc aag att gtg ggc att gaa cgg ctt ggt cag gcg cat ggg att ctc             1440
Thr Lys Ile Val Gly Ile Glu Arg Leu Gly Gln Ala His Gly Ile Leu
465                 470                 475                 480 atg tgc ttt gga ggg ttt gga att gca ctc ggg cca cca gtt gta gtg             1488
Met Cys Phe Gly Gly Phe Gly Ile Ala Leu Gly Pro Pro Val Val Val
                485                 490                 495 tca gac tca gat cag atg ttg gat ggg ata aag gat cat ctg ctg tgt             1536
Ser Asp Ser Asp Gln Met Leu Asp Gly Ile Lys Asp His Leu Leu Cys
                500                 505                 510 ctt aga gat gtg ctg gtg gaa cgg aca aag tta caa tta agc caa aaa             1584
Leu Arg Asp Val Leu Val Glu Arg Thr Lys Leu Gln Leu Ser Gln Lys
                515                 520                 525 ctt ggg aaa ggg gaa ttt gga gct gtt tat gag ggc ata ttt tcc cct             1632
Leu Gly Lys Gly Glu Phe Gly Ala Val Tyr Glu Gly Ile Phe Ser Pro
530                 535                 540 aaa ata gga caa gac atc aga gtt gcg gtc aaa aca tct aaa gac gtg             1680
Lys Ile Gly Gln Asp Ile Arg Val Ala Val Lys Thr Ser Lys Asp Val
545                 550                 555                 560 atc cac agt gaa gaa gat ctg gag tct ttc ctg aag gag gcg gaa atg             1728
Ile His Ser Glu Glu Asp Leu Glu Ser Phe Leu Lys Glu Ala Glu Met
                565                 570                 575 atg aag cat ttc gat cat gtg aat gta gtt aaa ttg ctc ggt ttt agc             1776
Met Lys His Phe Asp His Val Asn Val Val Lys Leu Leu Gly Phe Ser
                580                 585                 590 ccg aac ccg acc gct ccc gct tat gct cag cat tta ttg tcc cgc tgc             1824
Pro Asn Pro Thr Ala Pro Ala Tyr Ala Gln His Leu Leu Ser Arg Cys
            595                 600                 605 ccg act cgc tct gtt ttc tac ccg ccg tgc ctg ttc ctg gta atg ggg             1872
Pro Thr Arg Ser Val Phe Tyr Pro Pro Cys Leu Phe Leu Val Met Gly
610                 615                 620 gtt gca cta gag tgg gat ccg gaa tct tct atg gtt gta cca ctg gtt             1920
Val Ala Leu Glu Trp Asp Pro Glu Ser Ser Met Val Val Pro Leu Val
625                 630                 635                 640 att ctc cca tac atg aag cac aga gac tta cac agt ttc ctc aga gcg             1968
Ile Leu Pro Tyr Met Lys His Arg Asp Leu His Ser Phe Leu Arg Ala
                645                 650                 655 aca aga tac gat gat gtt ccc atg ttt gtg cct cat cag agt ctt ctg             2016
Thr Arg Tyr Asp Asp Val Pro Met Phe Val Pro His Gln Ser Leu Leu
                660                 665                 670 cgc ttt atg atg gac att gct gcg gga atg gag tat ctg agc ctt cag             2064
```

```
Arg Phe Met Met Asp Ile Ala Ala Gly Met Glu Tyr Leu Ser Leu Gln
            675                 680                 685 ggt ttc tta cac aga gat ctg gcc gcc cgc aac tgc atg ttg ggt gat          2112
Gly Phe Leu His Arg Asp Leu Ala Ala Arg Asn Cys Met Leu Gly Asp
        690                 695                 700 gat ctg cgt gtg tgt gtg gcg gac ttt ggc ctc tct aag atg atg tat          2160
Asp Leu Arg Val Cys Val Ala Asp Phe Gly Leu Ser Lys Met Met Tyr
705                 710                 715                 720 tcc agc aac tac tac aga cat aag agt cag gat gtt aaa ctg cct gtg          2208
Ser Ser Asn Tyr Tyr Arg His Lys Ser Gln Asp Val Lys Leu Pro Val
                725                 730                 735 agg tgg atg gcc ata gag agt gtg tca gac ttc ata ttc acc acc aag          2256
Arg Trp Met Ala Ile Glu Ser Val Ser Asp Phe Ile Phe Thr Thr Lys
            740                 745                 750 agt gat gtg tgg tca ttt ggg gta acc atg tgg gag atc aca tct aga          2304
Ser Asp Val Trp Ser Phe Gly Val Thr Met Trp Glu Ile Thr Ser Arg
        755                 760                 765 ggg aag gta cct tat cca ggt gtc tcc aat tac gag ctt ctg gac tac          2352
Gly Lys Val Pro Tyr Pro Gly Val Ser Asn Tyr Glu Leu Leu Asp Tyr
770                 775                 780 ctg gaa aaa gga cat cgg ctt agc caa ggg gac aat gac agc aaa cta          2400
Leu Glu Lys Gly His Arg Leu Ser Gln Gly Asp Asn Asp Ser Lys Leu
785                 790                 795                 800 tat gag ctt atg ttg agc tgc tgg cac aga gat cca tct cag aga cca          2448
Tyr Glu Leu Met Leu Ser Cys Trp His Arg Asp Pro Ser Gln Arg Pro
                805                 810                 815 agt ttt gga gag ctg cac cag agc ttc agt gct ctt ctg tct gag ctt          2496
Ser Phe Gly Glu Leu His Gln Ser Phe Ser Ala Leu Leu Ser Glu Leu
            820                 825                 830 cca ctt ctg gag gac aga atg gag agc cac tac atc aac ctg ggc ctg          2544
Pro Leu Leu Glu Asp Arg Met Glu Ser His Tyr Ile Asn Leu Gly Leu
        835                 840                 845 gag gct gcc aac gat cga cag gac agt gca caa aac cag gtg gaa aat          2592
Glu Ala Ala Asn Asp Arg Gln Asp Ser Ala Gln Asn Gln Val Glu Asn
850                 855                 860 aaa aca gac tat ctg gat ctg ctt aaa act ggt gag ggg ttt gag gaa          2640
Lys Thr Asp Tyr Leu Asp Leu Leu Lys Thr Gly Glu Gly Phe Glu Glu
865                 870                 875                 880 aga gaa gga aag tat aag gag gga gag caa aag tat atg tga                  2682
Arg Glu Gly Lys Tyr Lys Glu Gly Glu Gln Lys Tyr Met
                885                 890

<210> SEQ ID NO 16
<211> LENGTH: 893
<212> TYPE: PRT
<213> ORGANISM: Danio rerio

<400> SEQUENCE: 16

Met Gln Leu Gly Lys Pro His Ala His Pro Val Tyr His Ala Cys Asn
1               5                   10                  15

Pro Lys Phe Lys Lys Ser Lys Lys Leu Leu Thr Lys Trp Ile Pro
            20                  25                  30

Lys Gln Asp Ala Arg Glu Leu Leu Leu Asp Leu Ser Phe Ala Gln Val
        35                  40                  45

Asp Gln Gln Pro Leu Tyr Ile Phe Val Ile Lys Ser Asn Gln Ser Gln
    50                  55                  60

Lys Pro Tyr Gly Pro Gln Lys Pro Val Leu Ala Ile Thr Val Gln His
65                  70                  75                  80

Pro Phe Leu Ala Asn Gly Tyr Pro Arg Asp Glu Asp Leu Ser His Ala
                85                  90                  95
```

```
Lys Ala Leu Asn Leu Gly Asn Ile Ser Glu Asn Gly Phe Tyr Leu Ala
            100                 105                 110
Phe Leu Tyr Ser Gly Asn Cys Met Phe Ile Ala Ser Val Gln Val Phe
        115                 120                 125
Phe Leu Lys Cys Pro Ala Phe Ala Trp Lys Gln Met Lys Phe Glu Glu
    130                 135                 140
Thr Ala Ala Gly Gly Ser Arg Arg Gly Val Cys Val Asp Gly Ala Val
145                 150                 155                 160
Glu Ile Ser Thr Pro Leu Thr Glu Cys Gln Ser Asn Gly Thr Trp Ala
                165                 170                 175
Ser Pro Gln Gly Ser Gly Val Gly Arg Ala Glu Tyr Gln Ser Ser Gly
            180                 185                 190
Asp Thr Gly Lys Gly Glu Glu Val Phe Tyr Val Phe Asn Ser Ala Leu
        195                 200                 205
Arg Gly Pro Pro Leu Met Tyr Ile Ile Asp Tyr Ile Ala Gln Met Ser
    210                 215                 220
Thr Ile Gly Gly Thr Ala Glu Trp Asn Ala Leu Asn Gln Gly Val Asp
225                 230                 235                 240
Glu Ile Leu Leu Thr Tyr Asn Trp Trp Pro Glu Cys Asn Ser Lys Pro
                245                 250                 255
Ser Lys Ala His Glu Asn Pro Met Arg Leu Thr Lys Pro Phe Asn Ala
            260                 265                 270
His Asn Leu Gly Ser Asp Ser Gly Ser Asp Leu Lys Thr Lys Pro Gly
        275                 280                 285
Leu Ala Glu Asn Thr Thr Thr Val Lys Leu Leu Ile Asn Lys Asp Pro
    290                 295                 300
Thr Glu Leu Gln Asp Ser Glu Gly Glu Arg Lys Val His Ile Leu Ser
305                 310                 315                 320
Ser Ser Ile Ile Ala Arg Ala Ile Lys Lys Trp Met Arg Pro Tyr Gly
                325                 330                 335
Gln Tyr Phe Cys Glu Thr Val Glu Leu Leu Gln Asp Arg Val Phe Met
            340                 345                 350
Ala Phe Cys Ile Ala Met Phe Leu Phe Ser Leu Gly Ala Phe Pro Pro
        355                 360                 365
Val Leu Phe Met Glu Asp Val Ala Gln Ser Glu Gly Leu Ile Asp Gly
    370                 375                 380
Ile Ala Leu Ile Pro Leu Val Ser Ile Val Ala Met Thr Thr Gly Ile
385                 390                 395                 400
Gly Lys Leu Ile Leu Gly Val Leu Ala Asp Met Arg Trp Val Asn Ser
                405                 410                 415
Leu Tyr Leu Tyr Ala Leu Thr Leu Ile Gly Ser Gly Thr Ala Leu Leu
            420                 425                 430
Leu Ile Pro Val Ser Lys Ser Tyr Leu Gly Leu Gln Ile Leu Ser Ala
        435                 440                 445
Ala Val Gly Phe Phe Ser Gly Asn Trp Ser Leu Thr Ser Tyr Ile Thr
    450                 455                 460
Thr Lys Ile Val Gly Ile Glu Arg Leu Gly Gln Ala His Gly Ile Leu
465                 470                 475                 480
Met Cys Phe Gly Gly Phe Gly Ile Ala Leu Gly Pro Pro Val Val Val
                485                 490                 495
Ser Asp Ser Asp Gln Met Leu Asp Gly Ile Lys Asp His Leu Leu Cys
            500                 505                 510
Leu Arg Asp Val Leu Val Glu Arg Thr Lys Leu Gln Leu Ser Gln Lys
```

```
            515                 520                 525
Leu Gly Lys Gly Glu Phe Gly Ala Val Tyr Glu Gly Ile Phe Ser Pro
        530                 535                 540

Lys Ile Gly Gln Asp Ile Arg Val Ala Val Lys Thr Ser Lys Asp Val
545                 550                 555                 560

Ile His Ser Glu Glu Asp Leu Glu Ser Phe Leu Lys Glu Ala Glu Met
                565                 570                 575

Met Lys His Phe Asp His Val Asn Val Val Lys Leu Leu Gly Phe Ser
            580                 585                 590

Pro Asn Pro Thr Ala Pro Ala Tyr Ala Gln His Leu Leu Ser Arg Cys
        595                 600                 605

Pro Thr Arg Ser Val Phe Tyr Pro Pro Cys Leu Phe Leu Val Met Gly
    610                 615                 620

Val Ala Leu Glu Trp Asp Pro Glu Ser Ser Met Val Val Pro Leu Val
625                 630                 635                 640

Ile Leu Pro Tyr Met Lys His Arg Asp Leu His Ser Phe Leu Arg Ala
                645                 650                 655

Thr Arg Tyr Asp Asp Val Pro Met Phe Val Pro His Gln Ser Leu Leu
            660                 665                 670

Arg Phe Met Met Asp Ile Ala Ala Gly Met Glu Tyr Leu Ser Leu Gln
        675                 680                 685

Gly Phe Leu His Arg Asp Leu Ala Ala Arg Asn Cys Met Leu Gly Asp
    690                 695                 700

Asp Leu Arg Val Cys Val Ala Asp Phe Gly Leu Ser Lys Met Met Tyr
705                 710                 715                 720

Ser Ser Asn Tyr Tyr Arg His Lys Ser Gln Asp Val Lys Leu Pro Val
                725                 730                 735

Arg Trp Met Ala Ile Glu Ser Val Ser Asp Phe Ile Phe Thr Thr Lys
            740                 745                 750

Ser Asp Val Trp Ser Phe Gly Val Thr Met Trp Glu Ile Thr Ser Arg
        755                 760                 765

Gly Lys Val Pro Tyr Pro Gly Val Ser Asn Tyr Glu Leu Leu Asp Tyr
    770                 775                 780

Leu Glu Lys Gly His Arg Leu Ser Gln Gly Asp Asn Asp Ser Lys Leu
785                 790                 795                 800

Tyr Glu Leu Met Leu Ser Cys Trp His Arg Asp Pro Ser Gln Arg Pro
                805                 810                 815

Ser Phe Gly Glu Leu His Gln Ser Phe Ser Ala Leu Leu Ser Glu Leu
            820                 825                 830

Pro Leu Leu Glu Asp Arg Met Glu Ser His Tyr Ile Asn Leu Gly Leu
        835                 840                 845

Glu Ala Ala Asn Asp Arg Gln Asp Ser Ala Gln Asn Gln Val Glu Asn
    850                 855                 860

Lys Thr Asp Tyr Leu Asp Leu Leu Lys Thr Gly Glu Gly Phe Glu Glu
865                 870                 875                 880

Arg Glu Gly Lys Tyr Lys Glu Gly Glu Gln Lys Tyr Met
                885                 890

<210> SEQ ID NO 17
<211> LENGTH: 679
<212> TYPE: PRT
<213> ORGANISM: Artificial
<220> FEATURE:
<223> OTHER INFORMATION: synthetic

<400> SEQUENCE: 17
```

```
Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
                20                  25                  30

Glu Glu Ser Pro Phe Val Gly Asn Pro Gly Asn Ile Thr Gly Ala Arg
            35                  40                  45

Gly Leu Thr Gly Thr Leu Arg Cys Gln Leu Gln Val Gln Gly Glu Pro
        50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
        130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
        210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
290                 295                 300

Tyr His Ile Arg Val Ala Cys Thr Ser Ser Gln Gly Pro Ser Ser Trp
305                 310                 315                 320

Thr His Trp Leu Pro Val Glu Thr Pro Glu Gly Val Pro Leu Gly Pro
                325                 330                 335

Pro Glu Asn Ile Ser Ala Thr Arg Asn Gly Ser Gln Ala Phe Val His
            340                 345                 350

Trp Gln Glu Pro Arg Ala Pro Leu Gln Gly Thr Leu Leu Gly Tyr Arg
        355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Ala Gly Asp Gly Pro
                405                 410                 415

Trp Ser Leu Pro Val Pro Leu Glu Ala Trp Arg Pro Gly Gln Ala Gln
```

```
                420             425             430
Pro Val His Gln Leu Val Lys Glu Pro Ser Thr Pro Ala Ala Glu
        435             440             445

Pro Lys Ser Cys Asp Lys Thr His Thr Cys Pro Pro Cys Pro Ala Pro
    450             455             460

Glu Leu Leu Gly Gly Pro Ser Val Phe Leu Phe Pro Pro Lys Pro Lys
465             470             475             480

Asp Thr Leu Met Ile Ser Arg Thr Pro Glu Val Thr Cys Val Val Val
            485             490             495

Asp Val Ser His Glu Asp Pro Glu Val Lys Phe Asn Trp Tyr Val Asp
            500             505             510

Gly Val Glu Val His Asn Ala Lys Thr Lys Pro Arg Glu Glu Gln Tyr
        515             520             525

Asn Ser Thr Tyr Arg Val Val Ser Val Leu Thr Val Leu His Gln Asp
    530             535             540

Trp Leu Asn Gly Lys Glu Tyr Lys Cys Lys Val Ser Asn Lys Ala Leu
545             550             555             560

Pro Ala Pro Ile Glu Lys Thr Ile Ser Lys Ala Lys Gly Gln Pro Arg
                565             570             575

Glu Pro Gln Val Tyr Thr Leu Pro Pro Ser Arg Glu Glu Met Thr Lys
                580             585             590

Asn Gln Val Ser Leu Thr Cys Leu Val Lys Gly Phe Tyr Pro Ser Asp
            595             600             605

Ile Ala Val Glu Trp Glu Ser Asn Gly Gln Pro Glu Asn Asn Tyr Lys
        610             615             620

Thr Thr Pro Pro Val Leu Asp Ser Asp Gly Ser Phe Phe Leu Tyr Ser
625             630             635             640

Lys Leu Thr Val Asp Lys Ser Arg Trp Gln Gln Gly Asn Val Phe Ser
                645             650             655

Cys Ser Val Met His Glu Ala Leu His Asn His Tyr Thr Gln Lys Ser
                660             665             670

Leu Ser Leu Ser Pro Gly Lys
        675

<210> SEQ ID NO 18
<211> LENGTH: 7
<212> TYPE: PRT
<213> ORGANISM: Artificial
<220> FEATURE:
<223> OTHER INFORMATION: synthetic peptide
<220> FEATURE:
<221> NAME/KEY: VARIANT
<222> LOCATION: (3)..(3)
<223> OTHER INFORMATION: X = Isoleucine or Leucine
<220> FEATURE:
<221> NAME/KEY: VARIANT
<222> LOCATION: (5)..(5)
<223> OTHER INFORMATION: X = Isoleucine or Leucine

<400> SEQUENCE: 18

Lys Trp Xaa Ala Xaa Glu Ser
1               5
```